United States Patent
Flom et al.

(10) Patent No.: US 10,245,070 B2
(45) Date of Patent: Apr. 2, 2019

(54) METHOD AND APPARATUS FOR ACCESSING THE INTERIOR OF A HIP JOINT, INCLUDING THE PROVISION AND USE OF A NOVEL TELESCOPING ACCESS CANNULA AND A NOVEL TELESCOPING OBTURATOR

(71) Applicant: Pivot Medical, Inc., Sunnyvale, CA (US)

(72) Inventors: James Flom, San Carlos, CA (US); Thomas Weisel, Ventura, CA (US); Andrew Lantz, Redwood City, CA (US); Roger Pisarnwongs, Valencia, CA (US); Jonathan Dewey, Raleigh, NC (US); Matthew Frushell, Danville, CA (US); Bryan Kelly, New York, NY (US); Michael Wei, Redwood City, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 0 days.

(21) Appl. No.: 14/885,524

(22) Filed: Oct. 16, 2015

(65) Prior Publication Data

US 2016/0100858 A1  Apr. 14, 2016

Related U.S. Application Data

(63) Continuation of application No. 13/868,390, filed on Apr. 23, 2013, now Pat. No. 9,161,839, which is a
(Continued)

(51) Int. Cl.
*A61B 17/34* (2006.01)
*A61B 17/02* (2006.01)
(Continued)

(52) U.S. Cl.
CPC ...... *A61B 17/3423* (2013.01); *A61B 17/0218* (2013.01); *A61B 17/3421* (2013.01);
(Continued)

(58) Field of Classification Search
CPC ..... A61B 17/34; A61B 17/02; A61B 17/3423; A61B 17/0218; A61F 2/46; A61F 2/4607; A61F 2/4609
See application file for complete search history.

(56) References Cited

U.S. PATENT DOCUMENTS 3,406,685 A  10/1968  May
3,509,883 A  5/1970  Dibelius
(Continued)

FOREIGN PATENT DOCUMENTS

WO  WO 2004/098395  11/2004
WO  WO 2006/017507  2/2006

*Primary Examiner* — Christopher J Beccia
(74) *Attorney, Agent, or Firm* — Pandiscio & Pandiscio

(57) ABSTRACT

A telescoping access cannula comprising:
an outer tube;
an inner tube carried by the outer tube, the inner tube being coaxial with the outer tube and longitudinally movable relative to the outer tube; and
a rotatable member carried by the outer tube and connected to the inner tube, wherein rotation of the rotatable member causes longitudinal movement of the inner tube relative to the outer tube.

66 Claims, 74 Drawing Sheets

Related U.S. Application Data continuation of application No. 12/631,514, filed on Dec. 4, 2009, now Pat. No. 8,425,532.

(60) Provisional application No. 61/200,908, filed on Dec. 4, 2008, provisional application No. 61/269,605, filed on Jun. 26, 2009.

(51) Int. Cl.
*A61F 2/46* (2006.01)
*A61F 2/32* (2006.01)
*A61B 17/00* (2006.01)

(52) U.S. Cl.
CPC .............. *A61F 2/32* (2013.01); *A61F 2/4607* (2013.01); *A61F 2/4609* (2013.01); *A61B 2017/00991* (2013.01); *A61B 2017/347* (2013.01); *A61B 2017/3443* (2013.01)

(56) References Cited

U.S. PATENT DOCUMENTS

| | | |
|---|---|---|
| 4,127,131 A | 11/1978 | Vaillancourt |
| 4,405,307 A | 9/1983 | Taylor |
| 4,670,008 A | 6/1987 | Von Albertini |
| 4,723,550 A | 2/1988 | Bales et al. |
| 4,842,591 A | 6/1989 | Luther |
| 4,960,412 A | 10/1990 | Fink |
| 5,197,955 A | 3/1993 | Stephens et al. |
| 5,217,441 A | 6/1993 | Shichman et al. |
| 5,226,891 A | 7/1993 | Bushatz et al. |
| 5,248,298 A | 9/1993 | Bedi et al. |
| 5,281,197 A | 1/1994 | Arias et al. |
| 5,308,336 A | 5/1994 | Hart et al. |
| 5,336,206 A | 8/1994 | Shichman |
| 5,342,315 A | 8/1994 | Rowe et al. |
| 5,350,364 A | 9/1994 | Stephens et al. |
| 5,364,372 A | 11/1994 | Danks et al. |
| 5,366,445 A | 11/1994 | Haber et al. |
| 5,370,625 A | 12/1994 | Shichman |
| 5,385,552 A | 1/1995 | Haber et al. |
| 5,385,553 A | 1/1995 | Hart et al. |
| 5,411,483 A | 5/1995 | Loomas et al. |
| 5,431,638 A | 7/1995 | Hennig et al. |
| 5,464,011 A | 11/1995 | Bridge |
| 5,476,475 A | 12/1995 | Gadberry |
| 5,480,389 A * | 1/1996 | McWha .............. A61B 17/3401 604/158 |
| 5,496,280 A | 3/1996 | Vandenbroek et al. |
| 5,496,289 A | 3/1996 | Wenstrom, Jr. |
| 5,538,509 A | 7/1996 | Dunlap et al. |
| 5,556,411 A | 9/1996 | Taoda et al. |
| 5,603,702 A | 2/1997 | Smith et al. |
| 5,628,732 A | 5/1997 | Antoon, Jr. et al. |
| 5,630,805 A | 5/1997 | Ternamian |
| 5,657,963 A | 8/1997 | Hinchliffe et al. |
| 5,693,031 A | 12/1997 | Ryan et al. |
| 5,709,664 A | 1/1998 | Vandenbroek et al. |
| 5,727,770 A | 3/1998 | Dennis |
| 5,746,720 A * | 5/1998 | Stouder, Jr. ........ A61B 17/3417 604/117 |
| 5,752,938 A | 5/1998 | Flatland et al. |
| 5,782,812 A | 7/1998 | Hart et al. |
| 5,792,113 A | 8/1998 | Kramer et al. |
| 5,803,919 A | 9/1998 | Hart et al. |
| 5,820,600 A | 10/1998 | Carlson et al. |
| 5,827,228 A | 10/1998 | Rowe |
| 5,879,332 A | 3/1999 | Schwemberger et al. |
| 5,882,344 A | 3/1999 | Stouder, Jr. |
| 5,895,377 A | 4/1999 | Smith et al. |
| 5,941,852 A | 8/1999 | Dunlap et al. |
| 5,947,930 A | 9/1999 | Schwemberger et al. |
| 5,957,888 A * | 9/1999 | Hinchliffe .......... A61B 17/3421 604/117 |
| 5,997,510 A | 12/1999 | Schwemberger |
| 6,019,776 A | 2/2000 | Preissman |
| 6,066,117 A | 5/2000 | Fox et al. |
| 6,197,002 B1 | 3/2001 | Peterson |
| 6,213,978 B1 | 4/2001 | Voyten |
| 6,217,555 B1 | 4/2001 | Hart et al. |
| 6,228,061 B1 | 5/2001 | Flatland et al. |
| 6,273,870 B1 | 8/2001 | Garvin |
| D449,887 S | 10/2001 | Haberland et al. |
| 6,319,266 B1 | 11/2001 | Stellon et al. |
| 6,394,979 B1 | 5/2002 | Sharp et al. |
| 6,432,085 B1 | 8/2002 | Stellon et al. |
| 6,482,181 B1 | 11/2002 | Racenet et al. |
| 6,524,238 B2 * | 2/2003 | Velikaris ................ A61B 17/02 16/422 |
| 6,551,282 B1 | 4/2003 | Exline et al. |
| 6,569,119 B1 | 5/2003 | Haberland et al. |
| 6,595,946 B1 | 7/2003 | Pasqualucci |
| 6,626,864 B2 | 9/2003 | Jansen et al. |
| 6,685,676 B2 | 2/2004 | Jansen et al. |
| 6,702,787 B2 | 3/2004 | Racenet et al. |
| 6,761,704 B2 | 7/2004 | Crawford |
| 7,025,747 B2 | 4/2006 | Smith |
| 7,367,960 B2 | 5/2008 | Stellon et al. |
| 7,559,918 B2 | 7/2009 | Pasqualucci |
| 7,563,268 B2 * | 7/2009 | Ishikawa ........ A61B 17/320068 606/167 |
| 7,582,073 B2 | 9/2009 | Barrelle et al. |
| 7,585,288 B2 | 9/2009 | Haberland et al. |
| 7,749,250 B2 | 7/2010 | Stone et al. |
| 7,798,991 B2 | 9/2010 | Insignares |
| 7,824,419 B2 | 11/2010 | Boraiah |
| 7,828,775 B2 | 11/2010 | Okoniewski |
| 7,842,013 B2 | 11/2010 | Haberland et al. |
| 7,896,845 B2 | 3/2011 | Ross et al. |
| 7,905,884 B2 | 3/2011 | Simonton et al. |
| 8,012,129 B2 | 9/2011 | Bettuchi et al. |
| 8,057,438 B2 | 11/2011 | Bettuchi |
| 8,114,053 B2 | 2/2012 | Fischvogt et al. |
| 8,133,237 B2 | 3/2012 | Oostman, Jr. et al. |
| 8,147,453 B2 | 4/2012 | Albrecht et al. |
| 8,298,188 B2 | 10/2012 | Okoniewski |
| 8,425,532 B2 | 4/2013 | Flom et al. |
| 8,430,851 B2 | 4/2013 | McGinley et al. |
| 8,439,881 B2 | 5/2013 | Shelton, IV |
| 8,506,475 B2 | 8/2013 | Brannon |
| 2002/0045862 A1 | 4/2002 | Briscoe et al. |
| 2002/0058910 A1 | 5/2002 | Hermann et al. |
| 2003/0078540 A1 | 4/2003 | Saulenas et al. |
| 2004/0260246 A1 * | 12/2004 | Desmond .......... A61B 17/3421 604/174 |
| 2005/0070946 A1 | 3/2005 | Franer |
| 2005/0075655 A1 | 4/2005 | Bumbalough et al. |
| 2005/0096507 A1 | 5/2005 | Prosek |
| 2005/0277942 A1 * | 12/2005 | Kullas ................ A61F 2/0063 606/99 |
| 2006/0041270 A1 * | 2/2006 | Lenker ............... A61B 17/3439 606/198 |
| 2006/0047293 A1 | 3/2006 | Haberland et al. |
| 2006/0200185 A1 | 9/2006 | Marchek et al. |
| 2006/0200186 A1 | 9/2006 | Marchek et al. |
| 2007/0066943 A1 | 3/2007 | Prasad |
| 2007/0185453 A1 | 8/2007 | Michael et al. |
| 2008/0249481 A1 | 10/2008 | Crainich et al. |
| 2008/0275301 A1 | 11/2008 | Lubowski et al. |
| 2008/0287926 A1 | 11/2008 | Abou El |
| 2009/0204081 A1 | 8/2009 | Whittaker et al. |
| 2009/0259184 A1 | 10/2009 | Okoniewski |
| 2009/0306586 A1 | 12/2009 | Ross et al. |
| 2010/0063450 A1 | 3/2010 | Smith et al. |
| 2010/0324488 A1 | 12/2010 | Smith |
| 2012/0109064 A1 | 5/2012 | Fischvogt et al. |
| 2013/0303858 A1 | 11/2013 | Whittaker et al. |

* cited by examiner

CAM-TYPE FEMOROACETABULAR IMPINGEMENT (FAI)
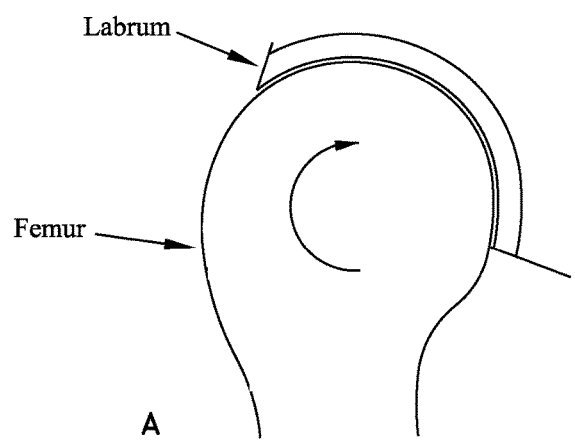
CAM INJURY TO THE LABRUM
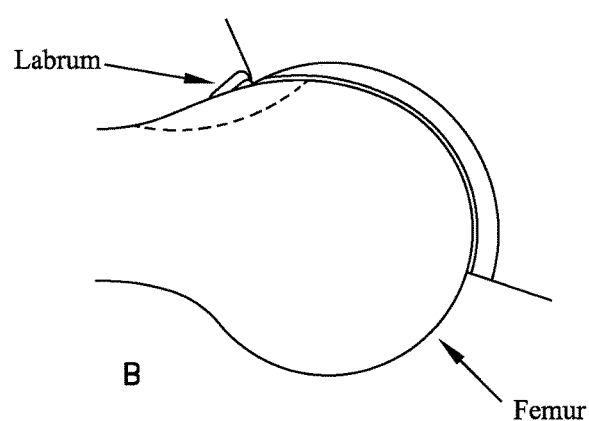
FIG. 13

PINCER-TYPE FEMOROACETABULAR IMPINGEMENT (FAI)
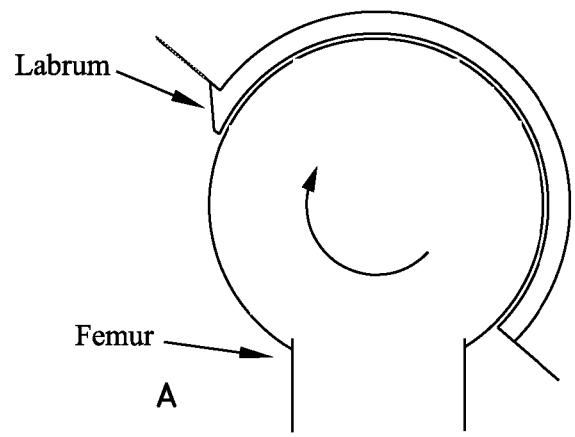
PINCER INJURY TO THE LABRUM
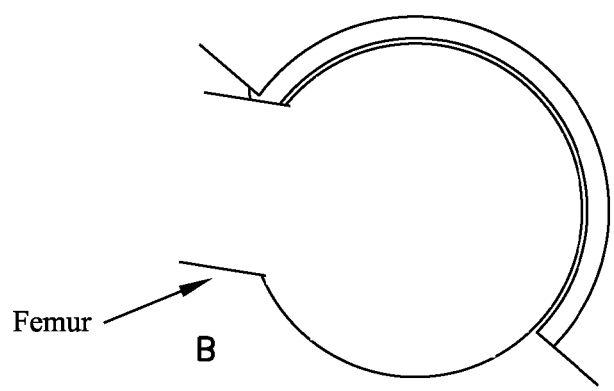
FIG. 14

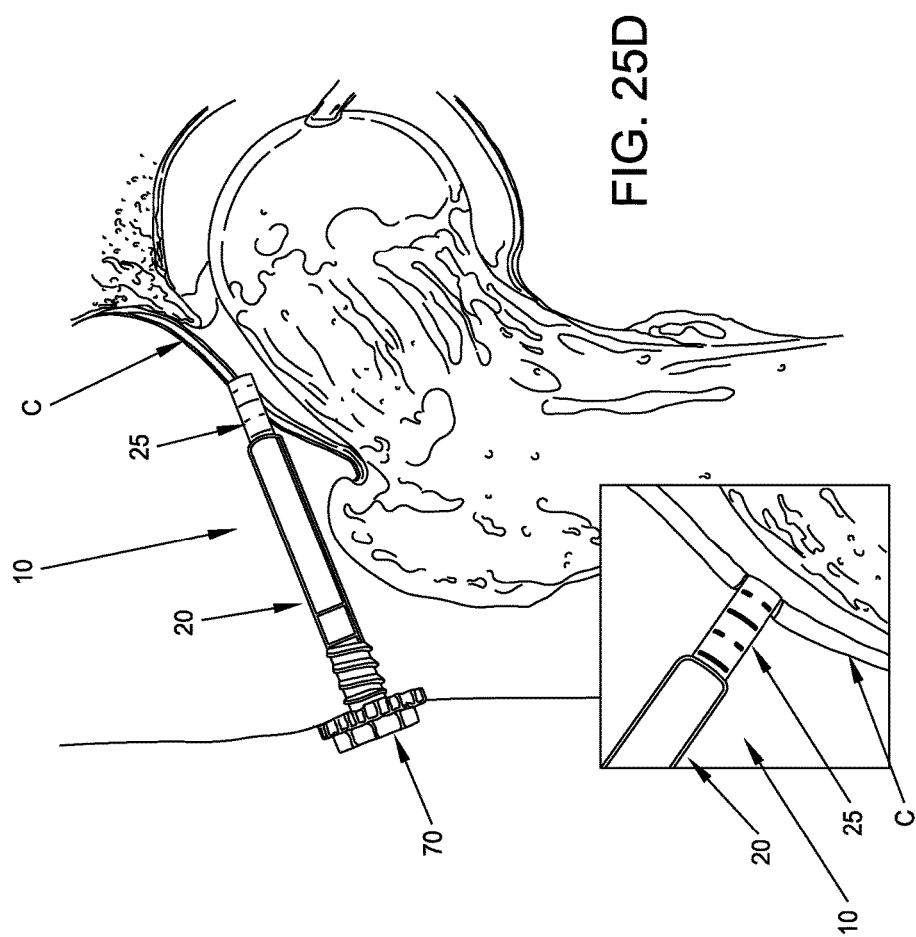

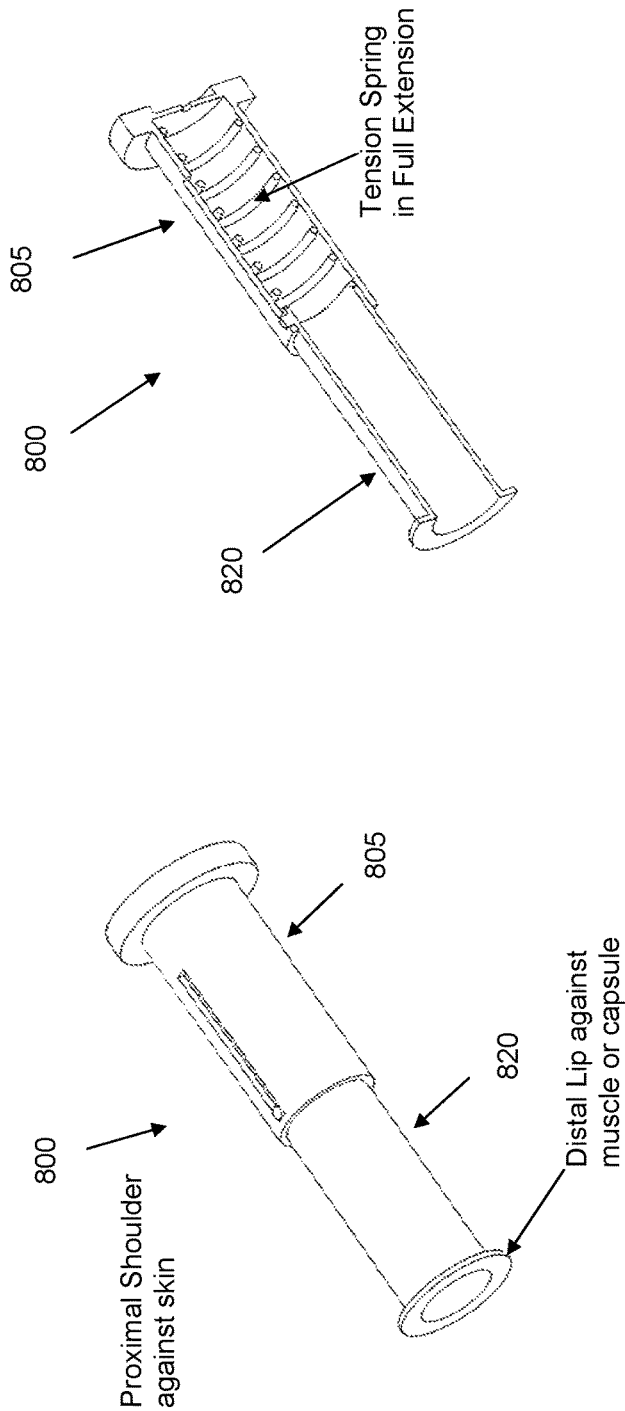

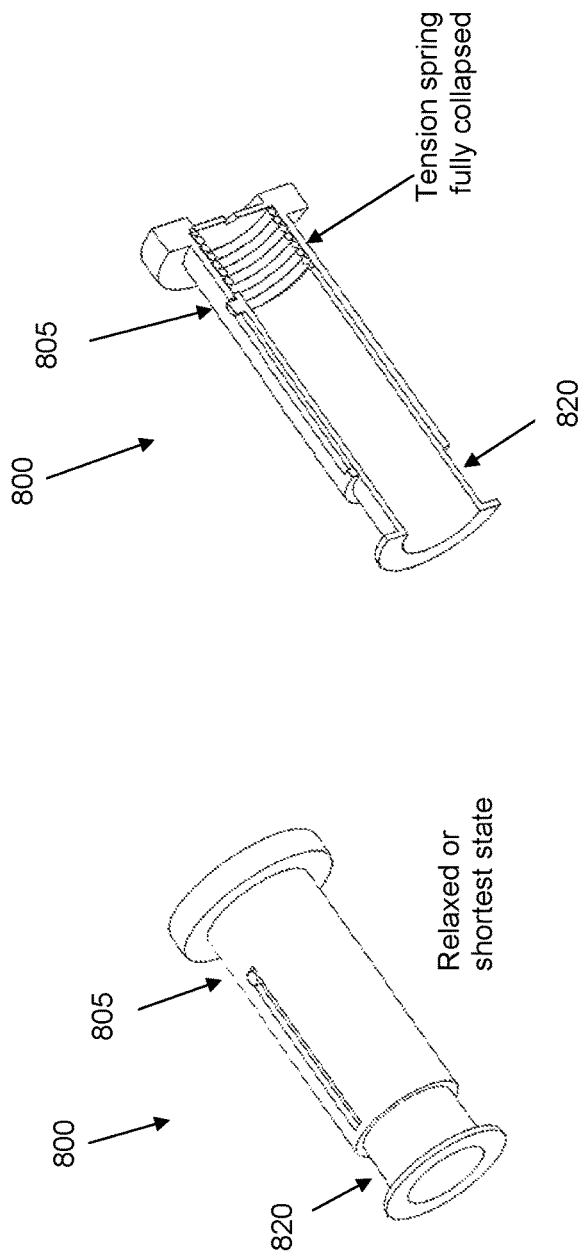

METHOD AND APPARATUS FOR ACCESSING THE INTERIOR OF A HIP JOINT, INCLUDING THE PROVISION AND USE OF A NOVEL TELESCOPING ACCESS CANNULA AND A NOVEL TELESCOPING OBTURATOR

REFERENCE TO PENDING PRIOR PATENT APPLICATIONS

This patent application is a continuation of prior U.S. patent application Ser. No. 13/868,390, filed Apr. 23, 2013 by Pivot Medical, Inc. for METHOD AND APPARATUS FOR ACCESSING THE INTERIOR OF A HIP JOINT, INCLUDING THE PROVISION AND USE OF A NOVEL TELESCOPING ACCESS CANNULA AND A NOVEL TELESCOPING OBTURATOR, which in turn is a continuation of prior U.S. patent application Ser. No. 12/631,514, filed Dec. 4, 2009 by James Flom et al. for METHOD AND APPARATUS FOR ACCESSING THE INTERIOR OF A HIP JOINT, INCLUDING THE PROVISION AND USE OF A NOVEL TELESCOPING ACCESS CANNULA AND A NOVEL TELESCOPING OBTURATOR, which in turn claims benefit of:

(i) prior U.S. Provisional Patent Application Ser. No. 61/200,908, filed Dec. 4, 2008 by James Flom et al. for METHOD AND APPARATUS FOR ACCESSING THE INTERIOR OF A HIP JOINT, INCLUDING THE PROVISION AND USE OF A NOVEL TELESCOPING ACCESS CANNULA; and (ii) prior U.S. Provisional Patent Application Ser. No. 61/269,605, filed Jun. 26, 2009 by James Flom et al. for METHOD AND APPARATUS FOR ACCESSING THE INTERIOR OF A HIP JOINT, INCLUDING THE PROVISION AND USE OF A NOVEL TELESCOPING ACCESS CANNULA.

The above-identified patent applications are hereby incorporated herein by reference.

FIELD OF THE INVENTION

This invention relates to surgical methods and apparatus in general, and more particularly to surgical methods and apparatus for treating the hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the femur and the hip. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body of the femur adjacent to the neck of the femur. A second, somewhat smaller projection known as the lesser trochanter protrudes medially and posteriorly from the elongated body of the femur adjacent to the neck of the femur. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25) so as to collectively form the acetabular cup. The acetabular cup receives the hemispherical head (i.e., the ball) of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIG. 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12 which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as a cam-type femoroacetabular impingement (i.e., a cam-type FAI). In other cases, and looking now at FIG. 14, the impingement can occur due to irregularities in the geometry of the acetabular cup. This latter type of impingement is sometimes referred to as a pincer-type femoroacetabular impingement (i.e., a pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The Current Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and the knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the pathways which exist between adjacent bones, avoid major vascular structures and delicate neurological tissues, etc.) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive procedures for the hip joint are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Arthroscopic Access to the Interior of the Hip Joint

Successful hip arthroscopy generally requires safe and effective access to the interior of the hip joint. More particularly, successful hip arthroscopy generally requires the creation of a plurality of access portals which extend inwardly from the surface of the skin, down to the interior of the hip joint, extending through the intervening layers of tissue, including skin, fat, muscle and capsule tissue. These access portals may also continue down to the specific surgical site within the interior of the hip joint. Depending on the specific surgical site which is to be accessed within the interior of the hip joint, different anatomical pathways may be utilized for the access portals. By way of example but not limitation, one anatomical pathway may be used where a torn labrum is to be repaired, and another anatomical pathway may be used where the lesser trochanter must be addressed. And, in most cases, multiple access portals are required, with one access portal being used for visualization (i.e., to introduce an arthroscope into the interior of the hip joint), while other access portals are used for irrigation and to pass surgical instruments to and from the surgical site, etc.

Establishing these access portals typically involves forming an opening from the top surface of the skin down to the interior of the joint, and lining that opening with a tubular liner (sometimes referred to as an "access cannula"). This access cannula holds the incision open and provides a surgical pathway (or "corridor") from the top surface of the skin down to the interior of the hip joint, thereby enabling instrumentation (e.g., arthroscopes, surgical instruments, etc.) to be passed through the central lumen of the access cannula so as to reach the remote surgical site within the joint. Thus the provision and use of access cannulas are generally an important aspect of enabling minimally-invasive, "keyhole" surgery to be performed on the hip joint.

Prior Art Access Cannulas

Access cannulas have traditionally been tubular structures of fixed length. However, this fixed length construction can be problematic for a variety of reasons. For the sake of convenience, these problems can generally be broken down into "static" considerations and "dynamic" considerations.

"Static" Considerations

First, it will be appreciated that patients have anatomies of different sizes, so that an access cannula of a given length might be too short for one patient and too long for another patient. In this respect it will be appreciated that it is generally necessary for the access cannula to extend the entire distance from the top of the skin down to the interior of the hip joint in order to ensure safe instrument passage. However, it will also be appreciated that it is generally undesirable for the access cannula to extend an excessive distance above the top surface of the skin, since this can create a field of protruding cannula "masts" which can obstruct other surgeon activities, impede access of instruments into the joint space, limit the available working length of the surgical instruments (thereby limiting the ability to treat pathologies of the joint), etc.

Second, the patient's anatomy generally dictates that only certain entry points may be used for the access portals, and various procedures must generally address specific regions of the joint, so that—even when dealing with the anatomy of only a single patient—each access corridor may extend for a different span and thus require the use of an access cannula of a different length.

It will also be appreciated that it is generally undesirable for the distal end of the access cannula to extend an excessive distance into the joint compartment, since this would tend to limit visualization within the joint by the arthroscope and/or limit the range of motion of a surgical instrument within the joint space.

The foregoing considerations would suggest that manufacturers should offer their access cannulas in a range of different lengths. However, such an approach would create substantial inventory issues for manufacturers as well as for healthcare facilities (e.g., hospitals, surgical centers, etc.), all of whom must stock the access cannulas prior to surgery. For this reason, access cannulas are generally manufactured with a fixed length which is generally adequate, but not optimal, for most patients and most procedures.

"Dynamic" Considerations

In addition to the foregoing, it should also be appreciated that, in many situations, the surgeon may need to adjust the position of the distal end of the cannula during the surgical procedure. This may be required in order to facilitate better visualization of the surgical site, and/or to properly direct instruments at the surgical site, etc. However, with an access cannula of fixed length, this generally requires moving the entire cannula relative to the patient's tissue, which can result in the "loss" of the defined pathway from the top of the skin down to the interior of the hip joint, as well as be traumatic for patient tissue and inconvenient for the surgeon.

In addition, tissue can swell during the course of an arthroscopic procedure, particularly since the joint is typically irrigated with fluid during the arthroscopic surgery in order to improve visualization and wash away debris, etc. Accordingly, a fixed length cannula, even if it may happen to be of an appropriate length at the beginning of a procedure, may become too short during the course of the procedure as the intervening tissue absorbs fluid and swells up in size.

The Need for a New and Improved Access Cannula

On account of the foregoing, it will be appreciated that there is a need for a new and improved access cannula which can have its overall length adjusted, either before deployment in the body or after deployment in the body, or both.

SUMMARY OF THE INVENTION

These and other objects of the present invention are addressed by the provision and use of a new and improved access cannula for accessing the interior of a hip joint or other interior body space. The new and improved access cannula utilizes a telescoping construction so that the overall length of the access cannula can be adjusted, either before deployment in the body or after deployment in the body, or both. In accordance with the present invention, this telescoping construction can be achieved in a variety of different ways, each with its own attendant advantages, as will hereinafter be discussed in further detail.

The present invention also comprises the provision and use of a telescoping obturator which may be used in conjunction with the telescoping access cannula of the present invention.

In one form of the invention, there is provided a telescoping access cannula comprising:
an outer tube;
an inner tube carried by the outer tube, the inner tube being coaxial with the outer tube and longitudinally movable relative to the outer tube; and a rotatable member carried by the outer tube and connected to the inner tube, wherein rotation of the rotatable member causes longitudinal movement of the inner tube relative to the outer tube.

In another form of the invention, there is provided a telescoping access cannula comprising:
an outer tube; and
an inner tube carried by the outer tube, the inner tube being longitudinally movable relative to the outer tube;
wherein movement of the inner tube relative to the outer tube is controlled by movement of a finger relative to a seat.

In another form of the invention, there is provided a telescoping access cannula comprising:
an outer tube; and
an inner tube carried by the outer tube, the inner tube being longitudinally movable relative to the outer tube;
wherein rotational movement of the inner tube relative to the outer tube permits longitudinal motion of at least a portion of the inner tube relative to the outer tube.

In another form of the invention, there is provided a telescoping obturator comprising:
a handle;
a shaft carried by the handle, the shaft being longitudinally movable relative to the handle; and
a locking mechanism for selectively locking the shaft to the handle.

In another form of the invention, there is provided a system comprising a telescoping access cannula and a telescoping obturator disposable within the telescoping access cannula,
the telescoping access cannula comprising:
an outer tube;
an inner tube carried by the outer tube, the inner tube being coaxial with the outer tube and longitudinally movable relative to the outer tube; and
a rotatable member carried by the outer tube and connected to the inner tube, wherein rotation of the rotatable member causes longitudinal movement of the inner tube relative to the outer tube; and
the telescoping obturator comprising:
a handle;
a shaft carried by the handle, the shaft being longitudinally movable relative to the handle; and
a locking mechanism for selectively locking the shaft to the handle.

In another form of the invention, there is provided a system comprising a telescoping access cannula and a telescoping obturator disposable within the telescoping access cannula,
the telescoping access cannula comprising:
an outer tube; and
an inner tube carried by the outer tube, the inner tube being longitudinally movable relative to the outer tube;
wherein movement of the inner tube relative to the outer tube is controlled by movement of a finger relative to a seat; and
the telescoping obturator comprising:
a handle;
a shaft carried by the handle, the shaft being longitudinally movable relative to the handle; and
a locking mechanism for selectively locking the shaft to the handle.

In another form of the invention, there is provided a method for providing an access corridor from a first location located outside the body to a second location located inside the body, the method comprising:

providing a telescoping access cannula having a first overall length and adjustable to a different overall length;
inserting the telescoping access cannula into the body so that the proximal end of the telescoping access cannula is located at the first location and the distal end of the telescoping access cannula is disposed inside the body.

In another form of the invention, there is provided a method for providing an access corridor from a first location located outside the body to a second location located inside the body, the method comprising:
providing a telescoping access cannula having a first overall length and adjustable to a different overall length;
measuring the distance from the first location to the second location;
adjusting the length of the telescoping access cannula from the first overall length to another length which is a function of the distance from the first location to the second location; and
inserting the telescoping access cannula into the body so that the proximal end of the telescoping access cannula is located at the first location and the distal end of the telescoping access cannula is disposed inside the body.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (FAI);

FIG. 14 is a schematic view showing pincer-type femoroacetabular impingement (FAI);

FIGS. 25A-25E are schematic views showing the telescoping access cannula and telescoping obturator of FIGS. 16-25 being used in a surgical procedure;

FIGS. 61-65 are schematic views showing a ninth type of telescoping access cannula formed in accordance with the present invention.

FIRST TYPE OF TELESCOPING ACCESS CANNULA

Figure 1A:
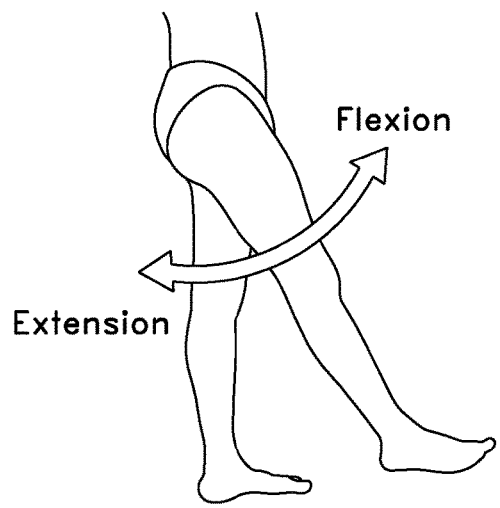
FIGS. 1A-1D are schematic views showing various aspects of hip motion.
Figure 1B:
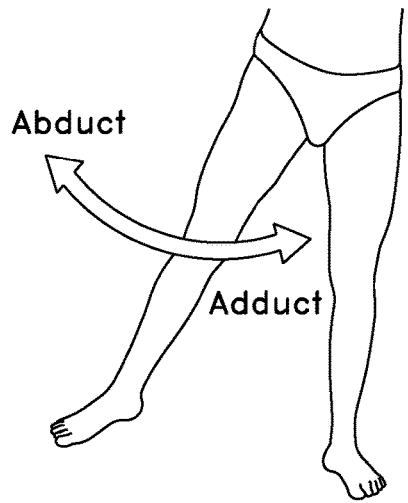
Figure 1C:
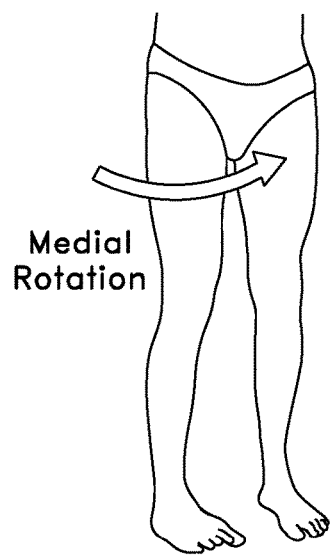
Figure 1D:
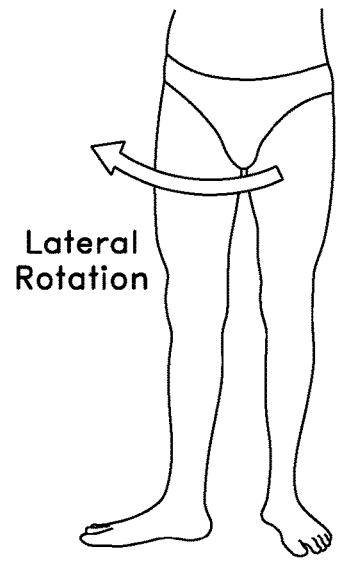
Figure 2:
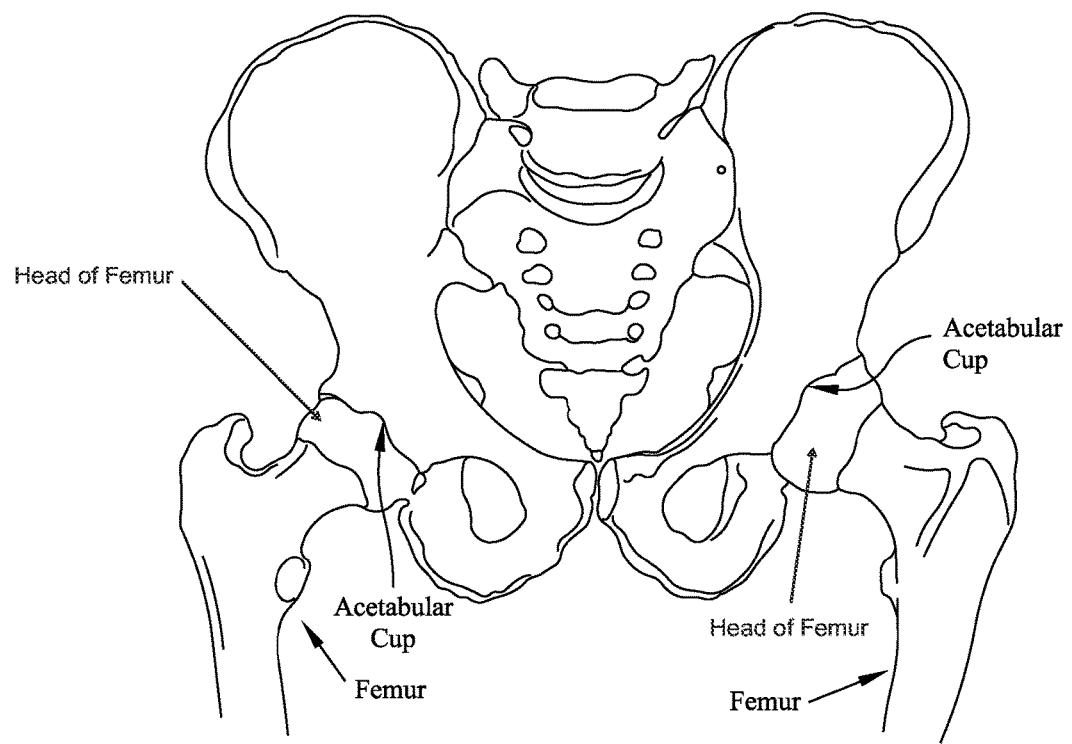
FIG. 2 is a schematic view showing the bone structure in the region of the hip joints.
Figure 3:
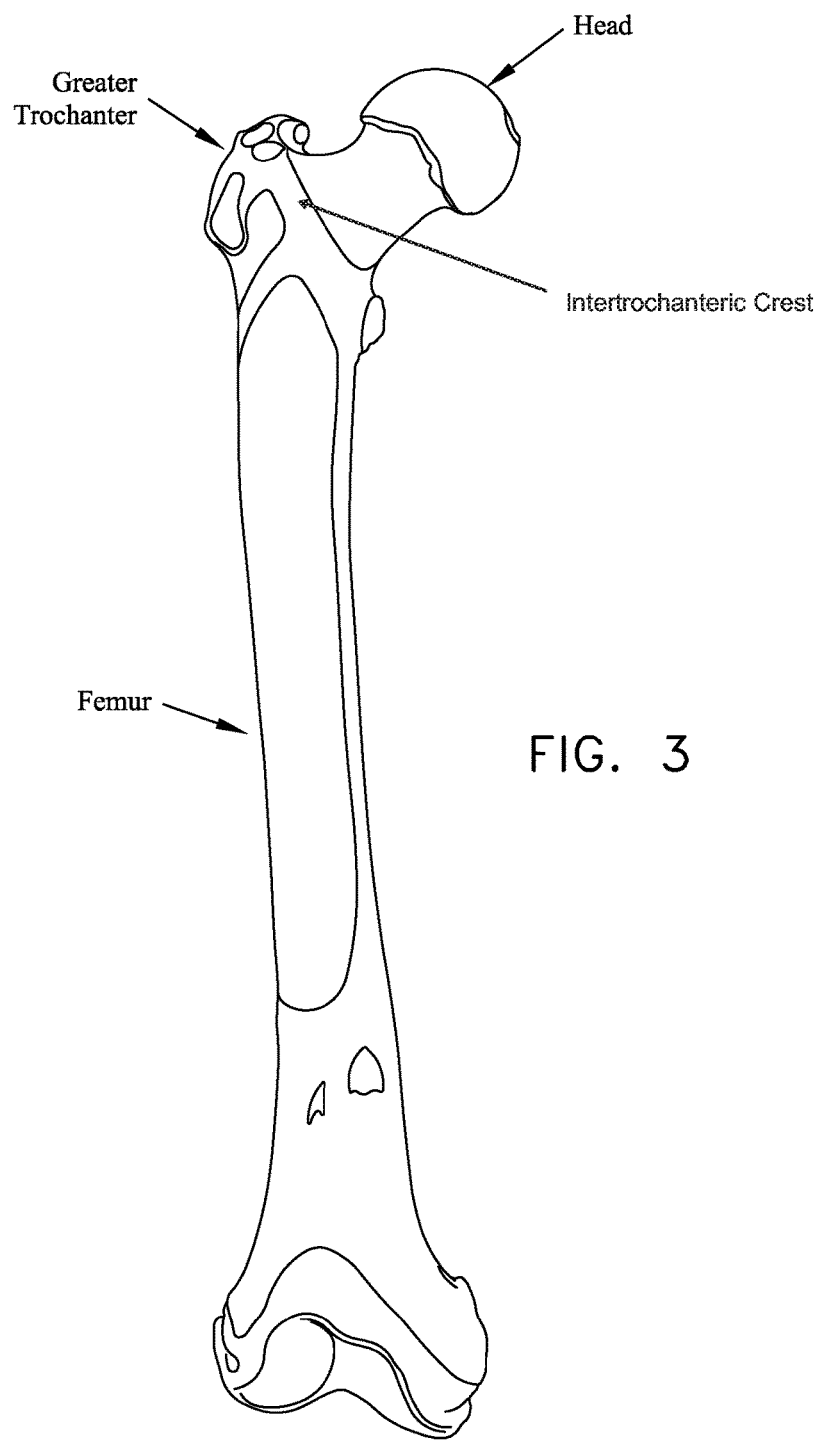
FIG. 3 is a schematic view of the femur.
Figure 4:
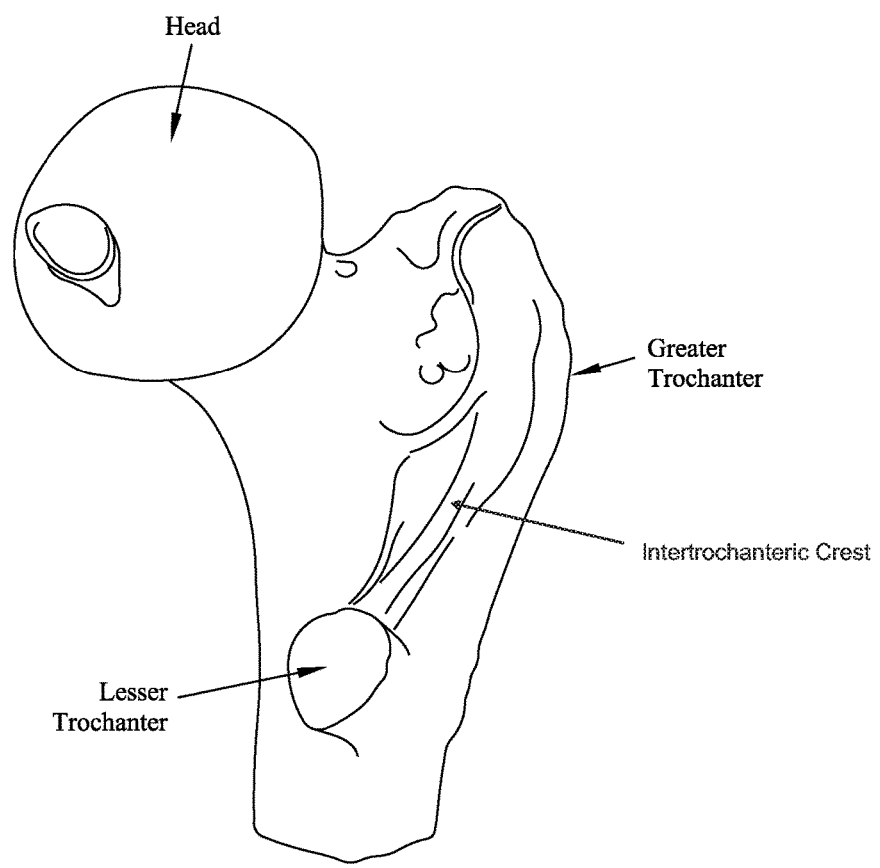
FIG. 4 is a schematic view of the top end of the femur.
Figure 5:
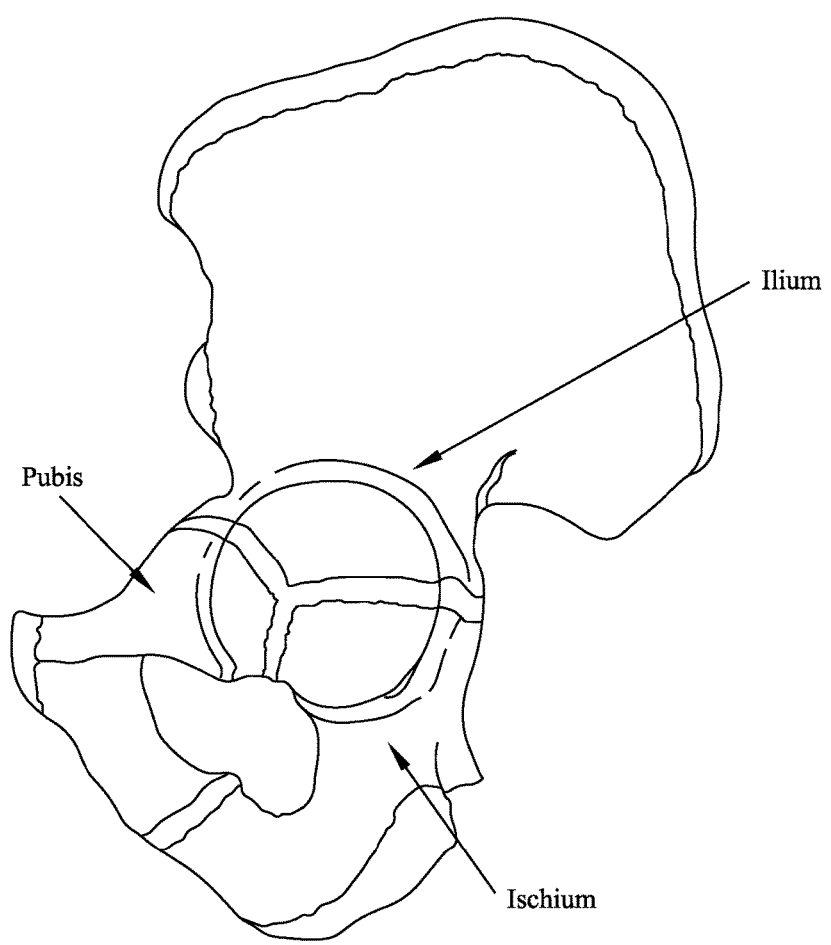
FIG. 5 is a schematic view of the pelvis.
Figure 6:
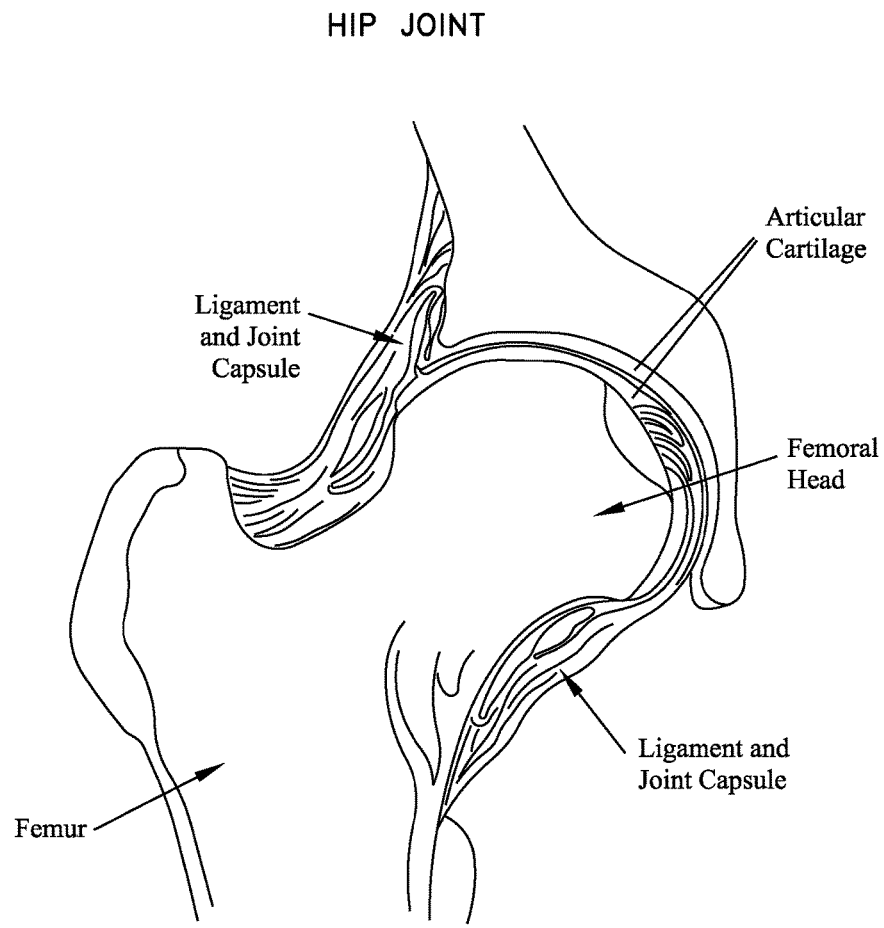
FIGS. 6-12 are schematic views showing the bone and soft tissue structure of the hip joint.
Figure 7:
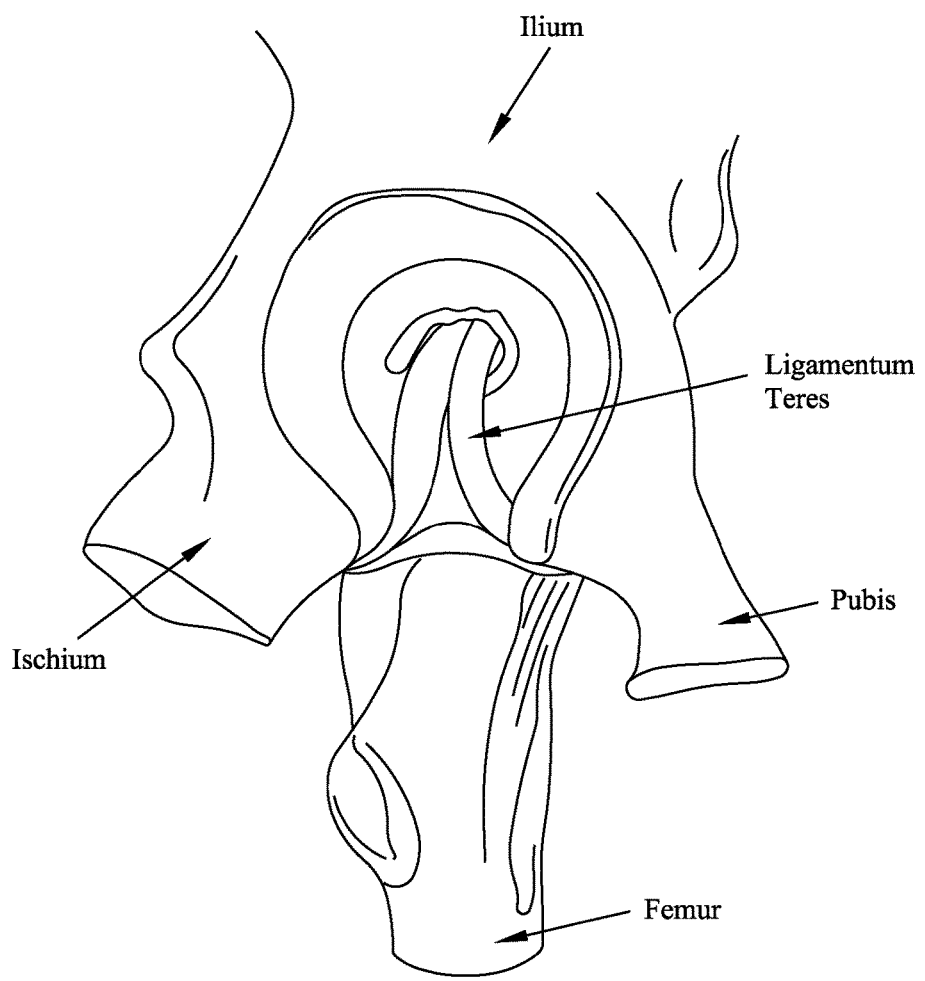
Figure 8:
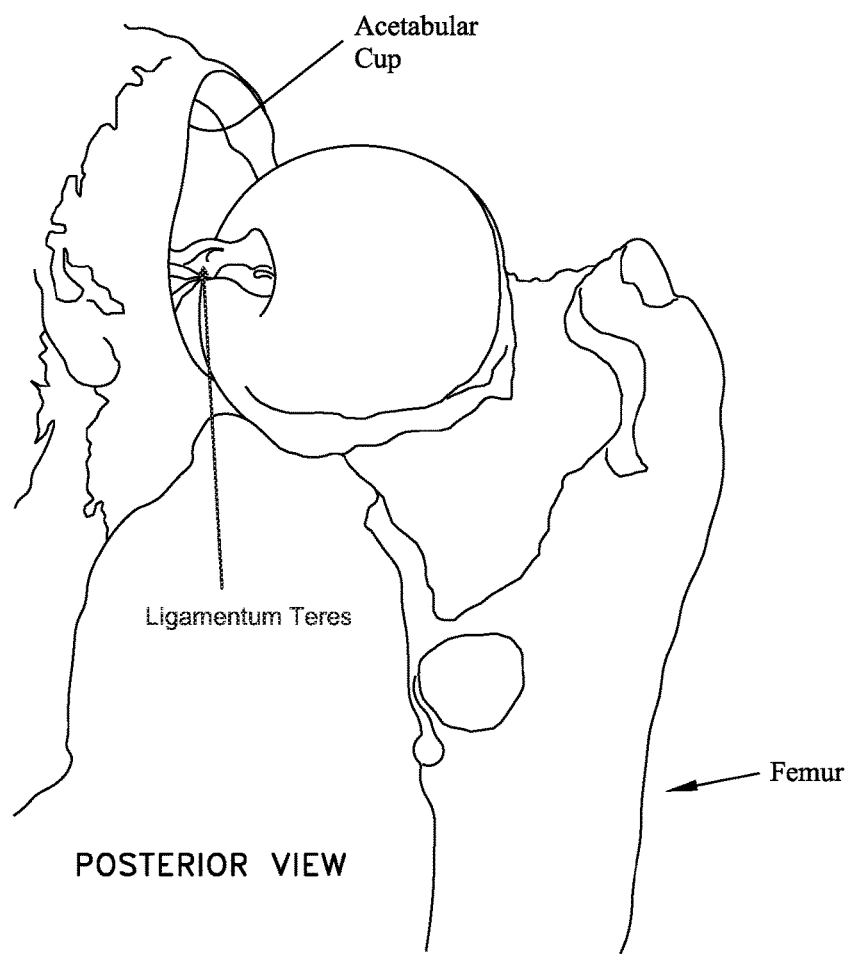
Figure 9:
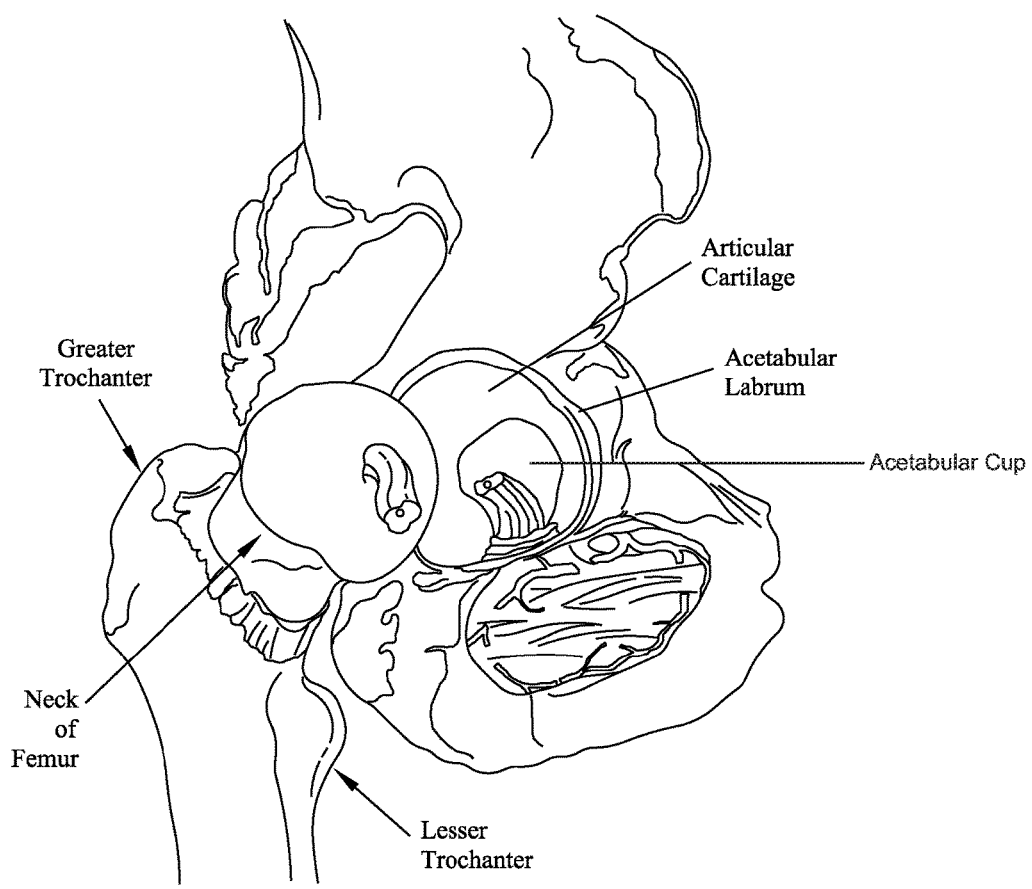
Figure 10:
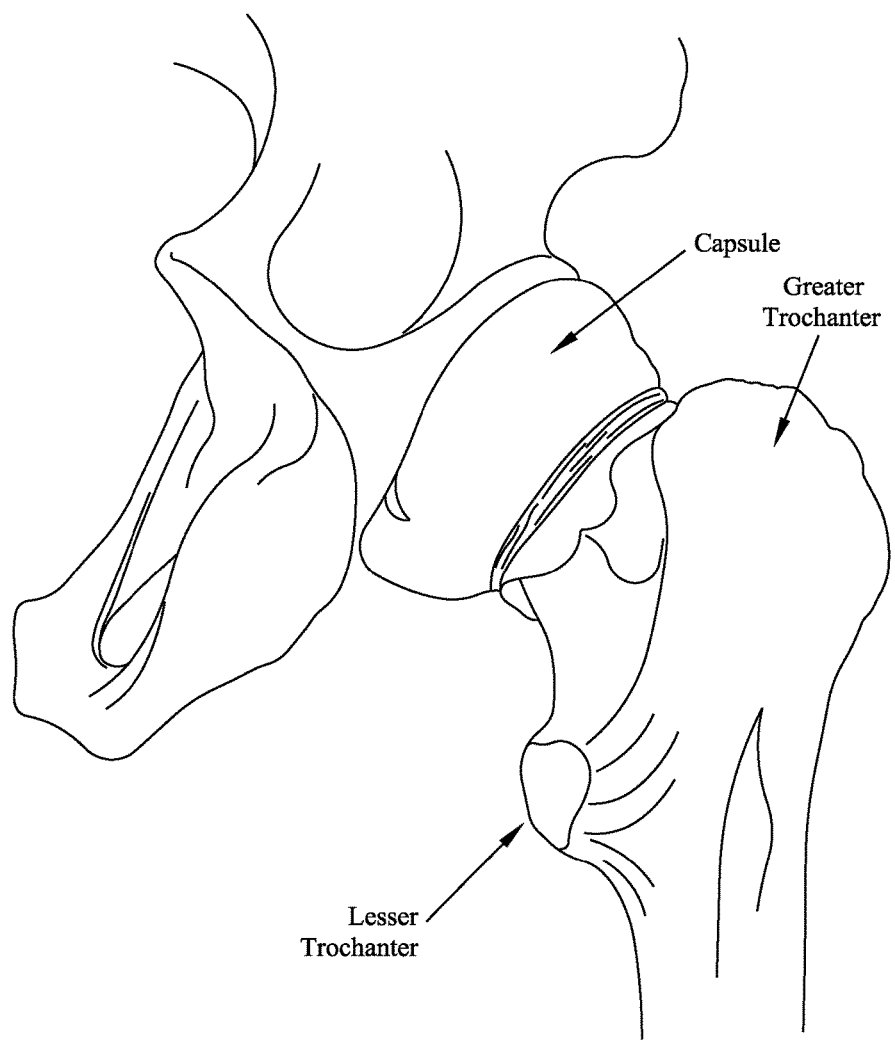
Figure 11:
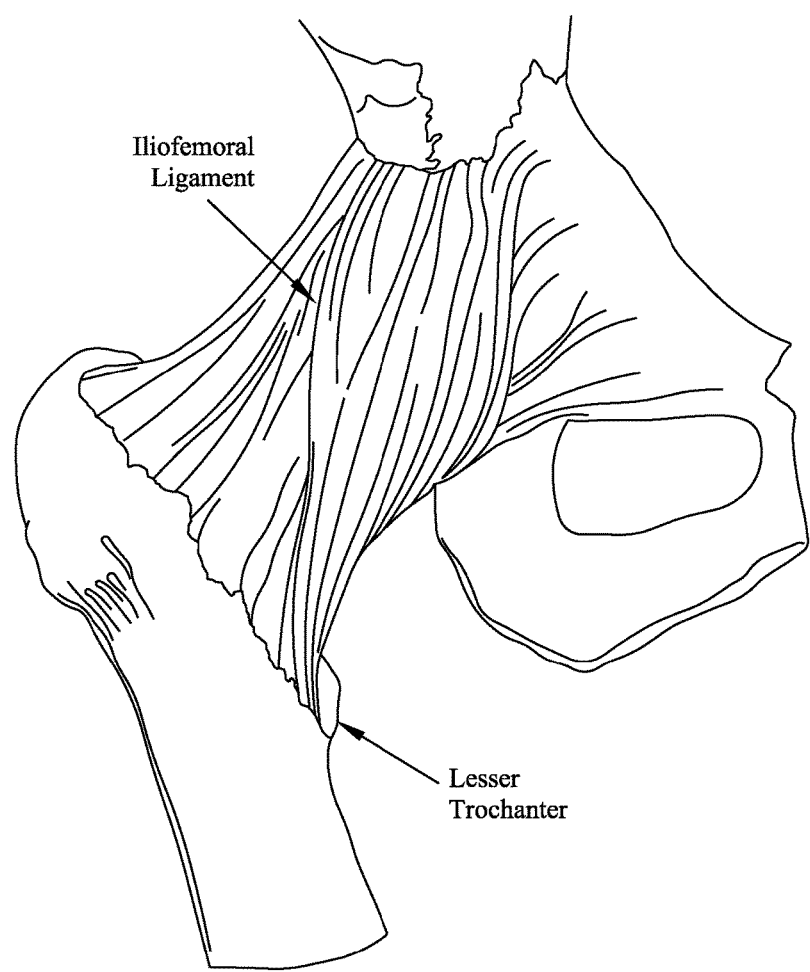
Figure 12:
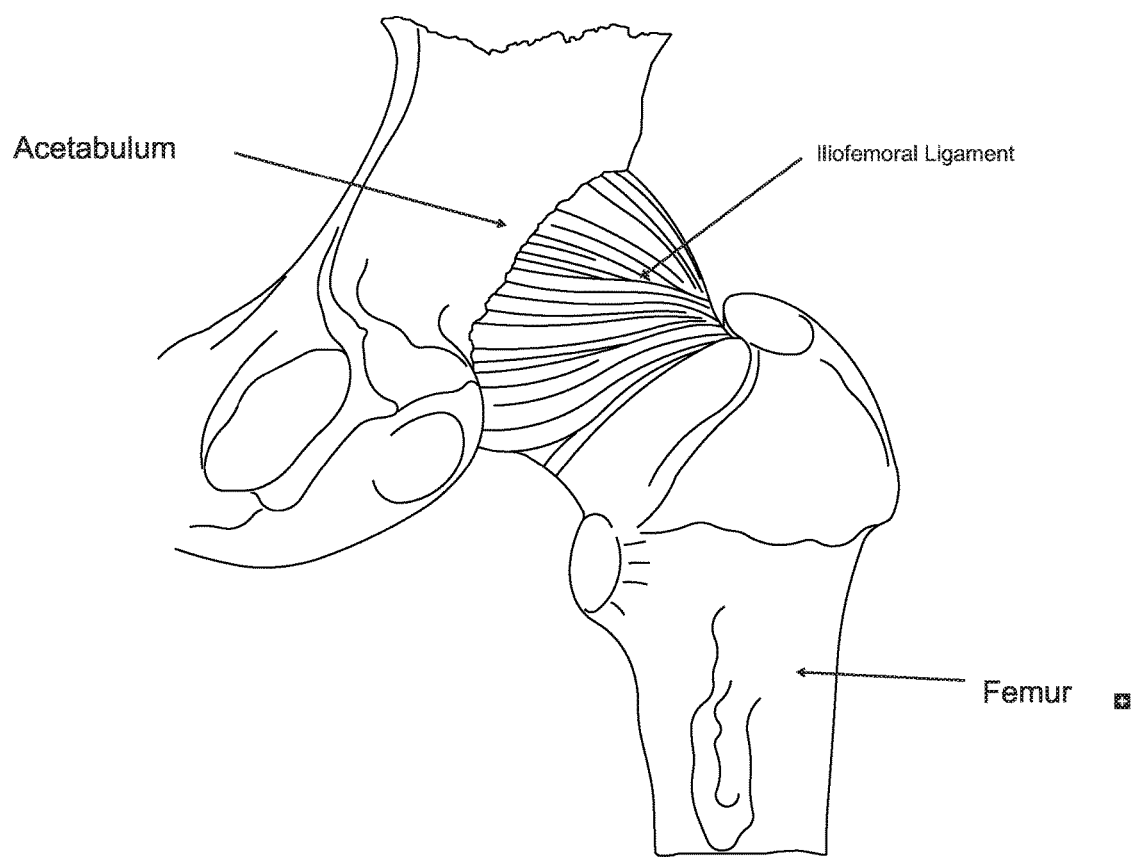
Figure 15:
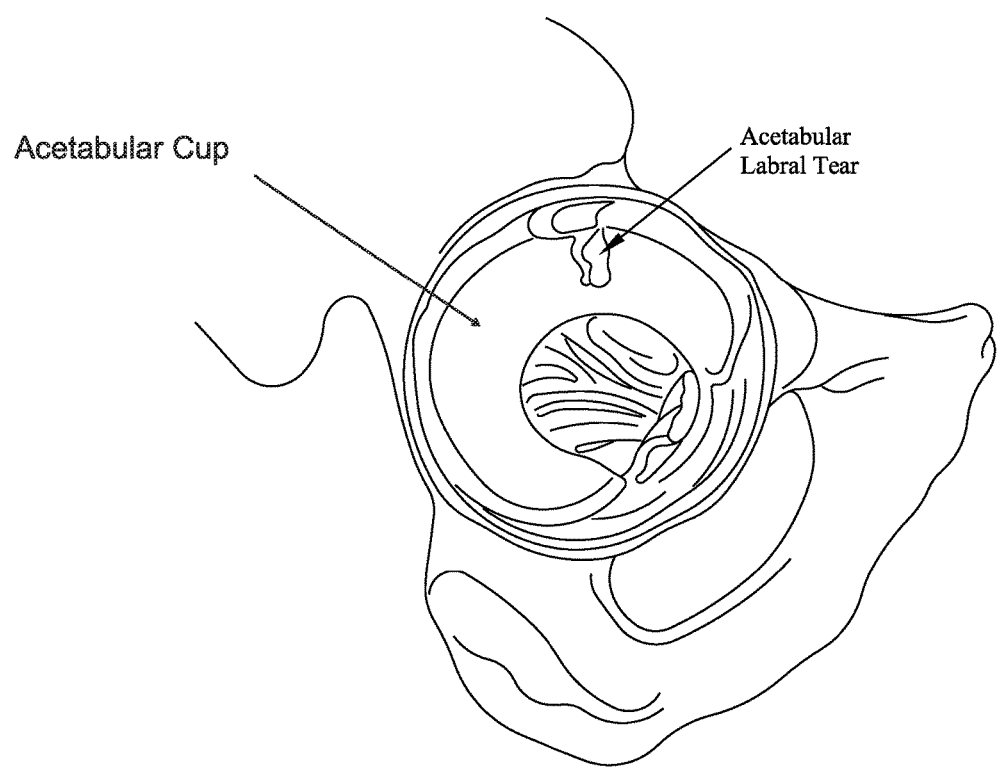
FIG. 15 is a schematic view showing a labral tear.
Figure 16:
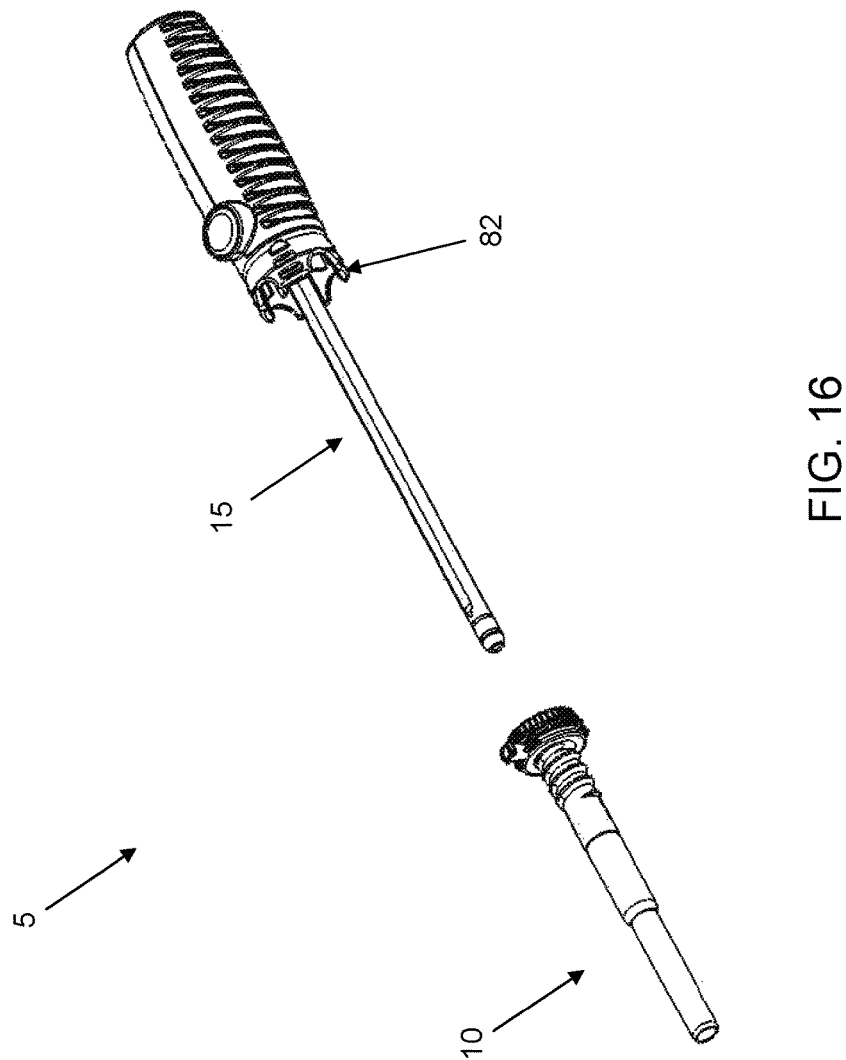
FIGS. 16-25 are schematic views showing a first type of telescoping access cannula formed in accordance with the present invention, as well as a telescoping obturator which may be used in conjunction with the same.
Figure 17:
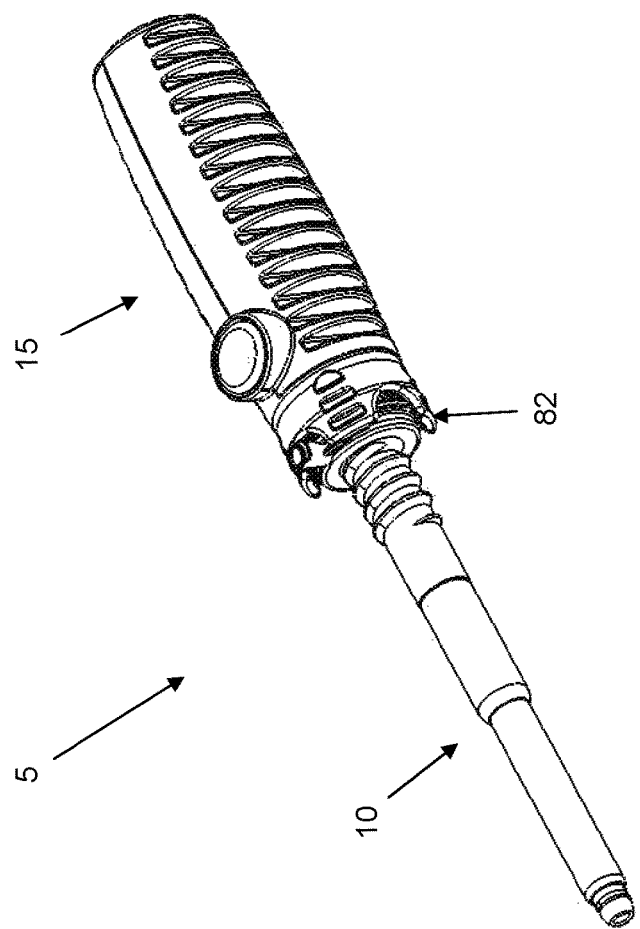
Figure 18:
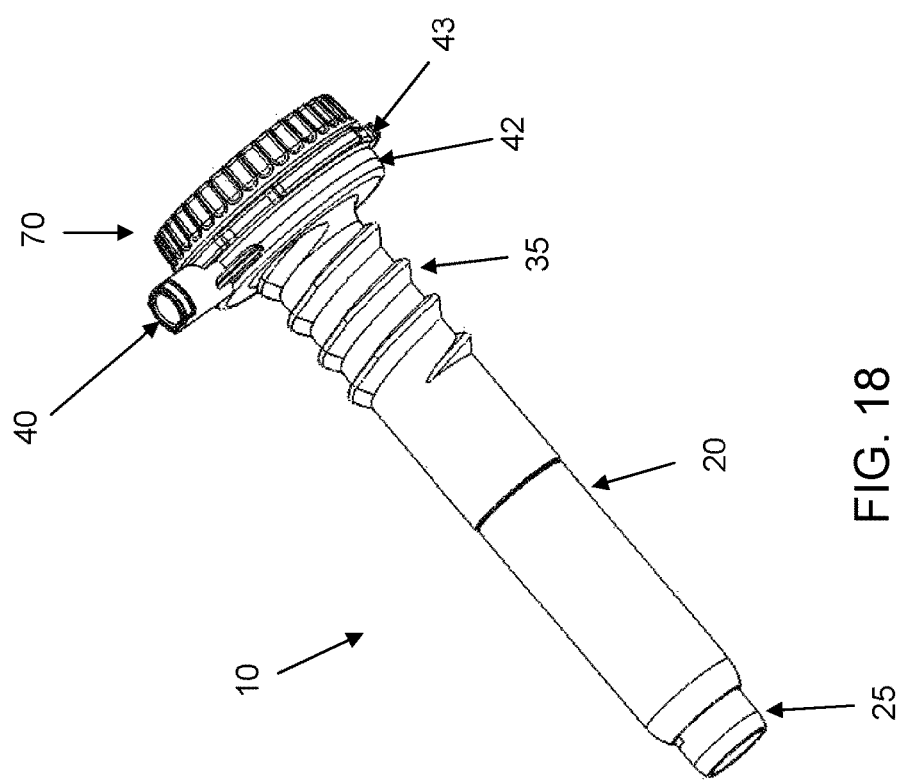
Figure 19:
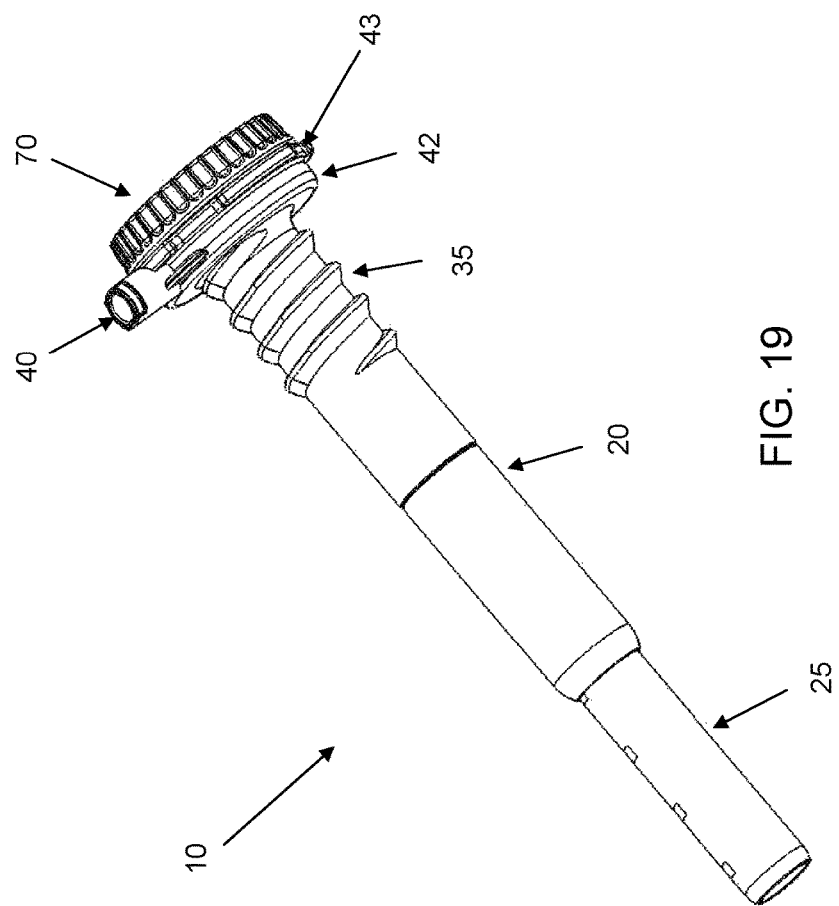

Looking first at FIGS. 16-25, there is shown a telescoping access cannula assembly 5 formed in accordance with the present invention. Telescoping access cannula assembly 5 generally comprises a telescoping access cannula 10 and a telescoping obturator 15.

Telescoping access cannula 10 generally comprises an outer tube 20, an inner tube 25 telescopically disposed within outer tube 20, and a tubular rotatable member 30 for controlling the relative longitudinal disposition of inner tube 25 relative to outer tube 20. Outer tube 20, inner tube 25 and tubular rotatable member 30 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

Outer tube 20 comprises an outer thread 35 (partial, full or multiple thread) for stabilizing outer tube 20 within tissue, an inner thread 37 formed on the interior wall of outer tube 20, a port 40 communicating with the interior of outer tube 20, and a proximal flange 42 including one or more keyways 43.

Inner tube 25 comprises an outer thread 45 (partial, full or multiple thread) formed on the outer surface of inner tube 25, and a finger 50 projecting laterally outwardly from the outer surface of inner tube 25.

Rotatable member 30 comprises a hollow tube 53 having a substantially longitudinal slot 55 formed therein; slot 55 forms an angle of less than 90 degrees to the longitudinal axis of hollow tube 53, and preferably forms an angle of less than 45 degrees to the longitudinal axis of hollow tube 53, and is more preferably substantially aligned with the longitudinal axis of hollow tube 53. Preferably a pair of seals 60, 65 are mounted to the proximal end of rotatable member 30 and captured in place via a hollow rim cap 70. Seals 60, 65 are of the sort well known in the art for passing instruments therethrough while retarding fluid flow therethrough. Cap 70 is assembled onto proximal flange 42 of outer tube 20, but can rotate freely with respect to proximal flange 42 of outer tube 20. Cap 70 has one or more keys 71 which engage counterpart keyways 72 in seals 60, 65 and rotatable member 30 so that all of these components (i.e., cap 70, seals 60, 65 and rotatable member 30) rotate together as a unit. Cap 70 includes one or more keyways 73.

Figure 20:
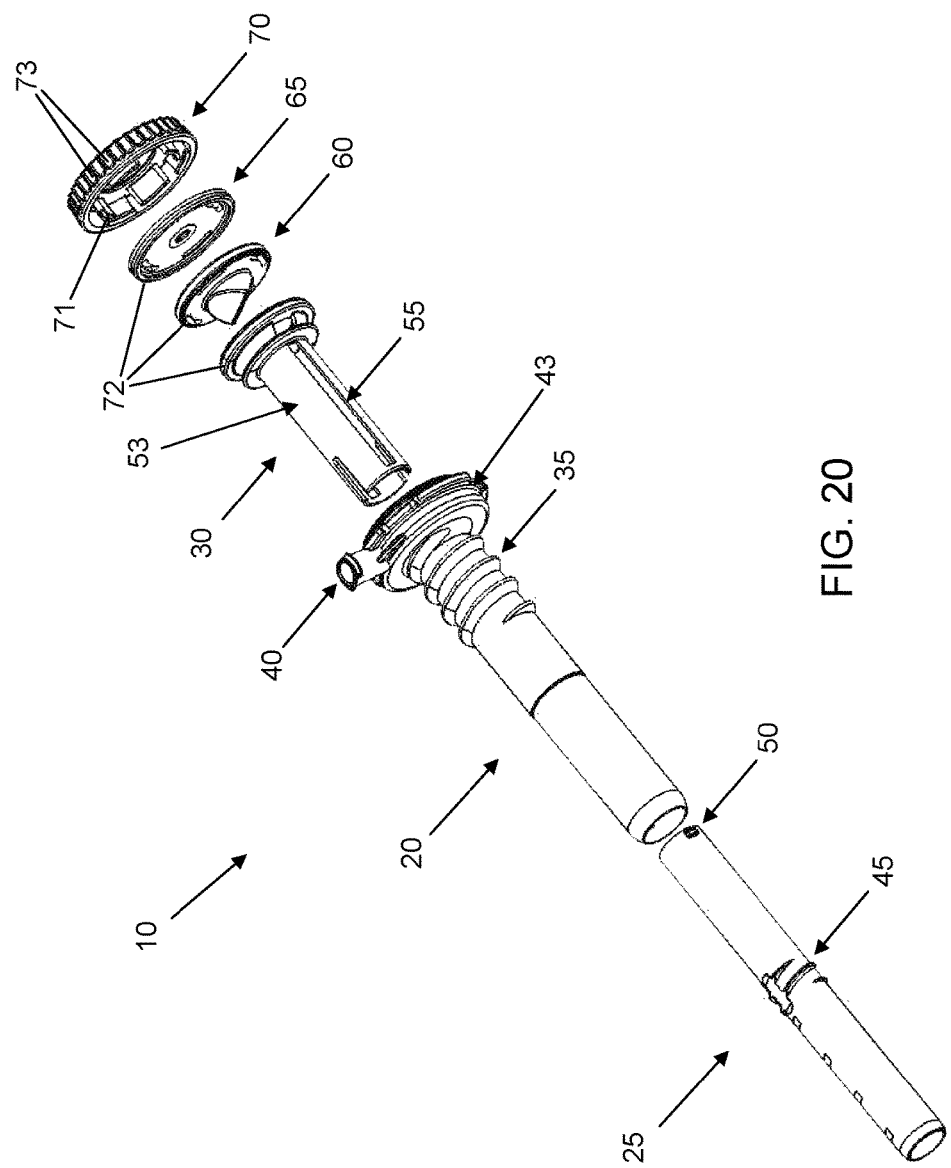
Figure 21:
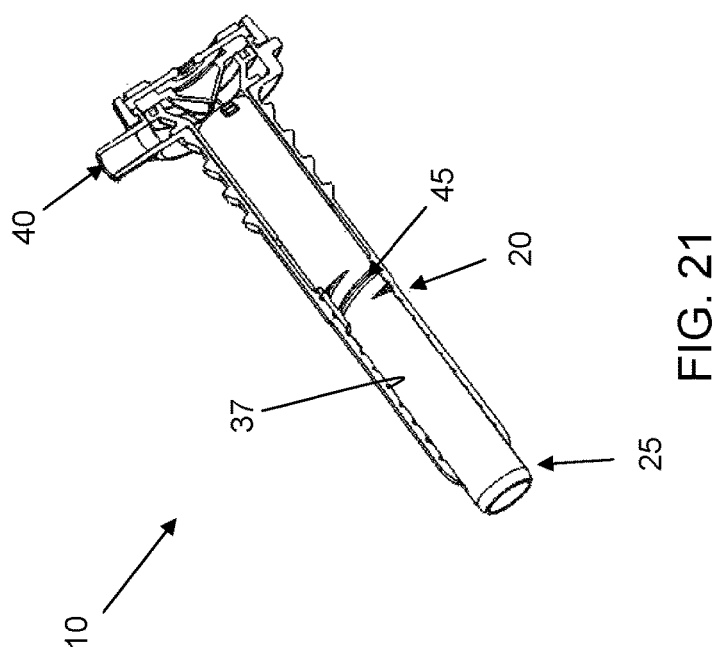
Figure 22:
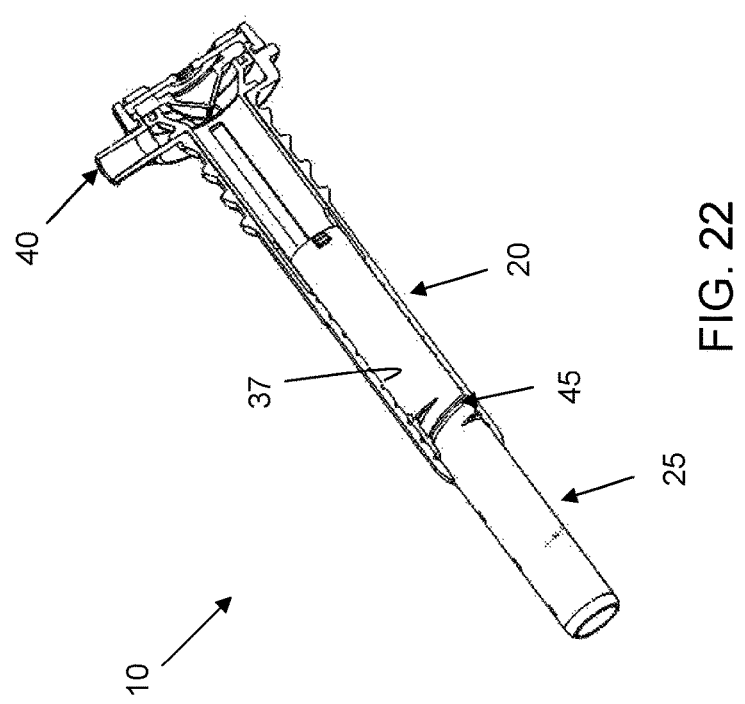
Figure 23:
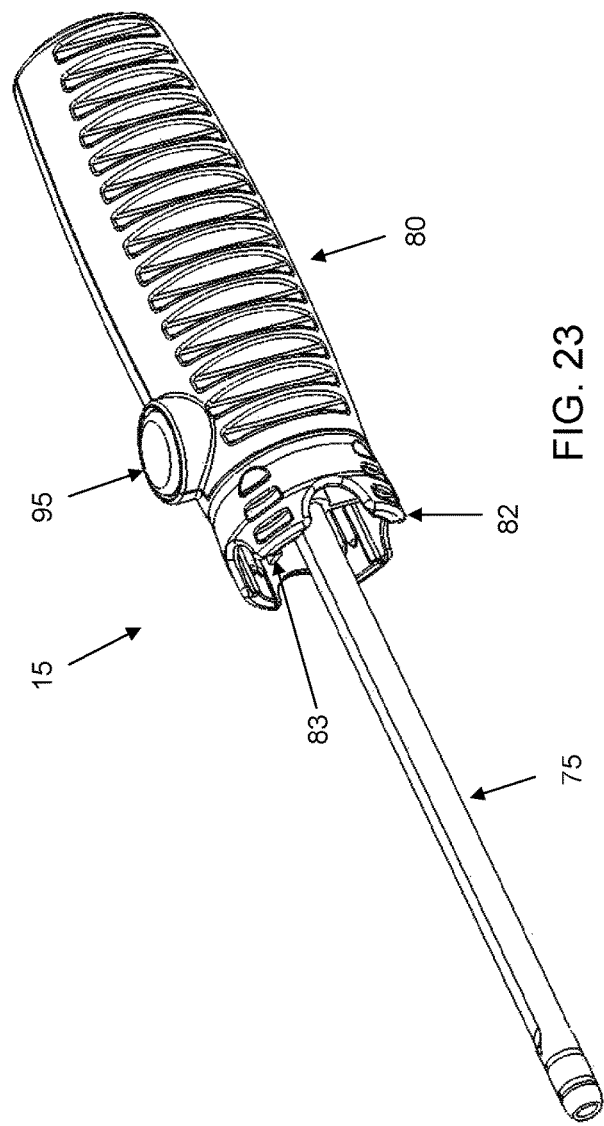
Figure 24:
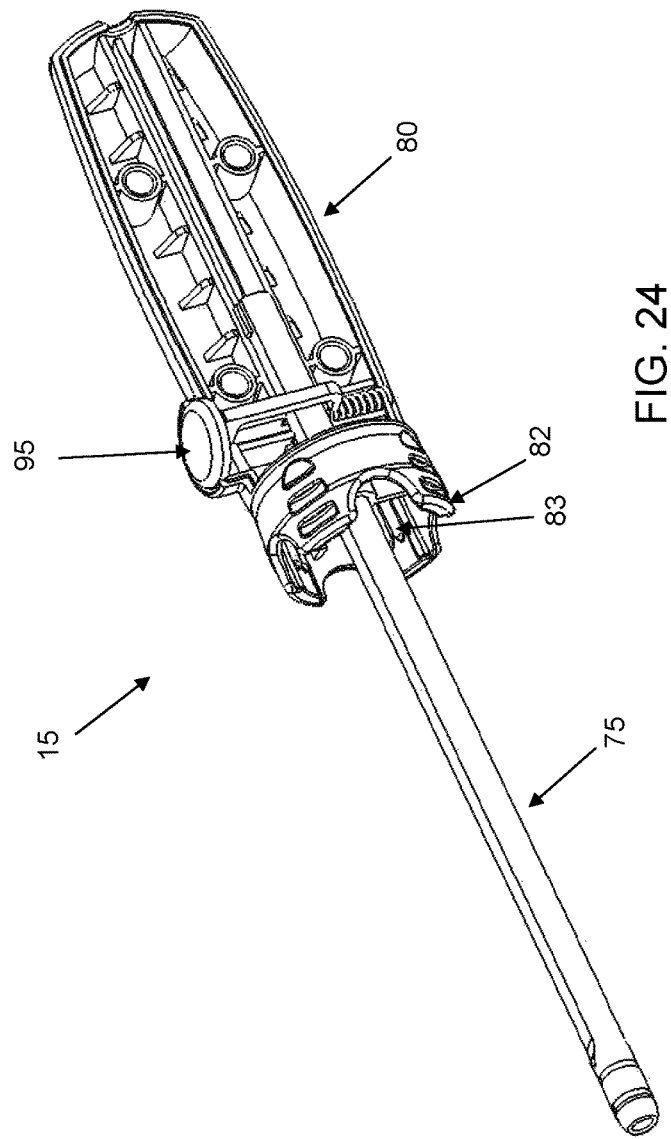

Inner tube 25 is disposed within outer tube 20 such that outer thread 45 of inner tube 25 engages inner thread 37 of outer tube 20, whereby rotation of inner tube 25 relative to outer tube 20 causes longitudinal movement of inner tube 25 relative to outer tube 20. Rotatable member 30 controls the relative longitudinal disposition of inner tube 25 relative to outer tube 20 by providing a means to turn inner tube 25 relative to outer tube 20. More particularly, inner tube 25 and rotatable member 30 are disposed within outer tube 20 such that finger 50 of inner tube 25 is slidably received within slot 55 of rotatable member 30. Slot 55 preferably has closed ends (as shown in FIG. 20) so as to limit movement of inner tube 25 relative to rotatable member 30, but slot 55 can also have an open end if desired. As a result of this construction, when the proximal end of rotatable member 30 is turned (e.g., by turning cap 70), rotatable member 30 will induce a corresponding rotational movement of inner tube 25 relative to outer tube 20, whereby to induce longitudinal movement of inner tube 25 relative to outer tube 20. Thus, by turning rotatable cap 70 in one direction or the other direction relative to outer tube 20, inner tube 25 can be projected out of, or retracted into, outer tube 20.

It will be appreciated that outer tube 20, inner tube 25 and tubular rotatable member 30 are all aligned co-axial with one another, so that their respective lumens collectively form a central lumen for the assembled telescoping access cannula.

Telescoping access cannula 10 can have an inner diameter of between about 1 mm and about 20 mm, but is preferably between about 4 mm and about 15 mm, and more preferably between about 5 mm and about 10 mm. Telescoping access cannula 10 can have a working length—that is, the distance between the underside of proximal flange 42 of outer tube 20 to the distal end of inner tube 25—ranging from about 10 mm to about 300 mm, but is preferably between about 30 mm and about 200 mm. Telescoping access cannula 10 preferably has an adjustable length typically up to approximately 50% of the length of the outer tube 20, but can exceed this as well. Stated another way, telescoping access cannula 10 typically has a working length which can range between (i) the distance between the underside of proximal flange 42 of outer tube 20 and the distal end of outer tube 20, and (ii) approximately 150% of that length, or more.

Outer tube 20, inner tube 25, rotatable member 30 and cap 70, as well as selected other components of telescoping access cannula 10, may be constructed of plastic or metal, but are preferably plastic. Plastic materials include, but are not limited to: nylon, polycarbonate, ABS, acrylic, polyethylene, and polypropylene. The plastic components can be rigid, semi-flexible or flexible. Flexibility can enable one or more portions of the telescoping access cannula 10 to flex within the tissue, thereby enabling improved instrument mobility and/or visualization. The cannula components can be machined or plastic injection molded, as appropriate. The seals 60, 65 can be constructed out of a rubber (e.g., silicone) or a thermoplastic elastomer.

Obturators are blunt instruments which are typically disposed within the central lumens of access cannulas during deployment, in order to prevent tissue coring during cannula insertion. In accordance with the present invention, a telescoping obturator 15 is provided for use with telescoping access cannula 10.

Telescoping obturator 15 generally comprises a shaft 75 and a handle 80. Handle 80 comprises one or more keys 82 for engaging keyways 43 in proximal flange 42 of outer tube 20, whereby handle 80 of telescoping obturator 15 can be used to turn outer tube 20 of telescoping access cannula 10 during introduction through tissue. Additionally, handle 80 of telescoping obturator 15 comprises one or more keys 83 for engaging keyways 73 in cap 70. As noted above, cap 70 is keyed to rotatable member 30 which in turn engages telescoping inner tube 25. Thus, handle 80 is keyed to inner tube 25 as well. On account of the foregoing, since handle 80 keys to both outer tube 20 (via keys 82 and keyways 43) and to inner tube 25 (via keys 83 and keyways 73, cap 70 and rotatable member 30), outer tube 20 cannot rotate relative to the inner tube 25 during introduction of the telescoping access cannula through tissue. This prevents changes in the overall length of the telescoping access cannula during insertion through tissue.

Shaft 75 of telescoping obturator 15 comprises a plurality of openings 85. Openings 85 operate in conjunction with a release mechanism 90 carried on handle 80 which is used to adjust how much of shaft 75 extends out of handle 80. More particularly, release mechanism 90 comprises a button 95 which moves a finger 96 against the action of a spring 97. By depressing button 95, finger 96 can be disengaged from an opening 85 in shaft 75, thereby allowing shaft 75 to be moved further in or out of handle 80. Conversely, releasing button 95 allows finger 96 to seat in an opening 85 in shaft 75, whereby to lock shaft 75 in position relative to handle 80.

If desired, telescoping obturator 15 can be cannulated, such that telescoping obturator 15 (and telescoping access cannula 10) can be delivered over a guidewire, switching stick and/or other instrument.

Figure 25:
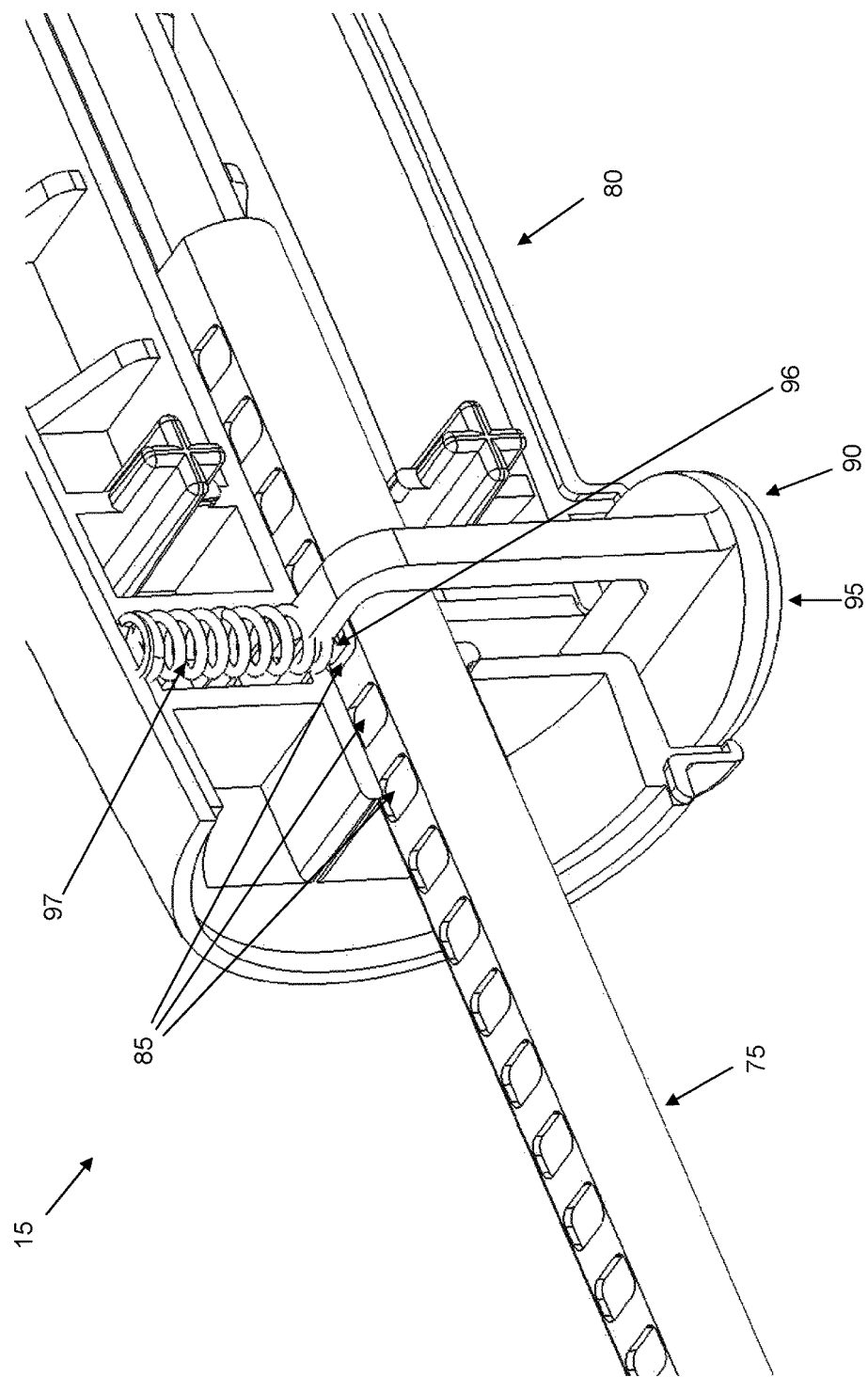
Figure 25A:
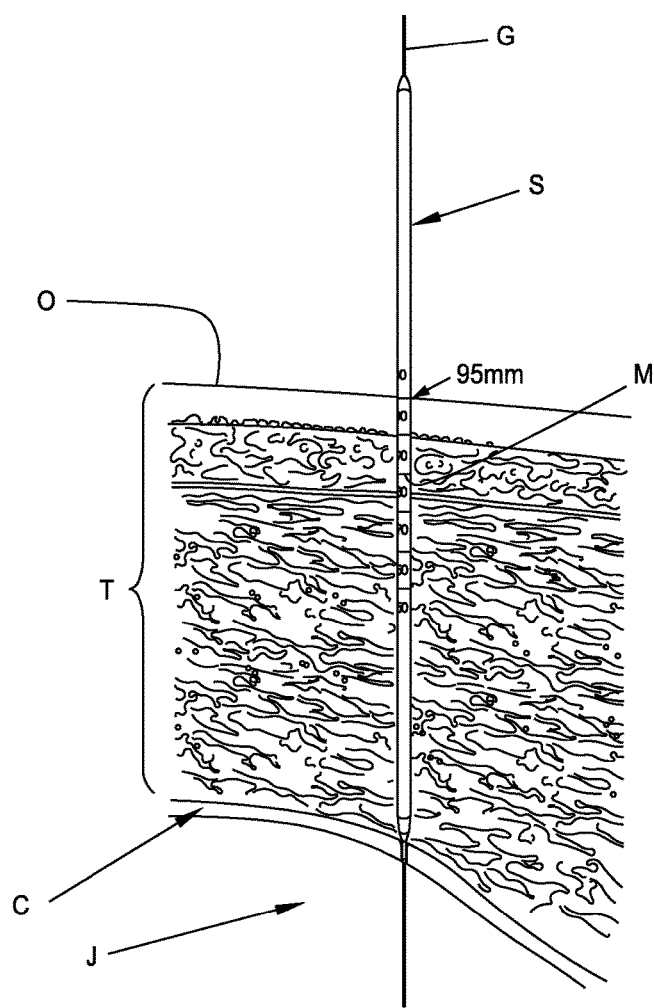

In use, and looking now at FIG. 25A, a guidewire G is preferably first passed from the outer surface of the skin O, down through the intervening tissue T, through capsule C and into the interior of the joint J. Then a switching stick S, having length markers M formed thereon, is inserted over guidewire G, so that switching stick S extends from the outer surface of the skin O down through the intervening tissue T to the capsule C. Then guidewire G is preferably removed from the surgical site, leaving switching stick S in place. Using length markers M on switching stick S, the distance from the capsule C to the outer surface of the skin O is measured. This measurement can assist in properly sizing the telescoping access cannula so as to optimize its use with the unique anatomy of the patient.

More particularly, using this measurement of the distance from the outer surface of the skin O down to the capsule C, telescoping access cannula 10 is set to a desired insertion length, e.g., by turning cap 70 so as to adjust the degree to which inner tube 25 extends out of outer tube 20. Then telescoping obturator 15 is disposed within telescoping access cannula 10 so that the blunt distal tip of shaft 75 of telescoping obturator 15 extends out of the distal end of inner tube 25 of telescoping access cannula 10, and so that keys 82 and 83 seat in keyways 43 and 73, respectively. Then telescoping obturator 15 is set to a corresponding length, e.g., by depressing button 95 and adjusting the extent to which shaft 75 extends out of handle 80.

Figure 25B:
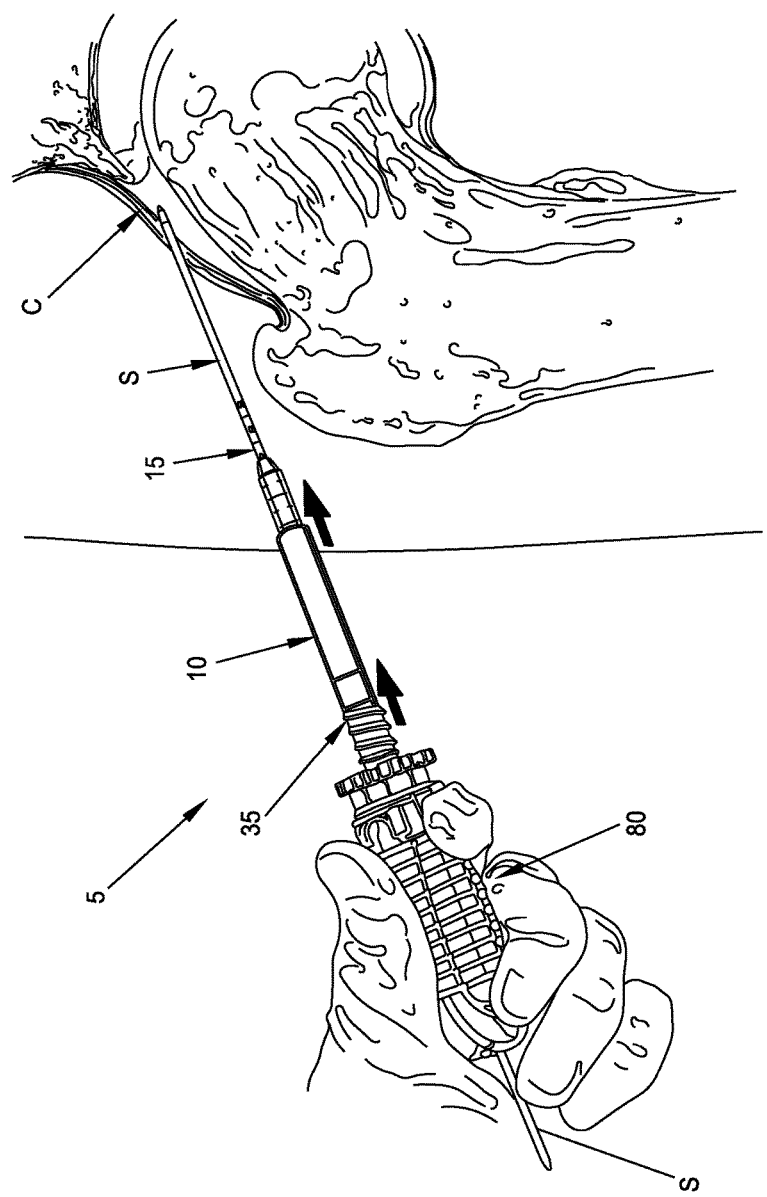
Figure 25C:
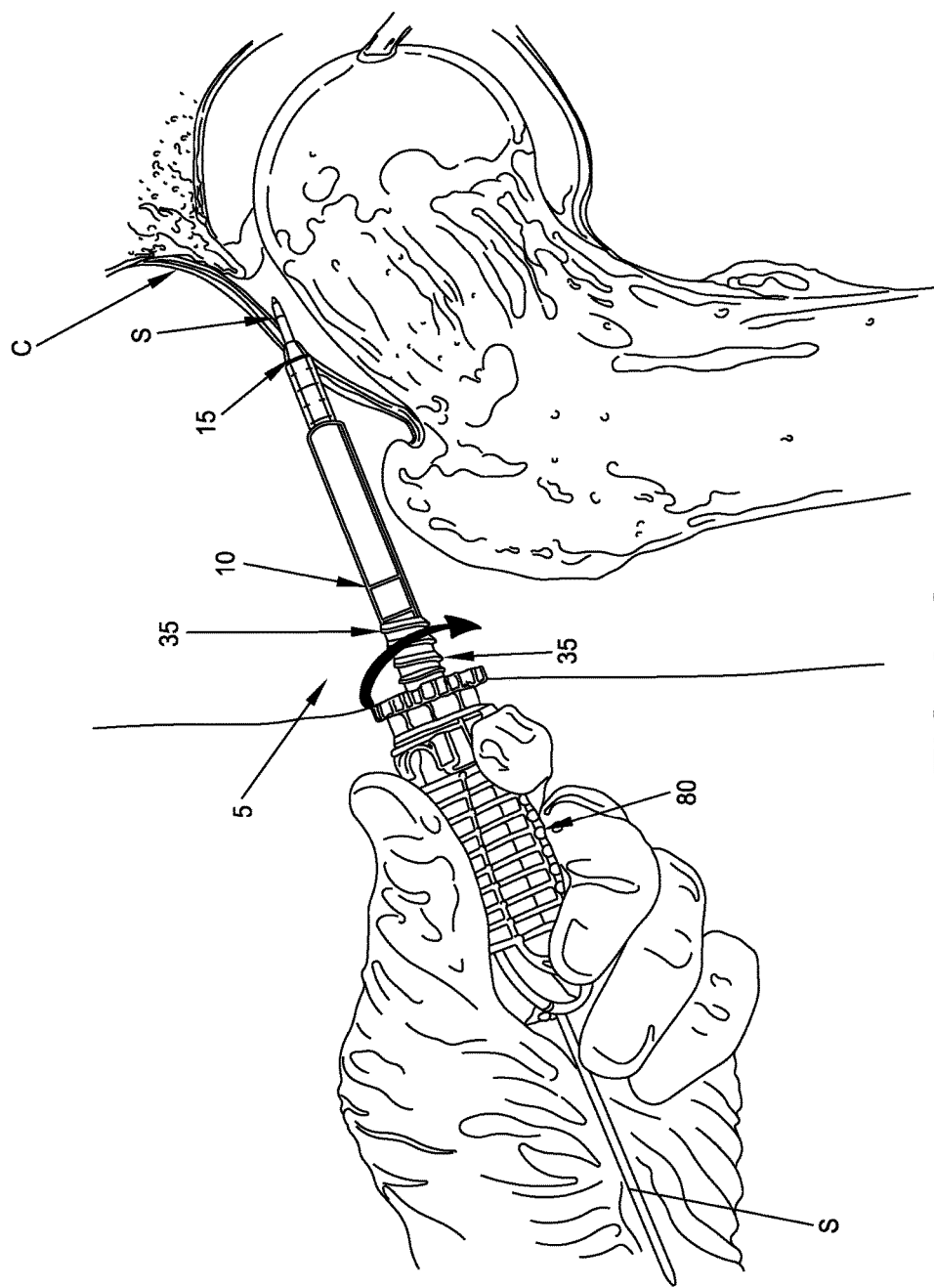

Next, and looking now at FIGS. 25B and 25C, telescoping obturator 15 is used to insert telescoping access cannula 10 into the tissue, e.g., by simultaneously pushing and turning handle 80 so as to turn outer thread 35 of outer tube 20 into the tissue. It will be appreciated that as this occurs, the engagement of keys 82 and 83 in keyways 43 and 73, respectively, keep outer tube 20 and inner tube 25 from moving relative to one another. Cannula advancement is preferably continued until proximal flange 42 of outer tube 20 settles against the outer surface of the skin. Then switching stick S and telescoping obturator 15 are removed from telescoping access cannula 10. See FIGS. 25D and 25E.

At this point the overall length of the telescoping access cannula may be further adjusted as desired by turning cap 70, whereby to move inner tube 25 relative to outer tube 20. This action causes the distal end of inner tube 25 to extend, or retract, relative to outer tube 20, while leaving outer tube 20 stationary relative to the tissue, whereby to minimize trauma to the tissue. Thereafter, telescoping access cannula 10 may be used as a corridor for accessing the interior of the hip joint, by passing instrumentation (e.g., arthroscopes, surgical instruments, etc.) through the central lumen of the telescoping access cannula, whereby to reach a remote surgical site within the joint.

Significantly, if it should subsequently be desired to modify the length of telescoping access cannula 10 in situ, during the procedure, this may be safely and conveniently done, by simply rotating cap 70, whereby to adjust the disposition of the distal end of inner tube 25 relative to outer tube 20. Again, this occurs without changing the position of outer tube 20 relative to the tissue.

Significantly, the length of telescoping access cannula 10 may be adjusted multiple times during a surgical procedure. For example, the user may desire that the distal end of the telescoping access cannula be retracted, or moved in a proximal direction, but without moving outer tube 20. This could, for example, enable improved mobility of an instrument that is subsequently inserted through the cannula. Additionally, this could be performed because the distance from the outer surface of the skin to a location within the joint has changed during the course of the surgical procedure, e.g., due to tissue swelling—in this case, changing the overall length of the telescoping access cannula enables the distal end of the cannula to remain at the same location.

Figure 26:
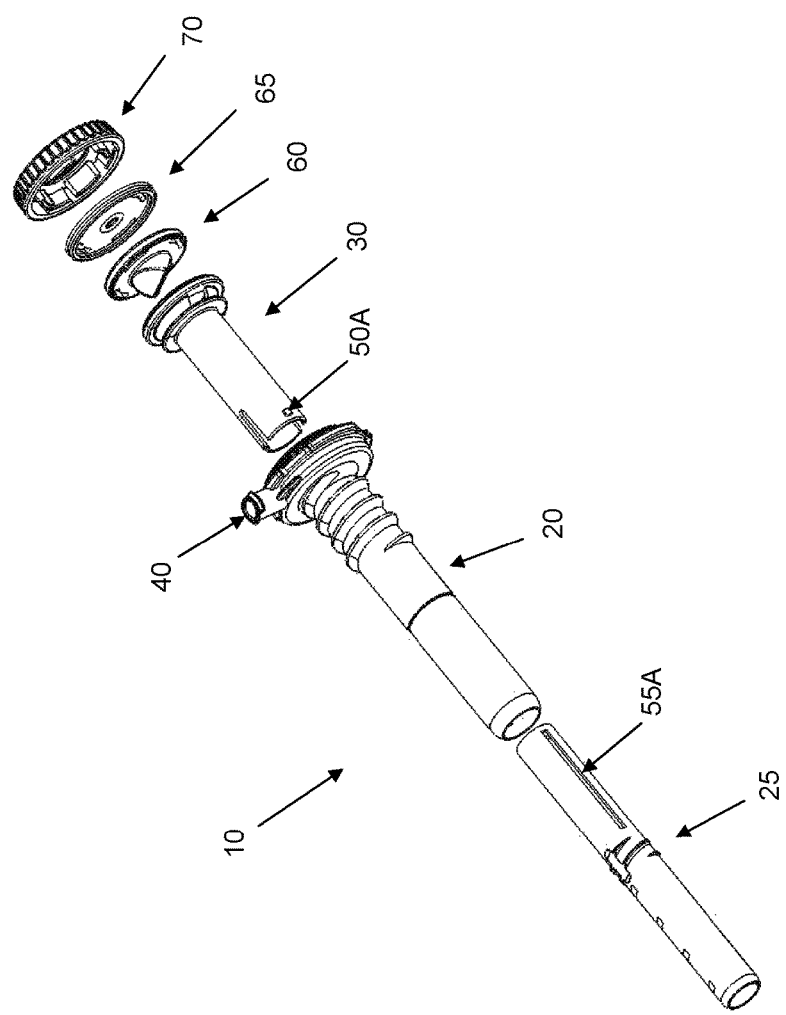
FIG. 26 is a schematic view showing a modified form of the first type of telescoping access cannula of FIGS. 16-25.

Looking next at FIG. 26, there is shown a related construction for telescoping access cannula 10. More particularly, the telescoping access cannula shown in FIG. 26 is preferably substantially identical to the telescoping access cannula shown in FIGS. 16-22, except that in this form of the invention, the finger 50A is formed on rotatable member 30 and the longitudinal slot 55A is formed in inner tube 25—finger 50A rides in longitudinal slot 55A so as to transmit rotary motion from rotatable member 30 to inner tube 25.

Second Type of Telescoping Access Cannula

Figure 27:
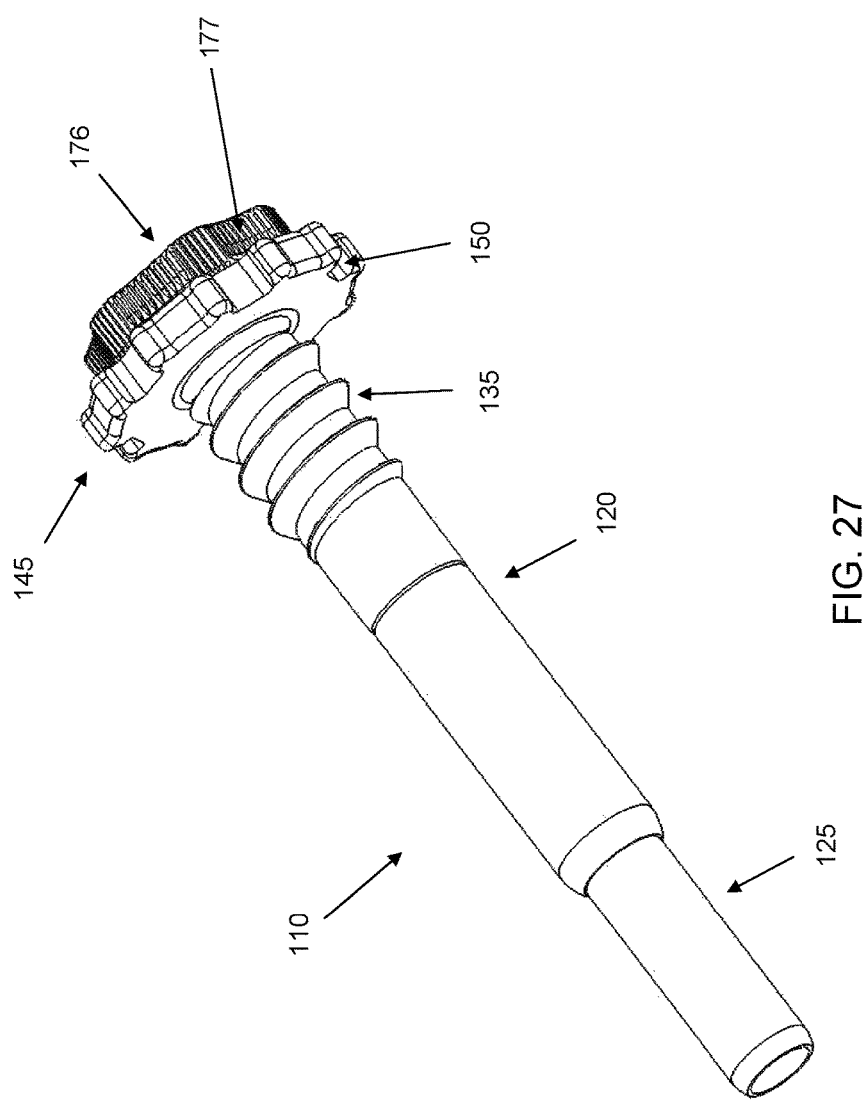
FIGS. 27-29 are schematic views showing a second type of telescoping access cannula formed in accordance with the present invention.
Figure 28:
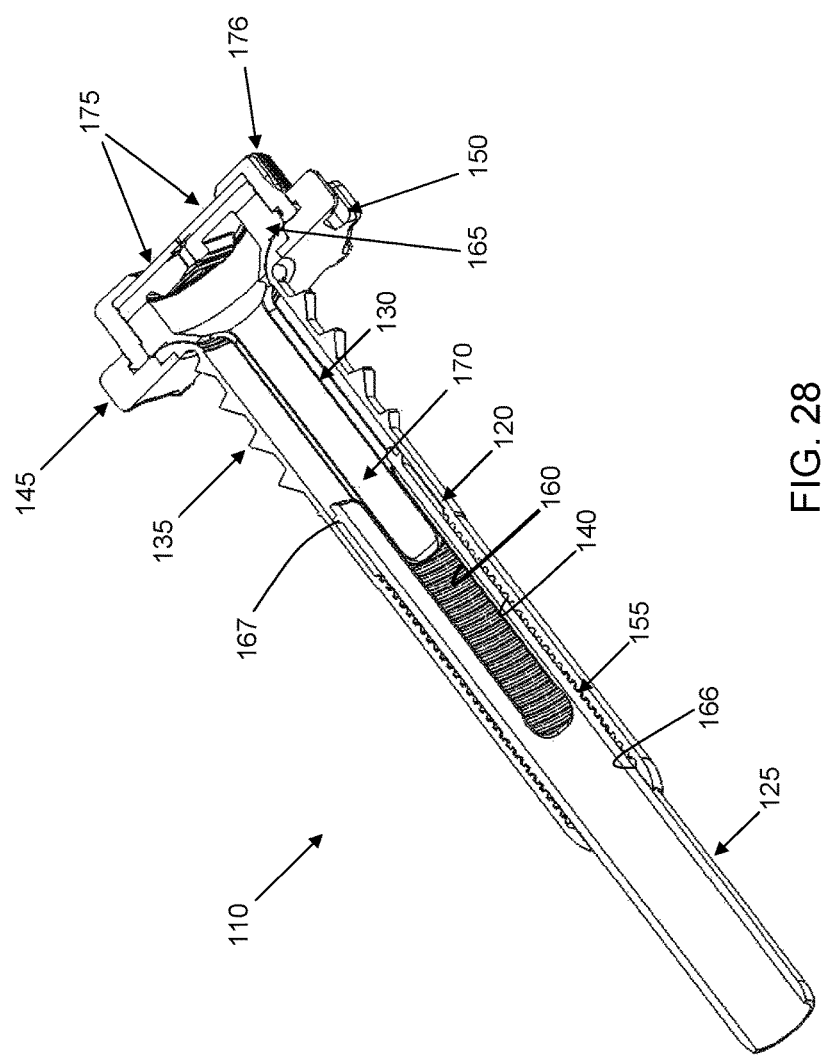

In another form of the invention, a spline connection may be used to transfer rotational motion from a keyed driver (i.e., the rotatable member discussed above) to the telescoping inner tube. More particularly, and looking now at FIGS. 27 and 28, there is shown another novel telescoping access cannula 110 formed in accordance with the present invention. Telescoping access cannula 110 generally comprises a tubular stationary body 120 (i.e., the aforementioned outer tube) for seating in the patient's tissue, a telescoping inner tube 125 for adjustable positioning relative to stationary body 120, and a tubular keyed driver 130 for turning telescoping inner tube 125 relative to stationary body 120, whereby to adjustably position telescoping inner tube 125 relative to stationary body 120. Tubular stationary body 120, telescoping inner tube 125 and tubular keyed driver 130 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, stationary body 120 generally comprises a tube-like structure having securement threads 135 formed on its outer surface and translation threads 140 formed on its inner surface. Although shown on the proximal end of stationary body 120, securement threads 135 can be located at the distal or middle portions of stationary body 120, or alternatively along the entire length of stationary body 120. Alternatively, inner tube 125 can comprise securement threads (e.g., on its distal end, where it is safely clear of stationary body 120). The proximal portion of stationary body 120 preferably comprises a flange 145. Flange 145 preferably comprises one or more keyways 150 (FIG. 28) for selectively receiving the one or more keys 82 of telescoping obturator 15, as will hereinafter be discussed in further detail.

Telescoping inner tube 125 generally comprises a tube-like structure sized to be slidably received in stationary body 120 and having translation threads 155 formed on its outer surface and at least one, and preferably a plurality of, slots 160 formed on its proximal end. Translation threads 155 of telescoping inner tube 125 engage translation threads 140 of stationary body 120, such that rotation of telescoping inner tube 125 relative to stationary body 120 causes longitudinal movement of telescoping inner tube 125 relative to stationary body 120. Translation threads 155 of telescoping inner tube 125 can be a portion of a thread, a full thread or a plurality of threads. A stop 167 near or at the proximal end of telescoping inner tube 125 engages a corresponding stop 166 at or near the distal end of the stationary body 120 so as to limit the extent of distal movement of the telescoping inner tube 125 vis-à-vis stationary body 120.

Keyed driver 130 generally comprises a short tubular head 165 rotatably mounted to stationary body 120 and having at least one, and preferably a plurality of, fingers 170 extending distally therefrom. Fingers 170 of keyed driver 130 engages slots 160 of telescoping inner tube 125, such that rotational motion imparted to keyed driver 130 can be transferred to telescoping inner tube 125 via fingers 170 and slots 160. The fingers 170 and slots 160 thus function as a spline-type mechanism.

It will be appreciated that tubular stationary body 120, telescoping inner tube 125 and tubular keyed driver 130 are all aligned co-axial with one another, so that their respective lumens collectively form a central lumen for the assembled telescoping access cannula.

One or more instrument-passing seals 175 are preferably disposed in tubular head 165. A hollow rim cap 176 captures seals 175 to tubular head 165, and one or more keyways 177 (FIG. 27) are formed in cap 176 for selectively receiving keys 83 of telescoping obturator 15, as will hereinafter be discussed in further detail. Cap 176 is rotatable relative to flange 145 of stationary body 120, but fixed relative to keyed driver 130, such that rotation of cap 176 will turn keyed driver 130 relative to stationary body 120.

Stationary body 120, telescoping inner tube 125, keyed driver 130 and cap 176 are assembled together in the manner shown so as to together constitute the complete telescoping access cannula 110. It will be appreciated that, on account of the foregoing construction, rotational motion imparted to cap 176 will be transferred to keyed driver 130, and thereafter to telescoping inner tube 125 via fingers 170 and slots 160, such that the longitudinal position of telescoping inner tube 125 can be adjusted vis-à-vis stationary body 120 simply by rotating cap 176.

In one embodiment, telescoping obturator 15 can be connected to stationary body 120 and cap 176 (e.g., with keys 82 of telescoping obturator 15 received in keyways 150 of stationary body 120 and with keys 83 of telescoping obturator 15 received in keyways 177 of cap 176) so that as telescoping access cannula 110 is twisted and turned by telescoping obturator 15 during introduction through tissue, telescoping inner tube 125 and stationary body 120 do not rotate relative to each other and the overall length of the telescoping access cannula remains constant.

In use, cap 176 is first rotated so as to position telescoping inner tube 125 in the desired longitudinal position relative to stationary body 120, and then telescoping obturator 15 is inserted within telescoping access cannula 110 so that the distal end of telescoping obturator 15 extends out the distal end of telescoping access cannula 10, and so that the one or more keys 82 of telescoping obturator 15 engage the one or more keyways 150 of stationary body 120 and so that the one or more keys 83 of telescoping obturator 15 engage the one or more keyways 177 of cap 176. Then telescoping obturator 15 is used to advance telescoping access cannula 110 through the anatomy (e.g., over a switching stick) until the distal end of the telescoping cannula is disposed at the joint and flange 145 of stationary body 120 lies against the outer surface of the skin. In practice, the user may chose to initially position the distal end of the telescoping access cannula just adjacent to the joint, or just within the joint; the user may also chose to position the flange 145 of stationary body 120 somewhat offset from the top surface of the skin. As this is done, telescoping obturator 15 may be used to turn telescoping access cannula 110 via keys 82 and keyways 150, and keys 83 and keyways 177, so that securement threads 135 of stationary body 120 are turned into the tissue. If desired, and as noted above, this cannula deployment may be conducted over a guidewire, switching stick and/or other instrumentation. Thereafter, telescoping obturator 15 may be removed, and then keyed driver 130 turned via cap 176 as desired so as to adjust the position of telescoping inner tube 125 relative to stationary body 120, whereby to set the position of the distal end of telescoping inner tube 125 relative to stationary body 120 and hence relative to the anatomy. The telescoping access cannula may then be used as a corridor for accessing the interior of the hip joint, by passing instrumentation (e.g., arthroscopes, surgical instruments, etc.) through the central lumen of the telescoping access cannula whereby to reach a remote site within the joint.

Significantly, due to the construction of the telescoping access cannula, the overall length of the telescoping access cannula may be adjusted either before deployment in the body or after deployment in the body, or both.

Figure 29:
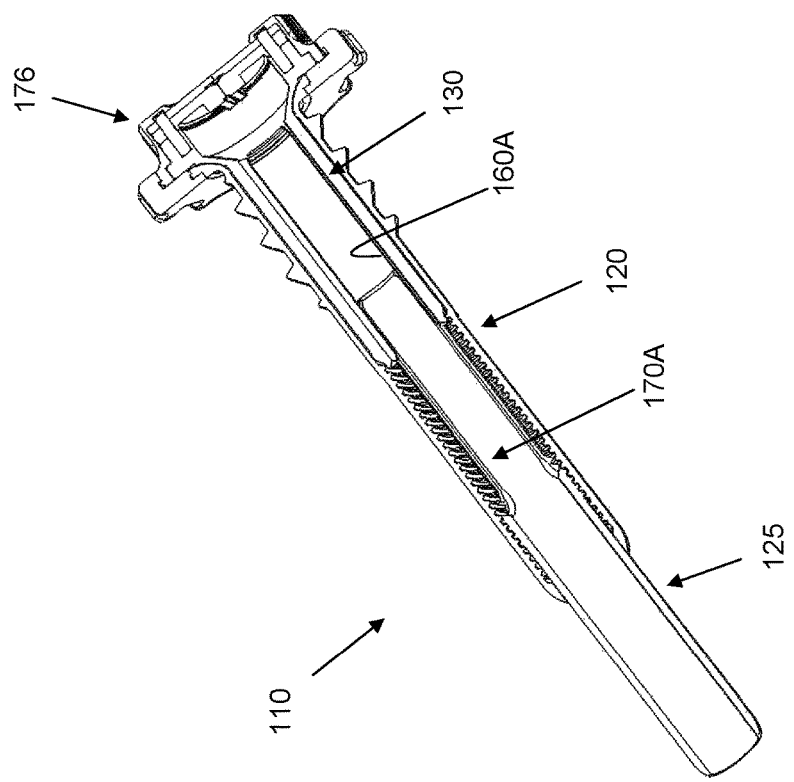
Figure 30:
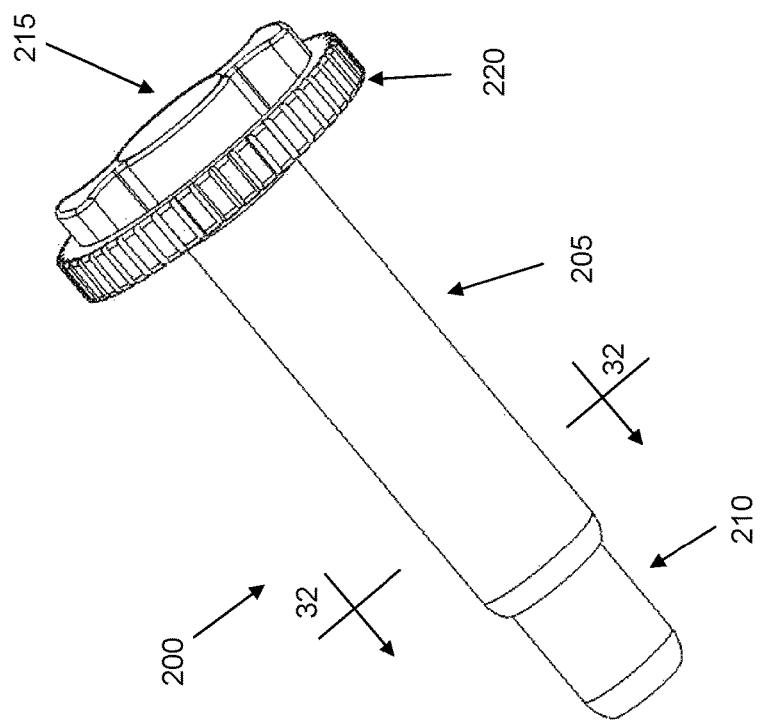
FIGS. 30-41 are schematic views showing a third type of telescoping access cannula formed in accordance with the present invention, with FIG. 32 being a sectional view taken along line 32-32 of FIG. 30.
Figure 31:
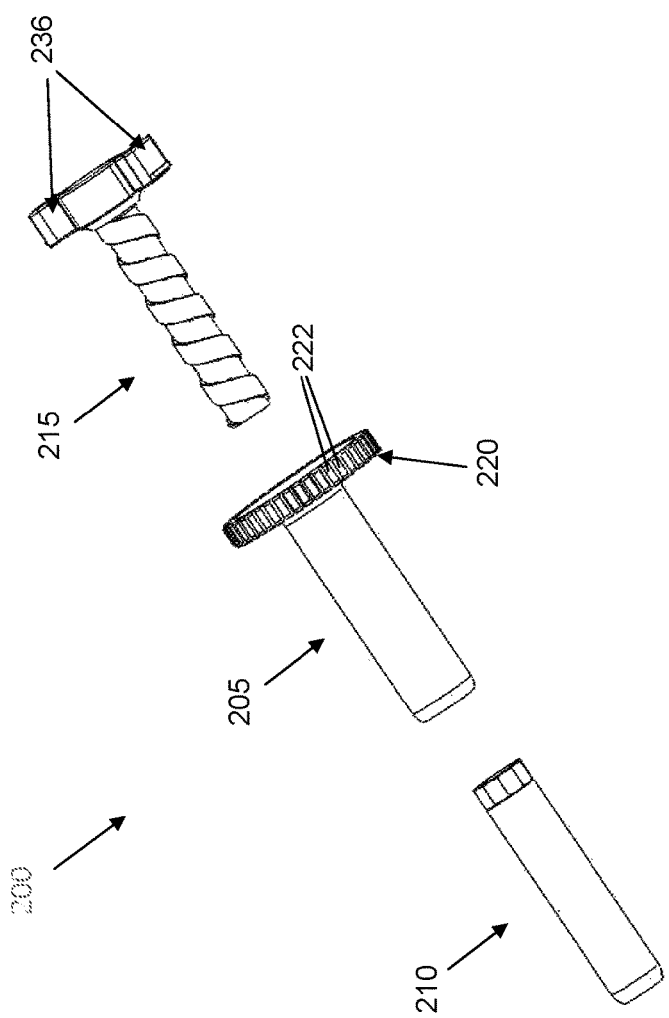

Looking next at FIG. 29, there is shown a related construction for telescoping access cannula 110. More particularly, the telescoping access cannula shown in FIG. 29 is preferably substantially identical to the telescoping access cannula shown in FIGS. 27 and 28, except that in this form of the invention, the slots 160A are formed on keyed driver 130 and the fingers 170A are formed on telescoping inner tube 125. As mentioned above, a plurality of fingers and slots is preferable, although just one finger and just one slot may be provided if desired.

Third Type of Telescoping Access Cannula

In another form of the invention, a screw thread may be used to transfer rotational motion from a rotatable member to the telescoping inner tube.

More particularly, and looking now at FIGS. 30-35, there is shown a novel telescoping access cannula 200 formed in accordance with the present invention. Telescoping access cannula 200 generally comprises a tubular stationary body 205 for seating in the patient's tissue, a telescoping inner tube 210 for adjustable positioning relative to stationary body 205, and a tubular threaded driver 215 for turning telescoping inner tube 210 relative to stationary body 205, whereby to adjustably position telescoping inner tube 210 relative to stationary body 205. Tubular stationary body 205, telescoping inner tube 210 and tubular threaded driver 215 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, stationary body 205 generally comprises a tube-like structure. The proximal portion of stationary body 205 preferably comprises a flange 220 having keyways 222 for receiving the aforementioned keys 82 of telescoping obturator 15. If desired, securement threads (not shown) may be disposed on the outer surface of stationary body 205. The inner lumen of stationary body 205 is preferably formed with a hexagonal cross-section.

Figure 32:
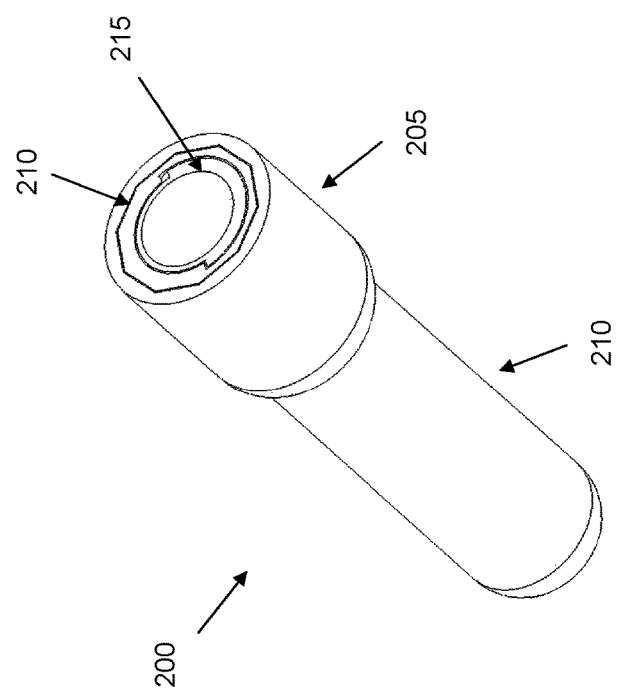
Figure 33:
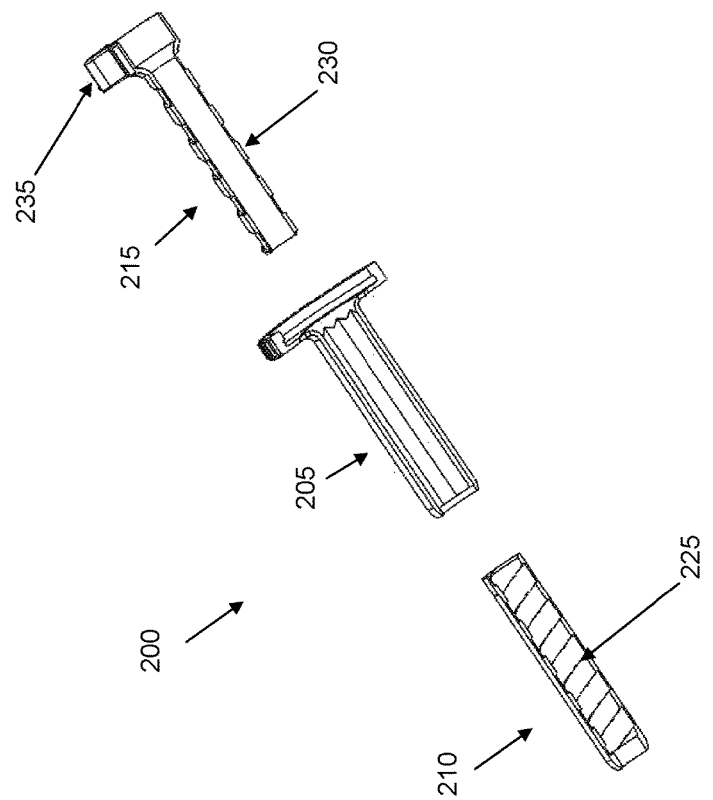
Figure 34:
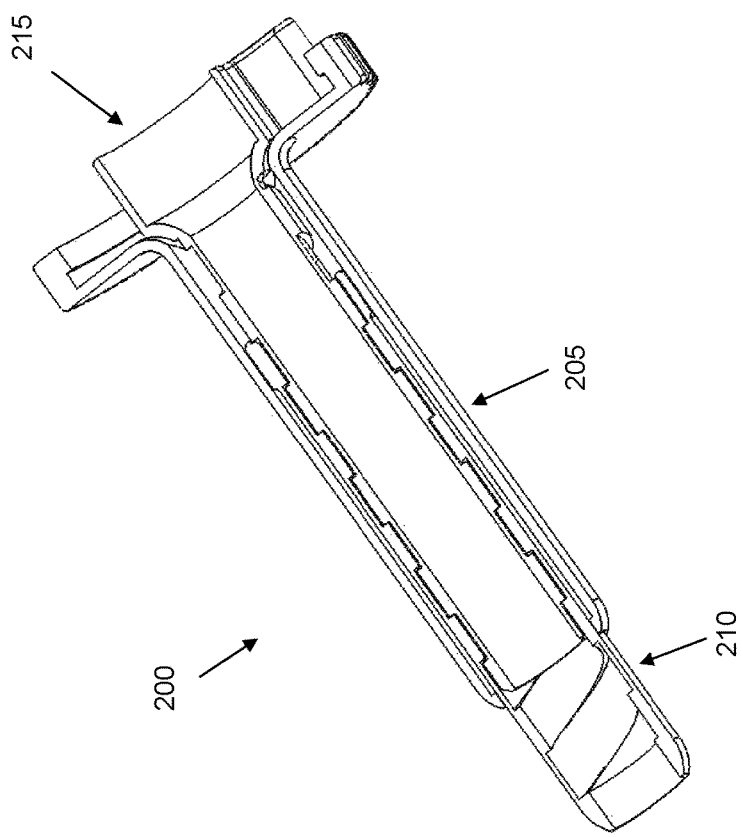
Figure 35:
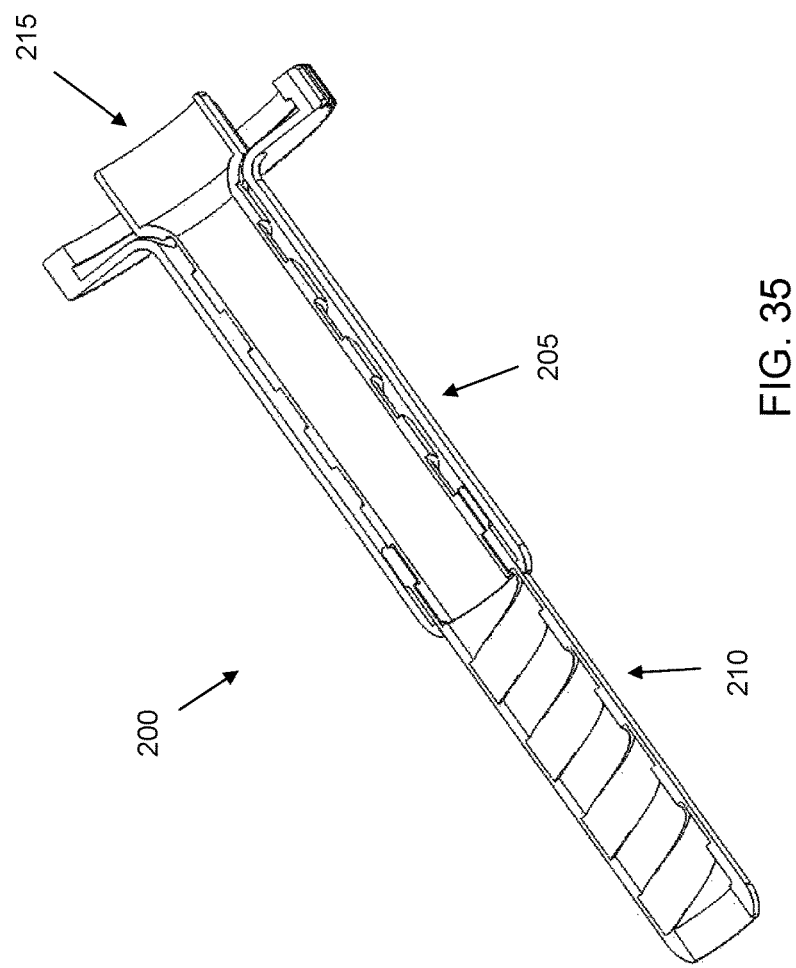
Figure 36:
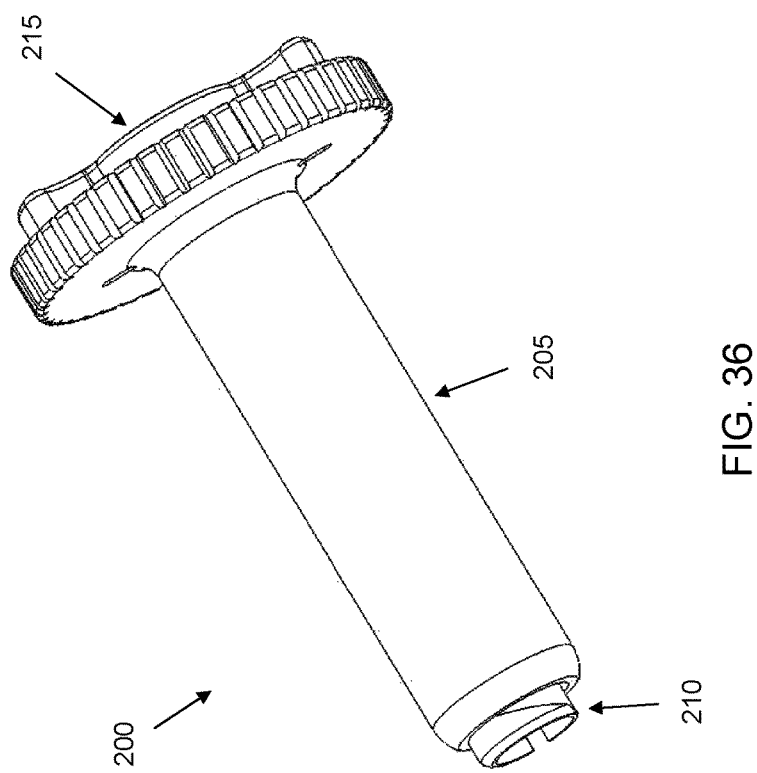
Figure 37:
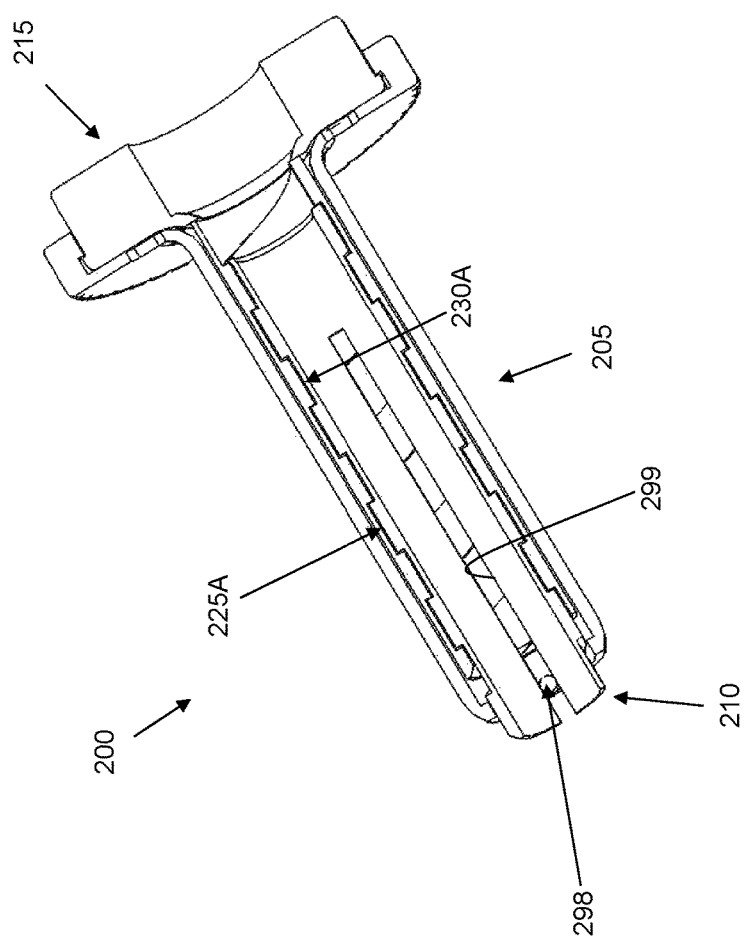
Figure 38:
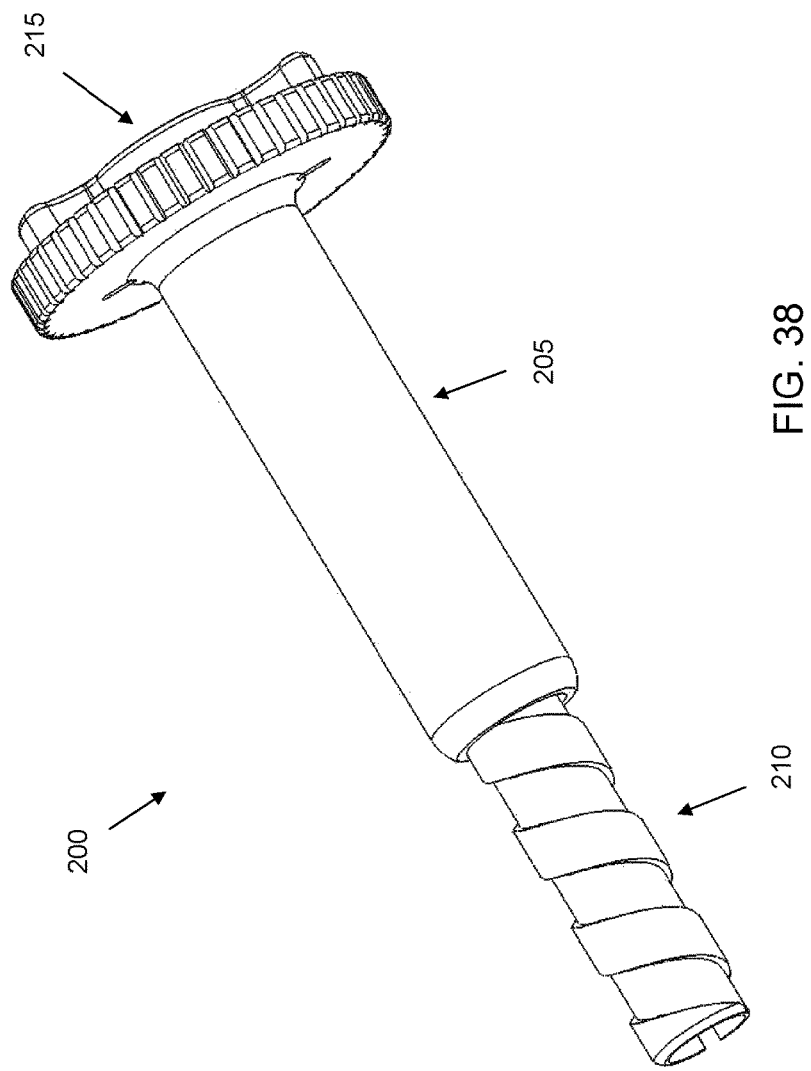
Figure 39:
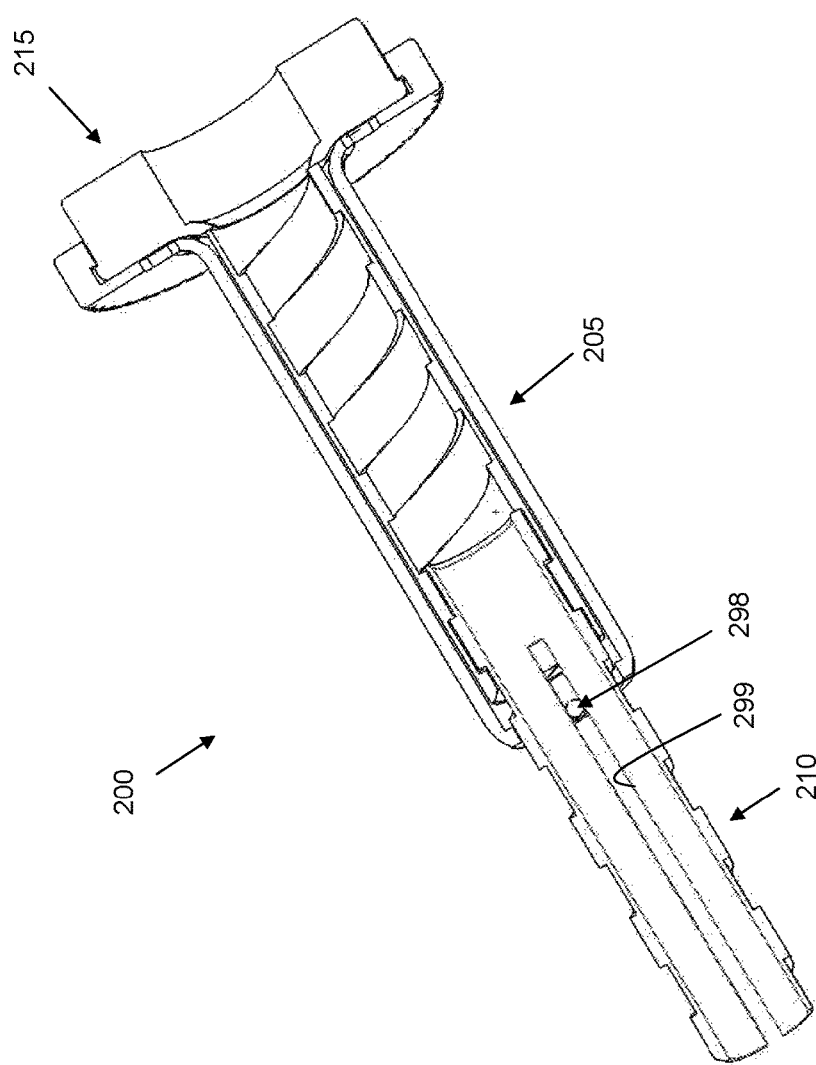
Figure 40:
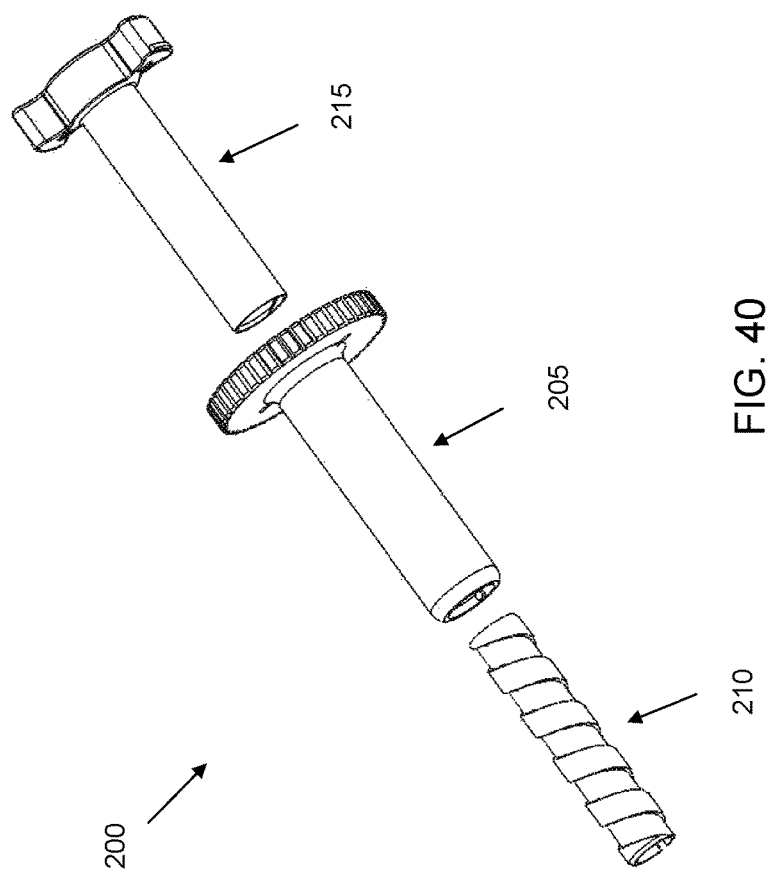
Figure 41:
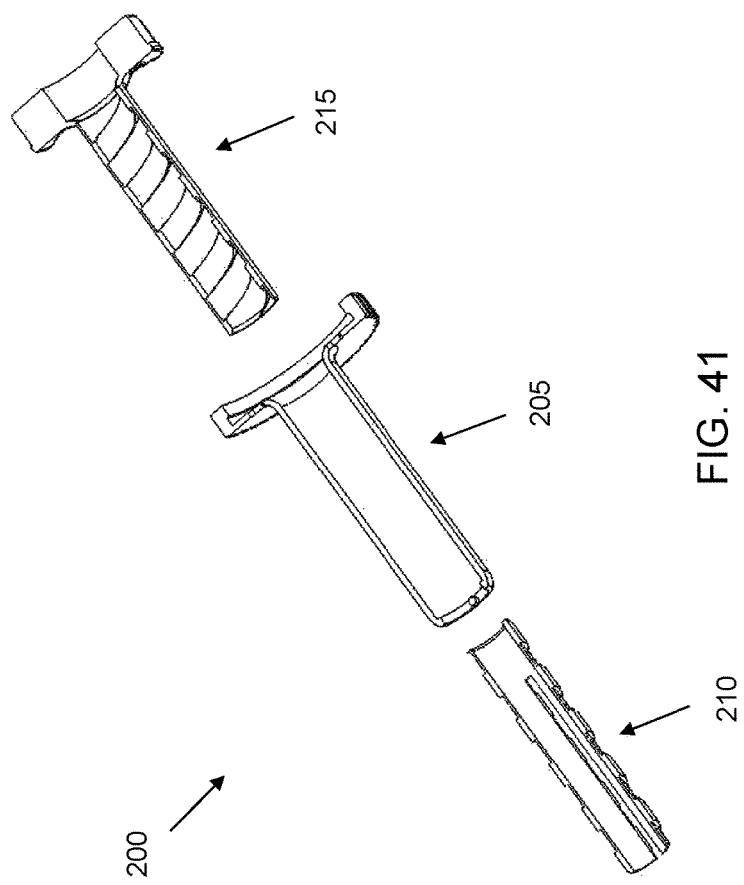
Figure 42:
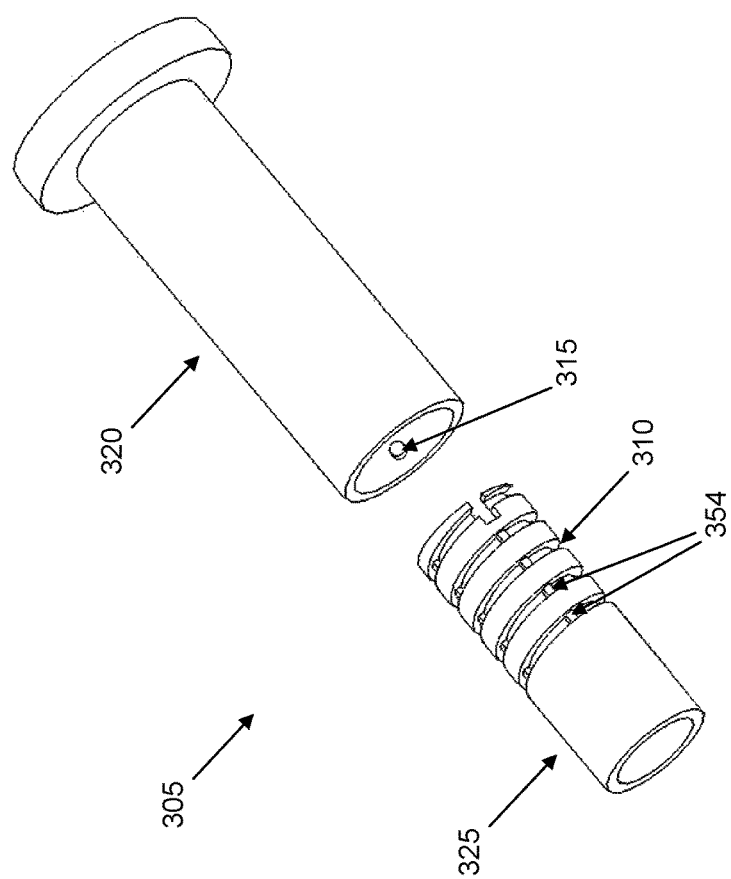
FIGS. 42-46 are schematic views showing a fourth type of telescoping access cannula formed in accordance with the present invention.
Figure 43:
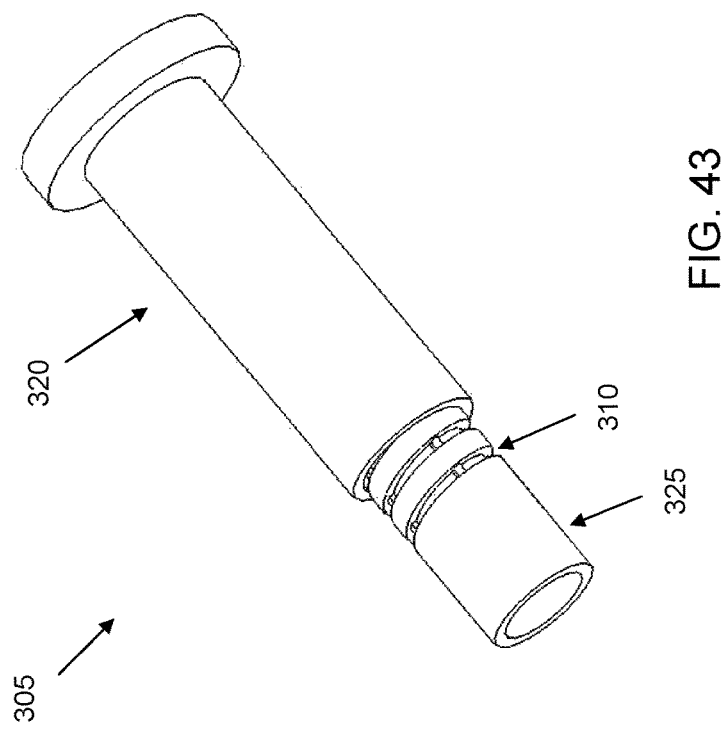
Figure 44:
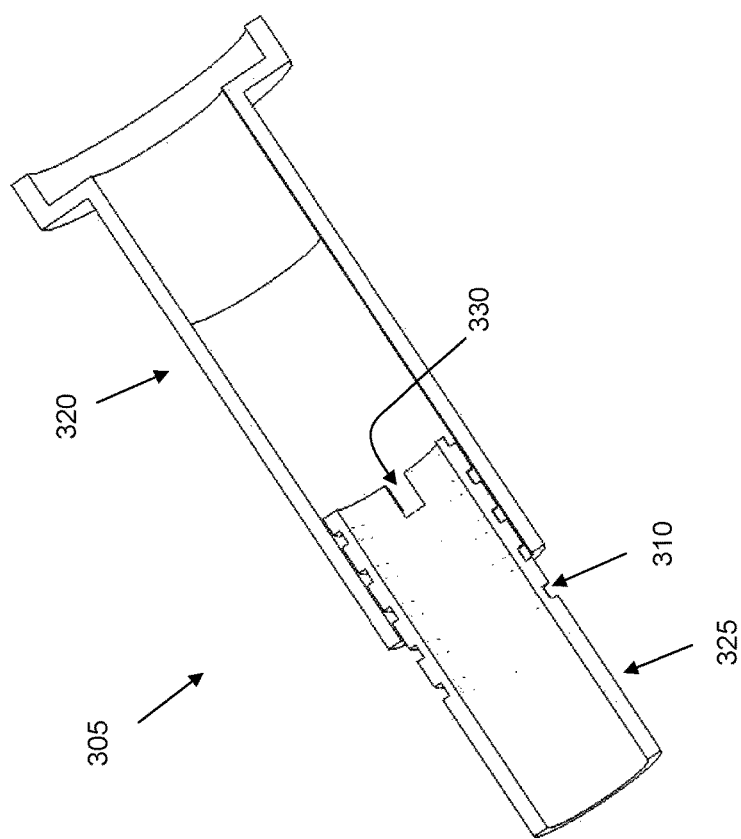
Figure 45:
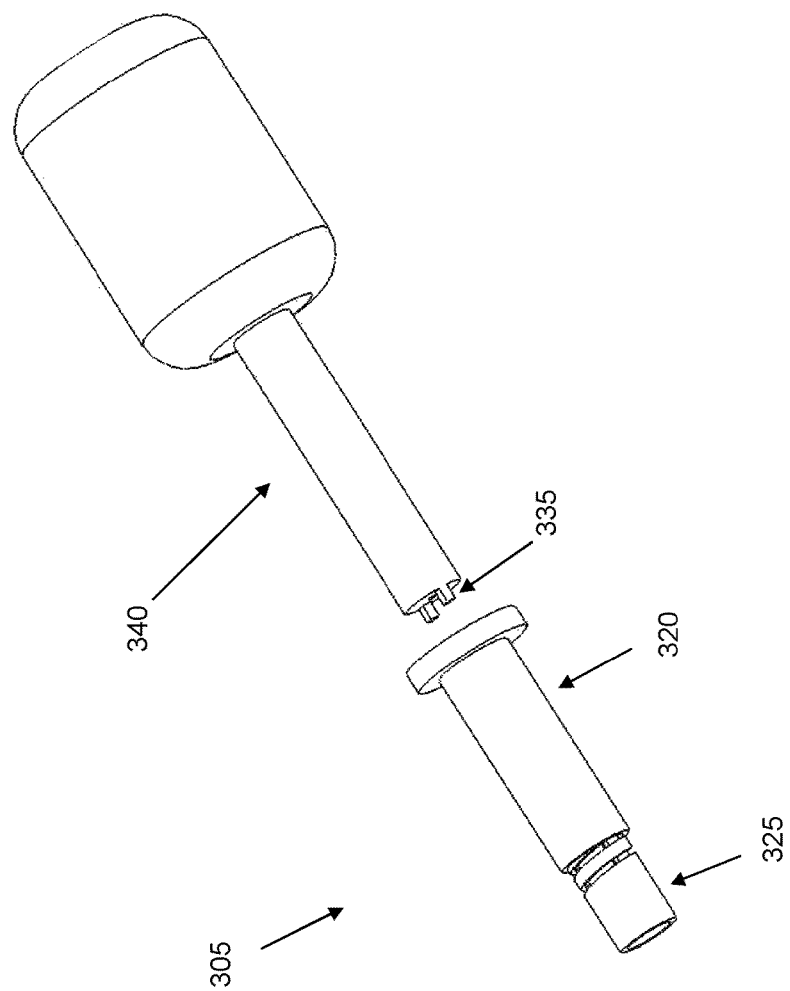
Figure 46:
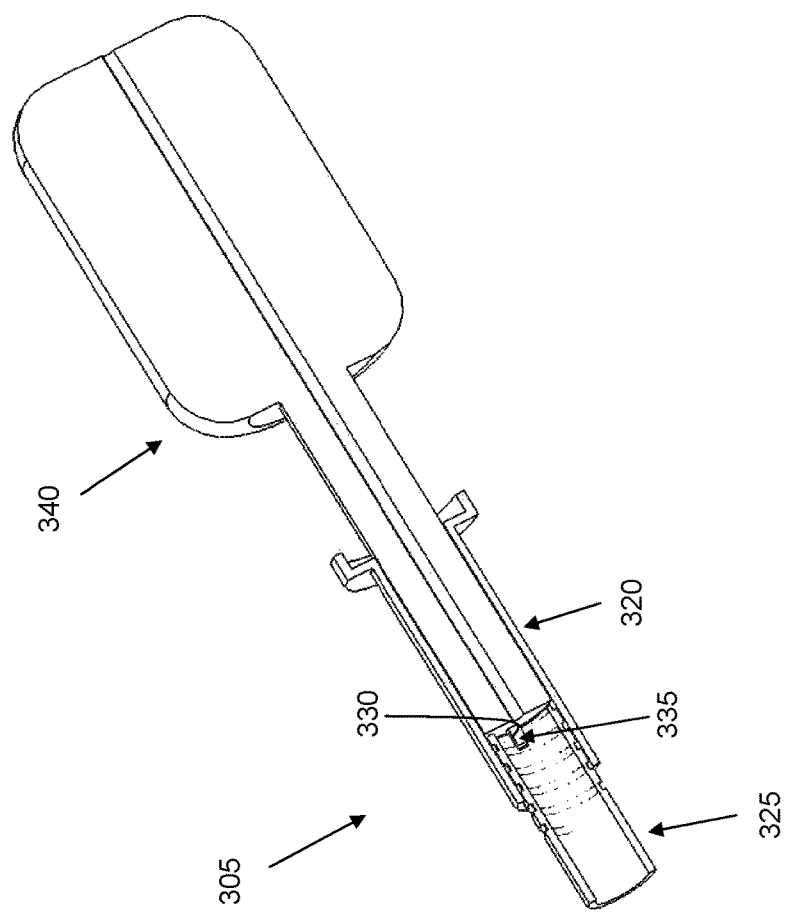

Telescoping inner tube 210 generally comprises a tube-like structure sized to be slidably received in stationary body 205 and having translation threads 225 formed on its inner surface. At least a portion of telescoping inner tube 210 is formed with at least one flat for alignment with at least one flat of stationary body 205, so that telescoping inner tube 210 cannot rotate relative to stationary body 205. This is important if rotation of threaded driver 215 is to impart longitudinal movement to telescoping inner tube 210. In one embodiment, the outer surface of telescoping inner tube 210 comprises six flats (e.g., a hexagonal geometry) and the inner surface of stationary body 205 comprises six corresponding flats (e.g., a corresponding hexagonal geometry). FIG. 32 is a cross-section of the telescoping inner tube 210 and stationary body 205 with corresponding hexagonal geometry. Although a hexagonal cross-section is depicted for stationary body 205 and telescoping inner tube 210, any feature which prevents rotation between inner tube 210 with stationary body 205 may suffice; for example, a single flat on an otherwise circular geometry, an octagonal cross-section, a key that slides in a slot, etc. may all be utilized to inhibit rotation between the two members.

Threaded driver 215 generally comprises a tube-like structure sized to be slidably received in telescoping inner tube 210, and having translation threads 230 formed on its outer surface. The proximal portion of threaded driver 215 comprises a flange 235 having keyways 236 for receiving the aforementioned keys 83 of telescoping obturator 15. Preferably one or more instrument-passing seals are disposed in flange 235. Flange 235 of threaded driver 215 is rotatably mounted to flange 220 of stationary body 205, such that threaded driver 235 can move rotationally, but not longitudinally, relative to stationary body 205. Translation threads 230 of threaded driver 215 engage translation threads 225 of telescoping inner tube 210, such that rotational motion imparted to threaded driver 215 can be transferred to telescoping inner tube 210 via translation threads 230, 225.

Stationary body 205, telescoping inner tube 210 and threaded driver 215 are assembled together in the manner shown so as to constitute the complete access cannula 200. It will be appreciated that, on account of the foregoing construction, rotational motion imparted to threaded driver 215 will be transferred to telescoping inner tube 210 via translation threads 230, 225, such that the longitudinal position of telescoping inner tube 210 can be adjusted vis-à-vis stationary body 205 by rotating threaded driver 215.

It will be appreciated that tubular stationary body 205, telescoping inner tube 210 and tubular threaded driver 215 are all aligned co-axial with one another so that their respective lumens collectively form a central lumen for the assembled telescoping access cannula.

In use, telescoping access cannula 200 is first adjusted so as to have a desired overall length, e.g., by turning threaded driver 215 so as to adjust the position of the distal end of telescoping inner tube 210 relative to stationary body 205. Then telescoping access cannula 200 is disposed in tissue, e.g., by using telescoping obturator 15 in the manner previously discussed, with keys 82, 83 of telescoping obturator 15 disposed in keyways 222, 236, respectively, of telescoping access cannula 200. Then telescoping obturator 15 is removed, and threaded driver 215 is used as desired to further adjust the position of the distal end of telescoping inner tube 210 relative to stationary body 205, and hence relative to the anatomy. The telescoping access cannula may then be used as a corridor for accessing the interior of the hip joint, by passing instrumentation (e.g., arthroscopes, surgical instruments, etc.) through the central lumen of the telescoping access cannula whereby to reach a remote site within the joint.

Significantly, due to the construction of the telescoping access cannula, the overall length of the telescoping access cannula may be adjusted either before deployment in the body or after deployment in the body, or both.

Looking next at FIG. 36-41, there is shown a related construction for telescoping access cannula 200. More particularly, the telescoping access cannula shown in FIGS. 36-41 is preferably substantially identical to the telescoping access cannula shown in FIGS. 30-35, except that in this form of the invention, threads 225A are formed on threaded driver 215 and threads 230A are formed on telescoping inner tube 210. In this construction, it is important that telescoping inner tube 210 not rotate relative to stationary body 205. This may be effected with the pin-and-slot mechanism show in FIG. 37, i.e., a pin 298 mounted to stationary body 205 and riding in a slot 299 formed in telescoping inner tube 210.

Fourth Type of Telescoping Access Cannula

FIGS. 42-46 show a two-stage telescoping access cannula 305 which uses another approach for adjusting the overall length of the telescoping access cannula. More particularly, in this construction, there is provided a first, telescoping inner tube 325 which comprises a track 310 which has a helical configuration, and a second, stationary outer tube 320 which comprises at least one (and preferably a pair of) diametrically-opposed fingers 315 which ride in the helical track 310 so as to provide a telescoping construction. Tubular stationary member 320 and tubular telescoping member 325 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, in one preferred form of the invention, there is provided a stationary member 320 which has a generally tubular construction and which has internal fingers 315 projecting inwardly therefrom, and there is provided a telescoping member 325 which has a generally tubular construction and which has the helical track 310 formed therein. Stationary member 320 is intended to be set into tissue, and to this end may include outer threads, etc. Telescoping member 325 is intended to be turned relative to stationary member 320, such that fingers 315 riding in track 310 will convert rotary motion into longitudinal motion, whereby to move telescoping member 325 relative to stationary member 320. In order to turn telescoping member 325 relative to stationary member 320, telescoping member 325 preferably includes a slot 330 in its proximal end which receives a finger 335 of a turning tool 340. If desired, holes 354 can be disposed along the length of helical track 315 so as to provide a ratchet action through engagement with fingers 315 as telescoping member 325 is turned. Holes 354 can be openings, slots, etc., or they can be replaced with bumps or any other feature which engage the fingers 315.

It will be appreciated that tubular stationary member 320 and tubular telescoping member 325 are aligned co-axial with one another, so that their respective lumens collectively form a central lumen for the assembled telescoping access cannula.

Thus it will be seen that with this form of the invention, turning tool 340 is first used to set the desired overall length of the telescoping access cannula, then stationary member 320 is set into the tissue, and then turning tool 340 is used to further adjust the overall length of the telescoping access cannula while in the tissue. The telescoping access cannula may then be used as a corridor for accessing the interior of the hip joint, by passing instrumentation (e.g., arthroscopes, surgical instruments, etc.) through the central lumen of the telescoping access cannula, whereby to reach a remote site within the joint.

Significantly, due to the construction of the telescoping access cannula, the overall length of the telescoping access cannula may be adjusted either before deployment in the body or after deployment in the body, or both.

In one preferred form of the invention, telescoping member 325 is initially fully retracted into stationary member 320, stationary member 320 is set into the tissue, and then turning tool 340 is used to adjust the overall length of the telescoping access cannula.

Fifth Type of Telescoping Access Cannula

Figure 47:
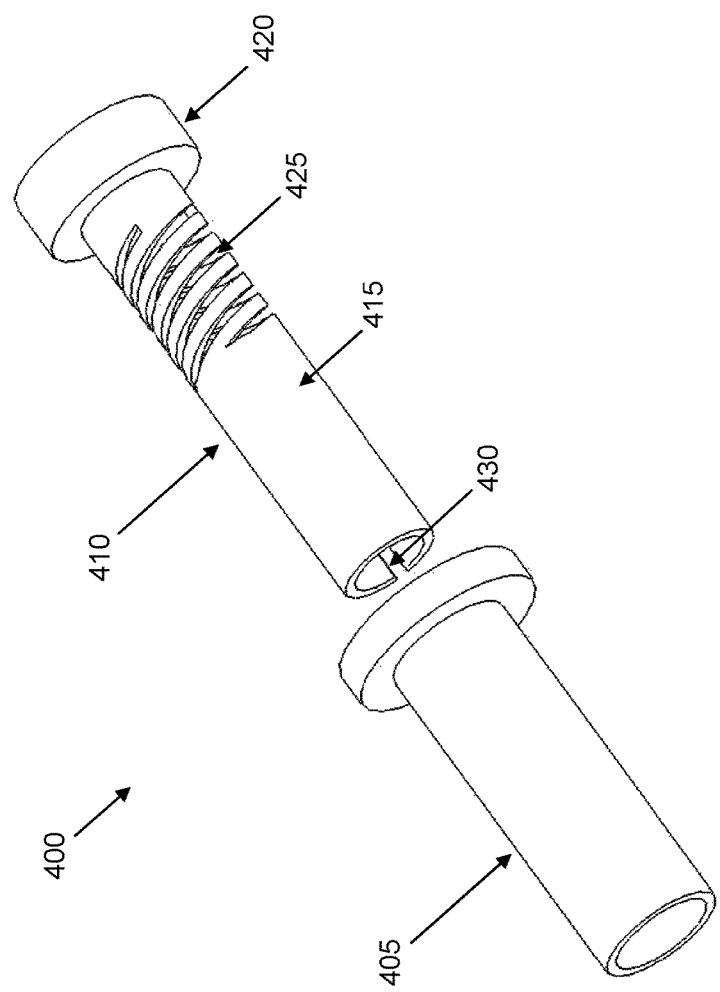
FIGS. 47-49 are schematic views showing a fifth type of telescoping access cannula formed in accordance with the present invention.
Figure 48:
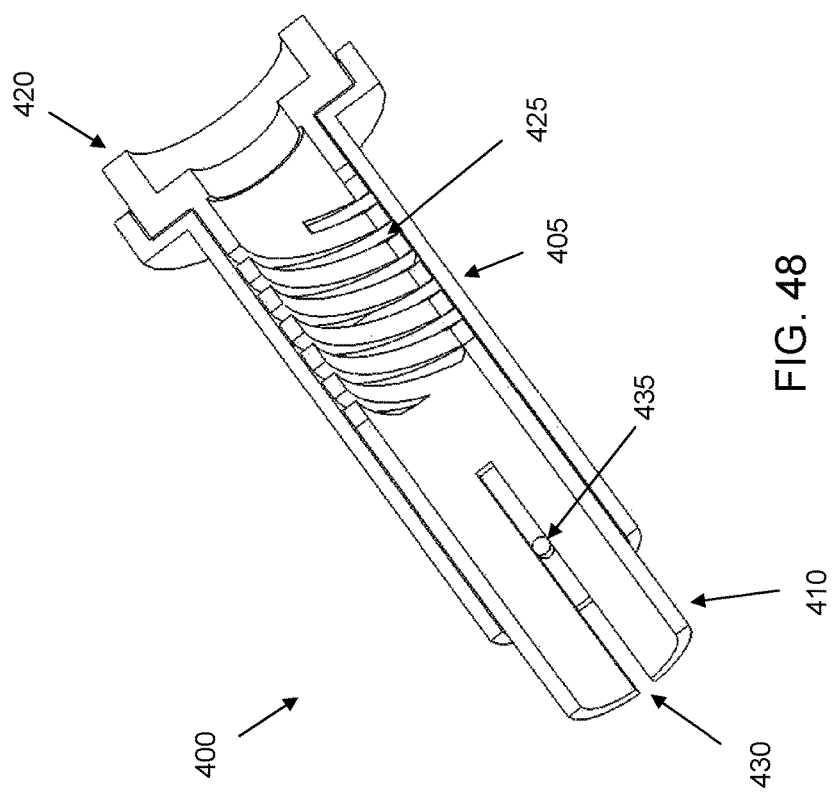
Figure 49:
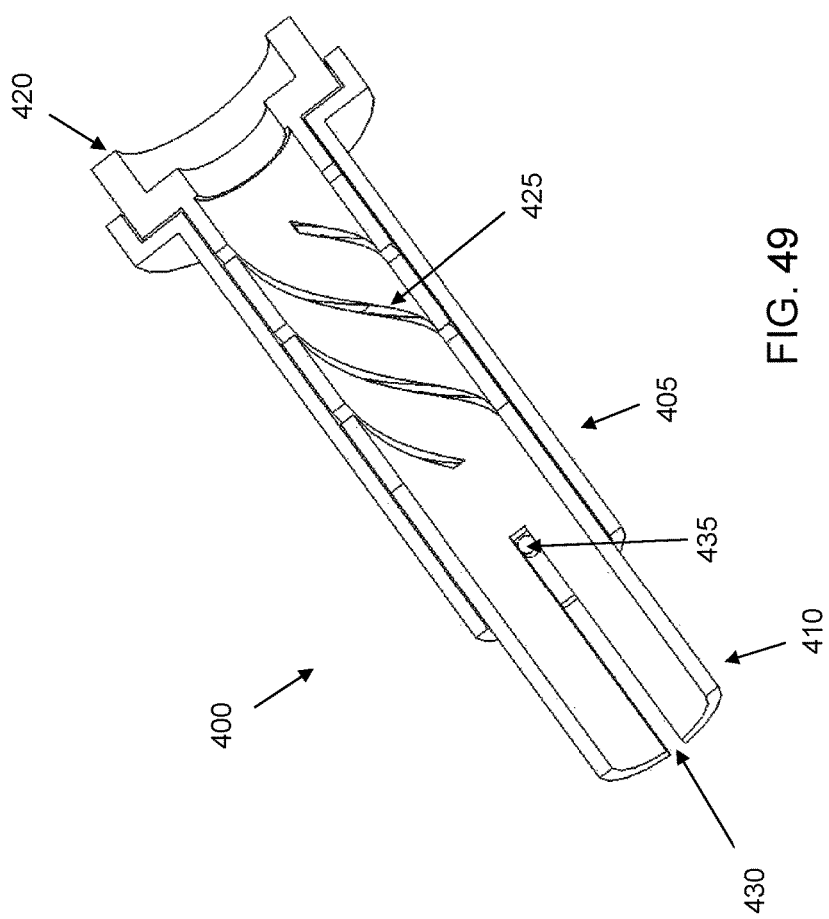

FIGS. 47-49 show a two-stage telescoping access cannula 400 which uses another approach for adjusting the overall length of the telescoping access cannula. More particularly, in this construction, there is provided a tubular stationary member 405 and a tubular telescoping member 410. Tubular stationary member 405 and tubular telescoping member 410 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

Stationary member 405 is intended to be set into tissue and, to this end, may include outer threads, etc. Telescoping member 410 is intended to be turned relative to stationary member 405 so as to adjust the overall length of the telescoping access cannula. To this end, telescoping member 410 comprises a shaft 415 terminating in a proximal flange 420 and having at least one helical through-slot 425 formed therein. Shaft 415 has at least one longitudinal slot 430 at its distal end. Longitudinal slot 430 receives a pin 435 which projects inwardly from the side wall of stationary member 405. As a result of this construction, when proximal flange 420 of telescoping member 410 is turned, the presence of helical through-slot 425 causes shaft 415 to lengthen or shorten, according to the direction in which proximal flange 420 is turned.

It will be appreciated that tubular stationary member 405 and tubular telescoping member 410 are aligned co-axial with one another so that their respective lumens collectively form a central lumen for the assembled telescoping access cannula.

Thus, in this form of the invention, proximal flange 420 is first turned so as to set the desired overall length of the telescoping access cannula, then stationary member 405 is set into the tissue, and then proximal flange 420 is used to further adjust the overall length of the telescoping access cannula. The telescoping access cannula may then be used as a corridor for accessing the interior of the joint, by passing instrumentation (e.g., arthroscopes, surgical instruments, etc.) through the central lumen of the telescoping access cannula, whereby to reach a remote site within the joint.

Significantly, due to the construction of the telescoping access cannula, the overall length of the telescoping access cannula may be adjusted either before deployment in the body or after deployment in the body, or both.

In one preferred form of the invention, telescoping member 410 is initially fully retracted into stationary member 405, stationary member 405 is set into the tissue, and then proximal flange 420 is used to adjust the overall length of the telescoping access cannula.

It should be appreciated that various alternative constructions may be used to prevent rotation between stationary member 405 and telescoping member 410. Thus, while FIGS. 47-49 show a longitudinal slot 430 receiving a pin 435, any features which prevent rotation between the stationary member 405 and a telescoping member 410 will suffice (e.g., flats, hexagonal cross-sections, keyways, etc.)

Sixth Type of Telescoping Access Cannula

In another form of the invention, a linear ratchet mechanism is used to form the telescoping access cannula.

Figure 50:
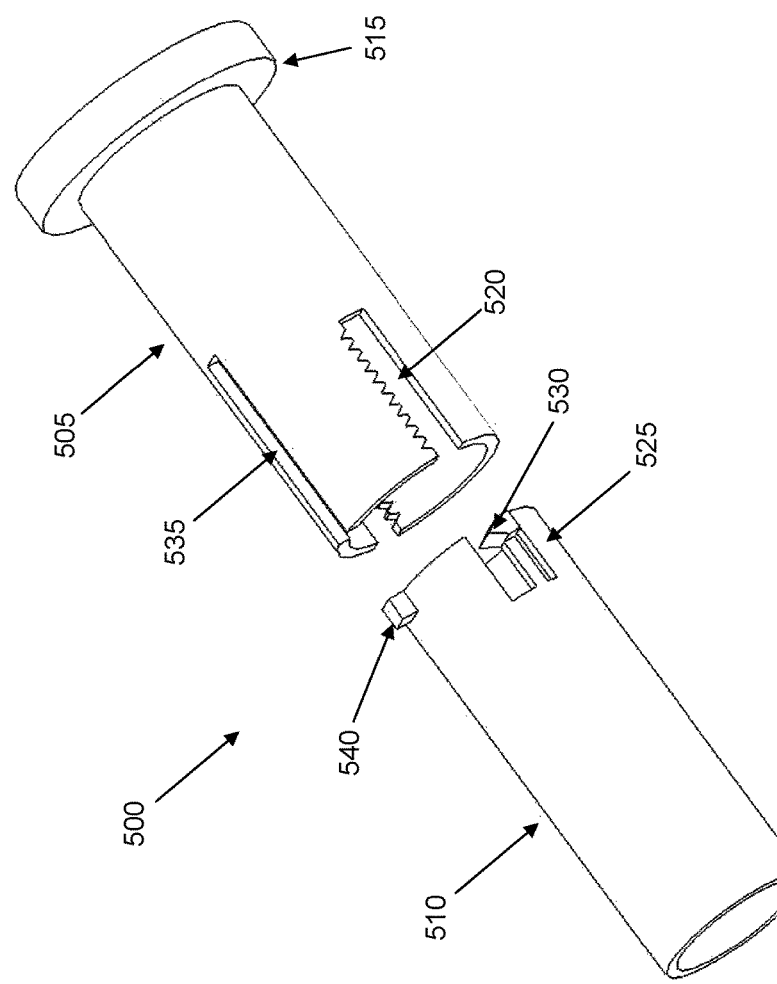
FIGS. 50-54 are schematic views showing a sixth type of telescoping access cannula formed in accordance with the present invention.
Figure 51:
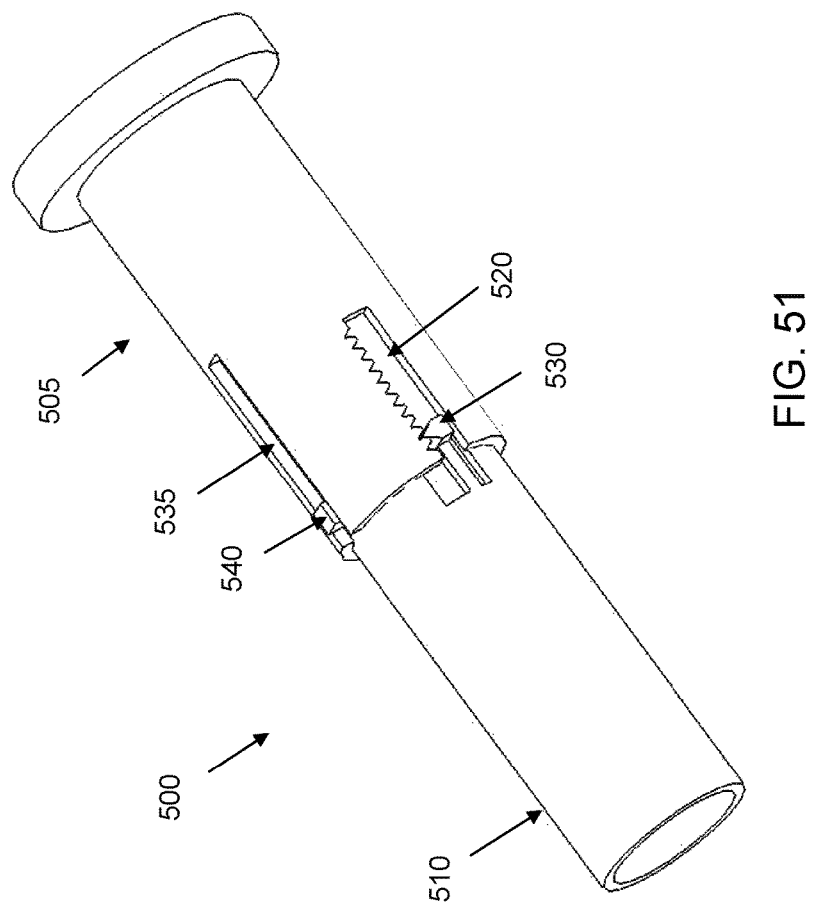
Figure 52:
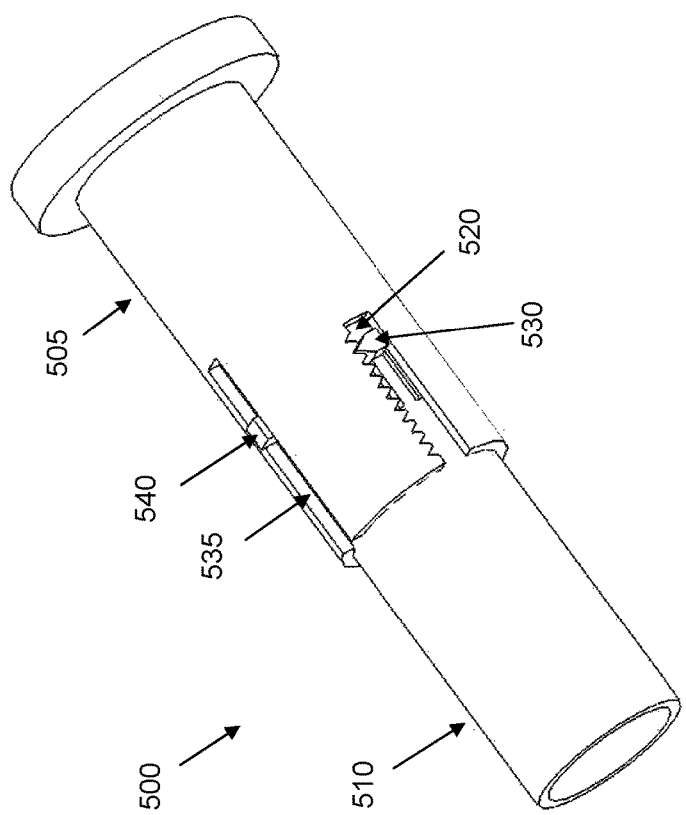

More particularly, and looking now at FIGS. 50-52, there is shown a novel telescoping access cannula 500 formed in accordance with the present invention.

Telescoping access cannula 500 generally comprises a tubular stationary body 505 for seating in the patient's tissue and a telescoping inner tube 510 for adjustable positioning relative to stationary body 505. Tubular stationary body 505 and telescoping inner tube 510 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, stationary body 505 generally comprises a tube-like structure. The proximal portion of stationary body 505 preferably comprises a flange 515. If desired, securement threads (not shown) may be disposed on the outer surface of stationary body 505. A plurality of ratchet openings 520 are formed in stationary body 505 for interaction with telescoping inner tube 510, as will hereinafter be discussed in further detail.

Telescoping inner tube 510 generally comprises a tube-like structure sized to be slidably received in stationary body 505. The proximal end of telescoping inner tube 510 terminates in a plurality of diametrically-opposed fingers 525. Diametrically-opposed fingers 525 are flexible and include pawls 530 at their proximal ends for interaction with ratchet openings 520 of stationary body 505, as will hereinafter be discussed in further detail.

Stationary body 505 and telescoping inner tube 510 are assembled together in the manner shown so as to together constitute the complete telescoping access cannula 500. It will be appreciated that, on account of the foregoing construction, telescoping inner tube 510 may be advanced longitudinally within stationary body 505, with pawls 530 making a ratcheting engagement with ratchet openings 520 in stationary body 505. Thus, the longitudinal position of telescoping inner tube 510 may be advanced or retracted vis-à-vis stationary body 505 via the aforementioned ratchet mechanism.

It will be appreciated that tubular stationary body 505 and telescoping inner tube 510 are aligned co-axial with one another so that their respective lumens collectively form a central lumen for the assembled telescoping access cannula.

Various deployment tools may be used to advance or retract telescoping inner tube 510 relative to stationary body 505. Furthermore, by appropriately configuring these deployment tools to permit diametrically-opposed fingers 525 to be drawn together (i.e., so as to withdraw pawls 530 from ratchet openings 520 into the interior of stationary body 505), telescoping inner tube 510 may be drawn fully proximally relative to stationary body 505.

In use, telescoping access cannula 500 is preferably first disposed in tissue, and then telescoping inner tube 510 is advanced relative to stationary body 505, and hence relative to the anatomy, using the ratchet mechanism. Furthermore, by appropriately configuring the aforementioned deployment tools, telescoping inner tube 510 may be withdrawn proximally relative to stationary body 505. The telescoping access cannula may then be used as a corridor for accessing the interior of the joint space by passing instrumentation (e.g., arthroscopes, surgical instruments, etc.) through the central lumen of the telescoping access cannula, whereby to reach a remote site within the joint.

Significantly, due to the construction of the telescoping access cannula, the overall length of the telescoping access cannula may be adjusted either before deployment in the body or after deployment in the body, or both.

In one preferred form of the invention, alignment means are provided for ensuring proper alignment between stationary body 505 and telescoping inner tube 510. More particularly, in this form of the invention, there is provided an alignment slot 535 in stationary body 505 which receives an alignment finger 540 which is formed on telescoping inner tube 510.

Figure 53:
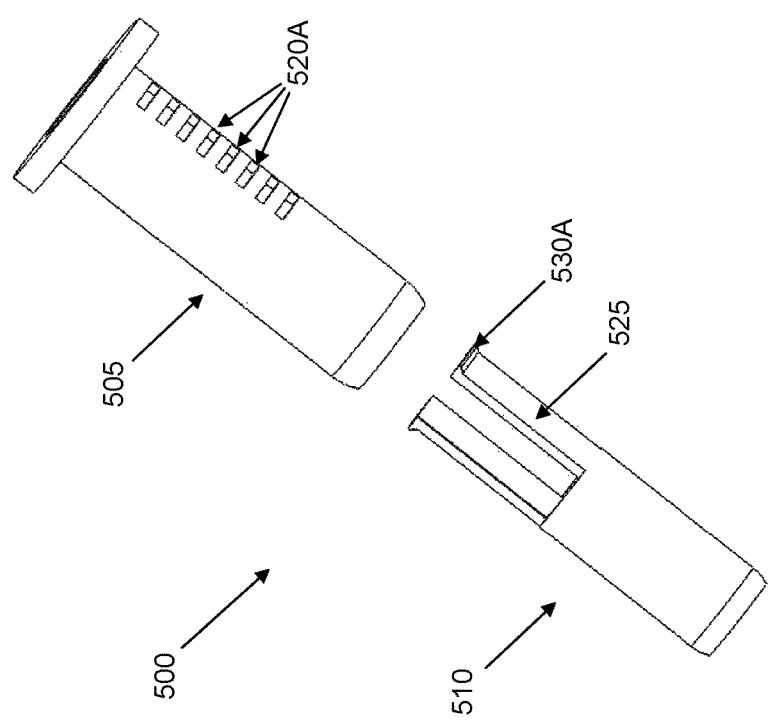
Figure 54:
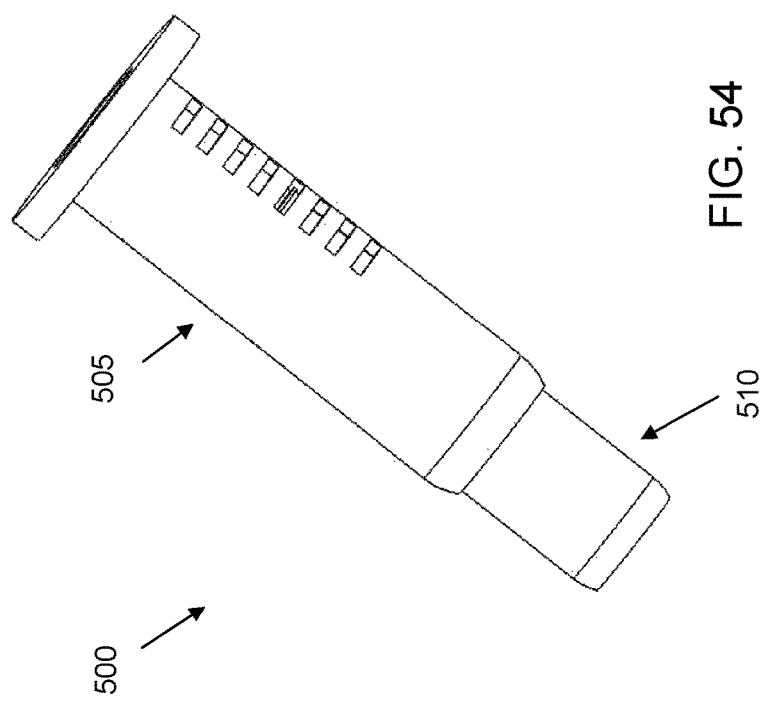
Figure 55:
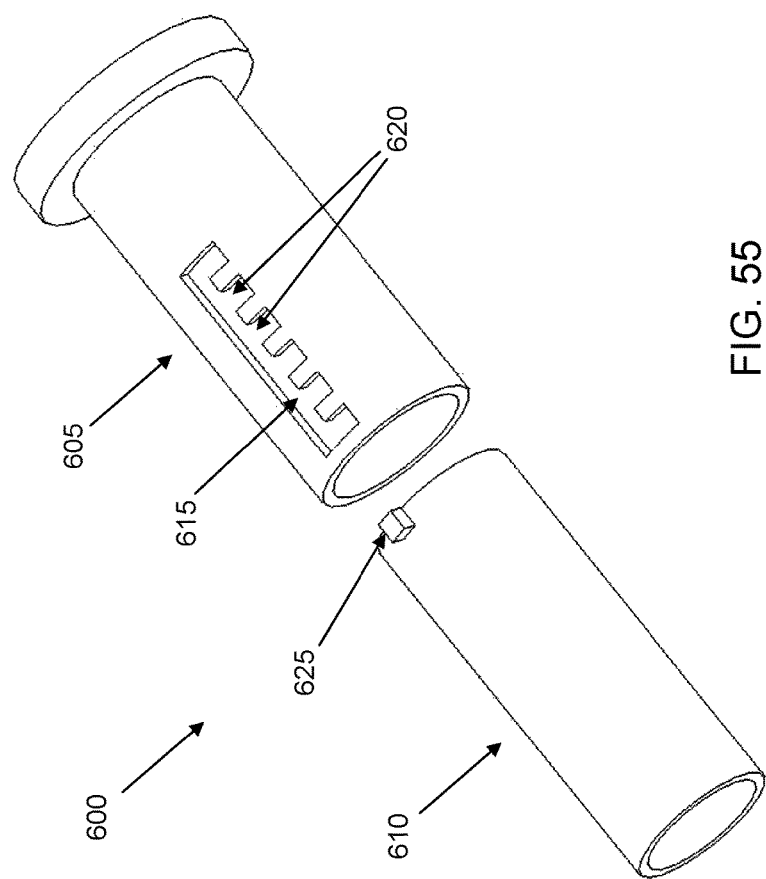
FIGS. 55-58 are schematic views showing a seventh type of telescoping access cannula formed in accordance with the present invention.
Figure 56:
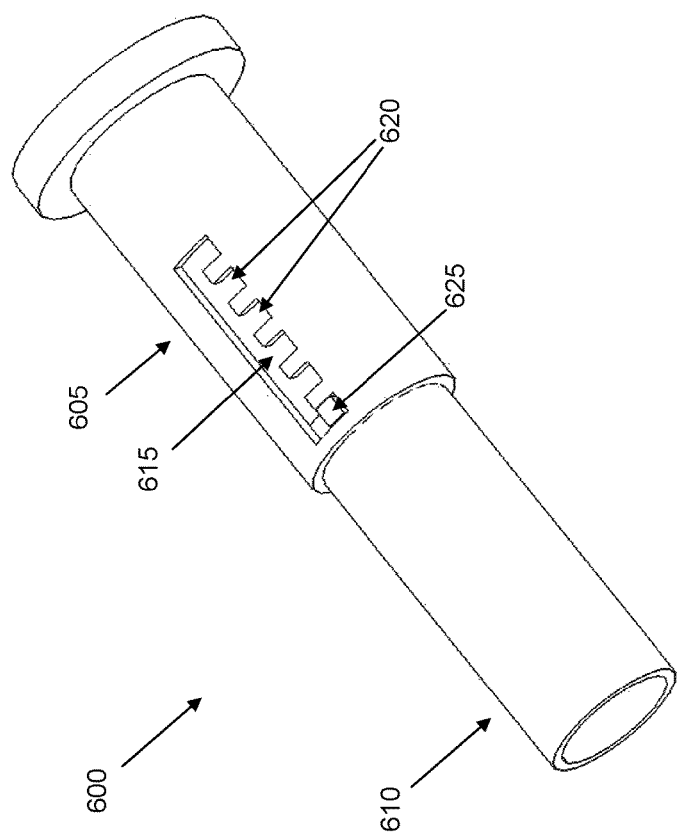
Figure 57:
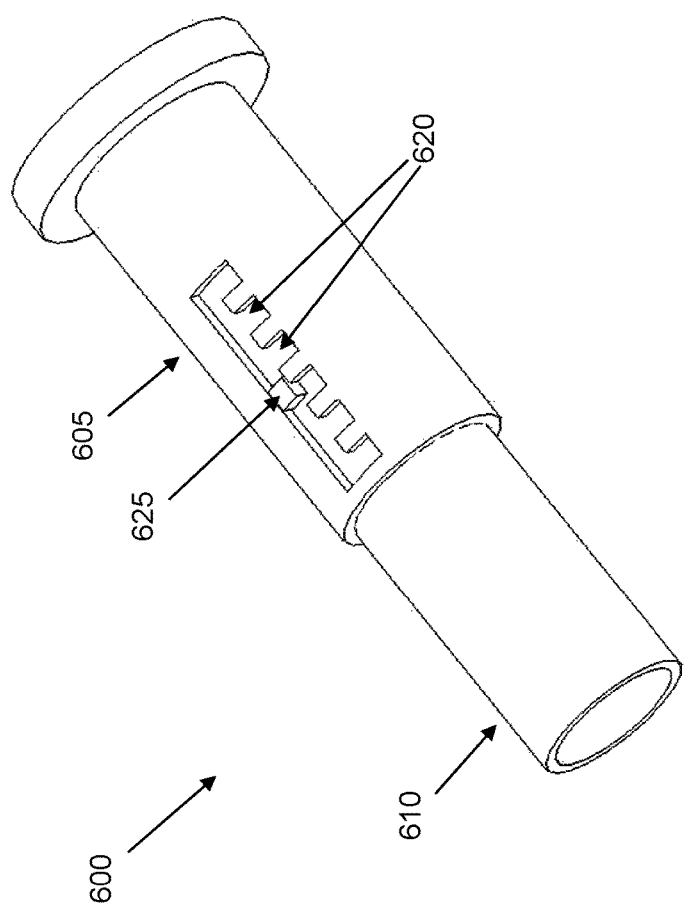
Figure 58:
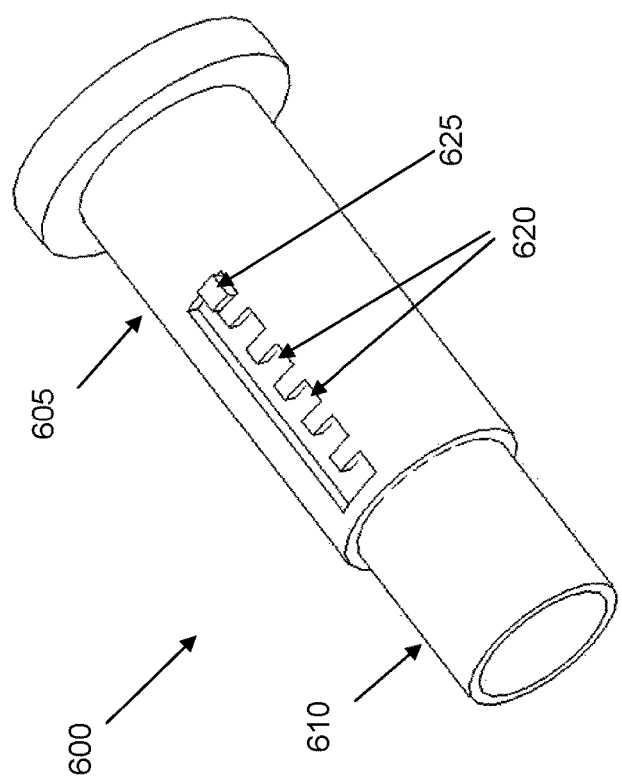

If desired, and looking now at FIGS. 53 and 54, stationary body 505 can comprise discrete ratchet openings 520A, and telescoping inner tube 510 can comprise fingers 525A which include pawls 530A on their proximal ends, with pawls 530A being releasably received in ratchet openings 520A, whereby to adjust the overall length of telescoping access cannula 500.

Seventh Type of Telescoping Access Cannula

FIGS. 55-58 show how a two-stage telescoping access cannula 600 can have its first stage (i.e., an outer tube 605) and its second stage (i.e., a telescoping inner tube 610) adjustably locked to one another via a "twist/slide/twist" approach. Outer tube 605 and inner tube 610 together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, in this form of the invention, one of the stages (e.g., outer tube 605) has a track 615 formed therein, where the track 615 includes multiple circumferentially-extending slots 620, and the other of the stages (e.g., telescoping inner tube 610) has a finger 625 which is received in track 615. As a result of this combination, by using an appropriate "twist/slide/twist" action, finger 625 can be seated in an appropriate circumferentially-extending slot 620, whereby to adjustably set the overall length of telescoping access cannula 600.

It will be appreciated that outer tube 605 and inner tube 610 are aligned co-axial with one another, so that their respective lumens collectively form a central lumen for the assembled telescoping access cannula.

Eighth Type of Telescoping Access Cannula

In another form of the invention, a modular construction is used to form the telescoping access cannula.

Figure 59:
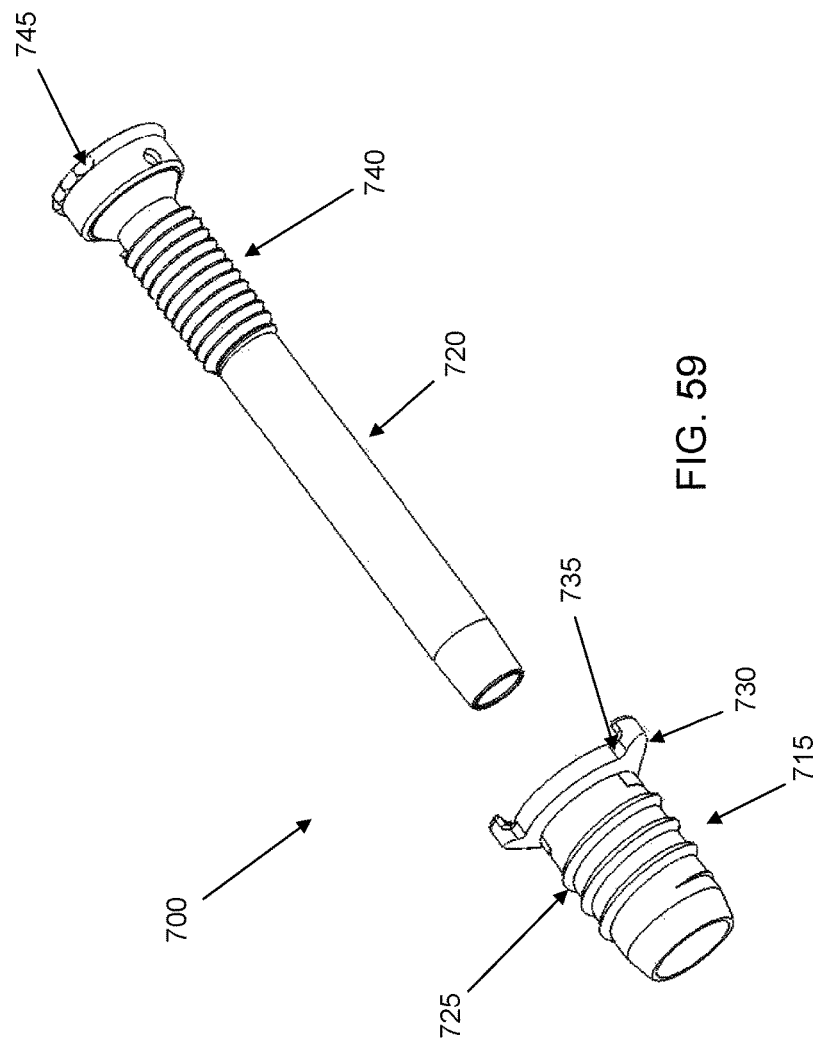
FIGS. 59-60 are schematic views showing an eighth type of telescoping access cannula formed in accordance with the present invention.
Figure 60:
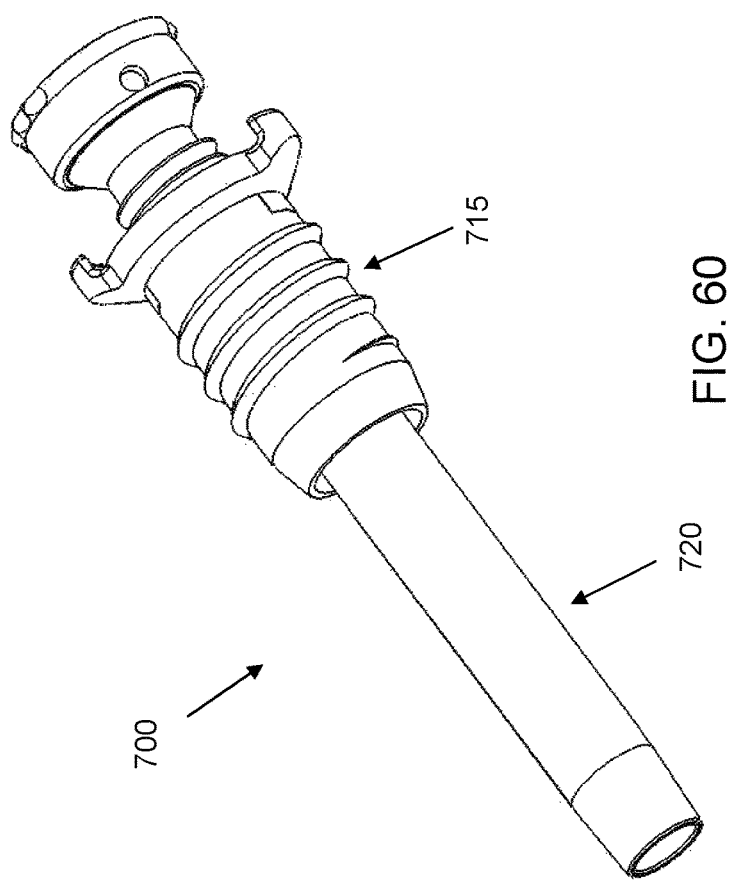
Figure 61:
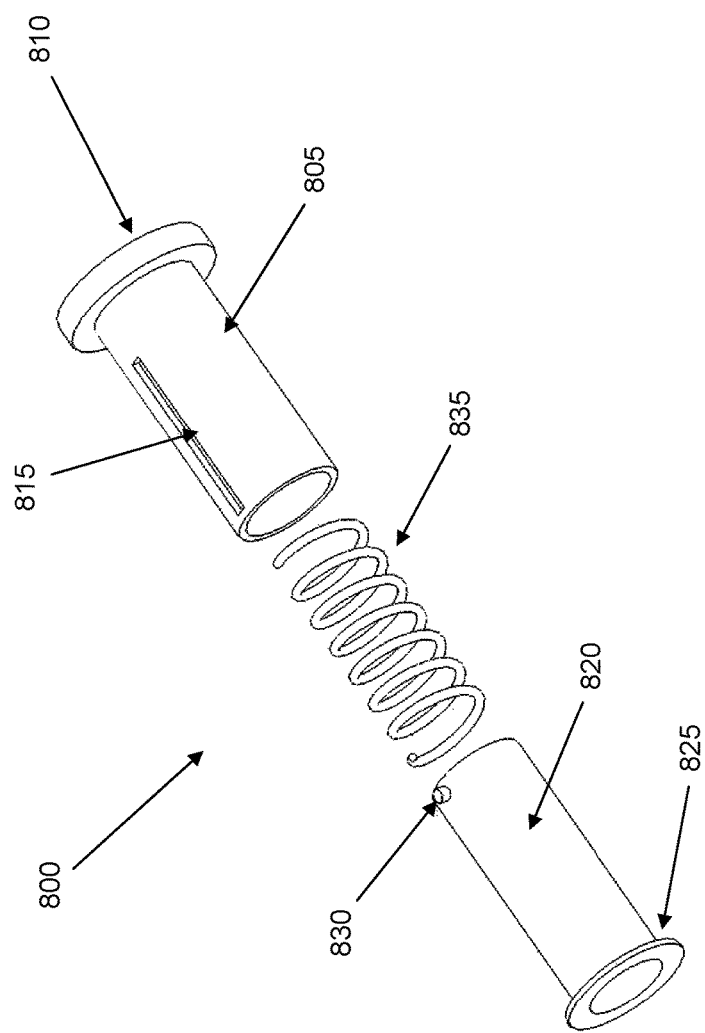

More particularly, and looking now at FIGS. 59 and 60, there is shown a novel telescoping access cannula 700. Telescoping access cannula 700 generally comprises a tubular stationary body 715 for seating in the patient's tissue, and a telescoping inner tube 720 for adjustable positioning relative to stationary body 715. Tubular stationary body 715 and telescoping inner tube 720 together form a telescoping tubular liner structure which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, stationary body 715 generally comprises a tube-like structure having securement threads 725 formed on its outer surface and translation threads (not shown) formed on its inner surface. The proximal portion of stationary body 715 preferably comprises a flange 730. Flange 730 preferably comprises one or more keyways 735 for selective engagement in one or more keys in a corresponding telescoping obturator.

Telescoping inner tube 720 generally comprises a tube-like structure sized to be slidably received in stationary body 715 and having translation threads 740 formed in its outer surface. Translation threads 740 of telescoping inner tube 720 engage the aforementioned translation threads (not shown) of stationary body 715, such that rotation of telescoping inner tube 720 relative to stationary body 715 causes longitudinal movement of telescoping inner tube 720 relative to stationary body 715. Telescoping inner tube 720 preferably includes one or more keyways 745 on its proximal end for selective engagement by one or more keys in a corresponding telescoping obturator.

Stationary body 715 and telescoping inner tube 720 are assembled together in the manner shown so as to constitute the complete telescoping access cannula 700. It will be appreciated that, on account of the foregoing construction, rotational motion imparted to telescoping inner tube 720 will cause the longitudinal position of telescoping inner tube 720 to be adjusted vis-a-vis stationary body 715.

It will be appreciated that tubular stationary body 715 and telescoping inner tube 720 are aligned co-axial with one another, so that their respective lumens collectively form a central lumen for the assembled telescoping access cannula.

Thus, in this form of the invention, telescoping inner member 720 is first turned so as to set the desired overall length of the telescoping access cannula, then stationary body 715 is set into the tissue, and then telescoping inner member 720 is further turned as desired so as to further adjust the overall length of the telescoping access cannula. The telescoping access cannula may then be used as a corridor for accessing the interior of the joint space by passing instrumentation (e.g., arthroscopes, surgical instruments, etc.) through the central lumen of the telescoping access cannula, whereby to reach a remote site within the joint.

Significantly, due to the construction of the telescoping access cannula, the overall length of the telescoping access cannula may be adjusted either before deployment in the body or after deployment in the body, or both.

Ninth Type of Telescoping Access Cannula

Looking next at FIGS. 61-65, there is shown another novel telescoping access cannula 800. Telescoping access cannula 800 generally comprises an outer sleeve 805 and an inner sleeve 820 which together form a telescoping tubular liner structure having a central lumen which can be used to provide a surgical pathway (or "corridor") from the top surface of the skin down to the interior of the hip joint, thereby enabling instrumentation (e.g., arthroscopes, surgical instruments, etc.) to be passed through the central lumen of the telescoping access cannula so as to reach a remote surgical site within the joint. In this way, the telescoping access cannula may be used to enable minimally-invasive, "keyhole" surgery to be performed on the hip joint.

More particularly, telescoping access cannula 800 generally comprises (i) an outer sleeve 805 which includes a proximal lip and seal 810 and a guide slot 815, (ii) an inner sleeve 820 which includes a distal lip 825 and a guide pin 830, and (iii) a tension spring 835. Inner sleeve 820 is telescopically disposed within outer sleeve 805, with guide slot 815 and guide pin 830 ensuring smooth telescoping action and with tension spring 835 yieldably biasing distal lip 825 toward proximal lip and seal 810. It will be appreciated that tubular outer sleeve 805 and tubular inner sleeve 820 are aligned co-axial with one another, so that their respective lumens collectively form a central lumen for the assembled telescoping access cannula.

Additional Constructions

In addition to the foregoing, it is also anticipated that at least a portion of the telescoping access cannula (e.g., an inner tube) may be formed out of an optically-transmissive material, such that the telescoping access cannula may serve as a light conduit for delivering light from an external light source (e.g., a light diode or light box) to the region around the distal end of the telescoping access cannula. Such an approach can be used to improve visualization of structures disposed adjacent to the distal end of the telescoping access cannula in the interior of a joint, and may also allow for the use of smaller endoscopes, which can be highly advantageous since it can facilitate improved joint access. In this embodiment, the inner cannula is preferably formed out of an optically transmissive material such as acrylic or polycarbonate.

Also, in some preferred forms of the invention, the telescoping access cannula may be provided with fixation features (e.g., slots, knobs, etc.) on the proximal end of the telescoping access cannula (e.g., the stationary tube or knob, etc.) for use in securing suture to the telescoping access cannula.

And, in some preferred forms of the invention, the telescoping access cannula may include fixation features for releasably securing instruments to the telescoping access cannula, e.g., a clamp which mounts onto the proximal end of the telescoping access cannula so as to hold an instrument in position relative to the telescoping access cannula. This feature can help reduce the number of "hands" needed during a surgical procedure, by stabilizing an instrument vis-a-vis the telescoping access cannula (which is itself stabilized relative to the patient's tissue).

Furthermore, the telescoping access cannula can include fixation features and/or other aids for supporting and/or guiding percutaneous instruments used in a surgical procedure. By way of example but not limitation, the telescoping access cannula may include a guide mounted to the telescoping access cannula to help target percutaneous devices to specific locations within the body.

Furthermore, as was stated previously, the port on the stationary tube (e.g., port 40 in outer tube 20) is in fluid communication with the interior of the stationary tube. As such, fluid can travel through the inner tube, the stationary tube and the port so as to enter and exit the joint space. Tubing can be connected to the port. In one embodiment, fluid can be pumped into the joint via the tubing. In another embodiment, fluid can be evacuated from the joint via the port 40. Tubing can be connected to the port 40 which can direct fluid flow; alternatively, tubing can be attached to active suction.

Furthermore, the stationary tube can comprise one or more holes which extend completely through the side wall of the tube, so that the interior of the tube is in communication with the region adjacent the exterior surface of the stationary tube. This enables fluid which has collected in the adjacent tissues to drain into the telescoping access cannula and out the cannula's port. The telescoping inner tube can be provided with similar openings if desired.

Furthermore, although the seals are shown in a proximal location in the telescoping access cannula, one or more of the seals can alternatively be located in a more distal location within the telescoping access cannula. For example, the distal seal can be located in the distal region of the stationary tube, while the proximal seal can be located in the proximal end of the stationary tube. Alternatively, the distal seal can be located in the inner tube.

Additional Telescoping Obturator Construction

Figure 66:
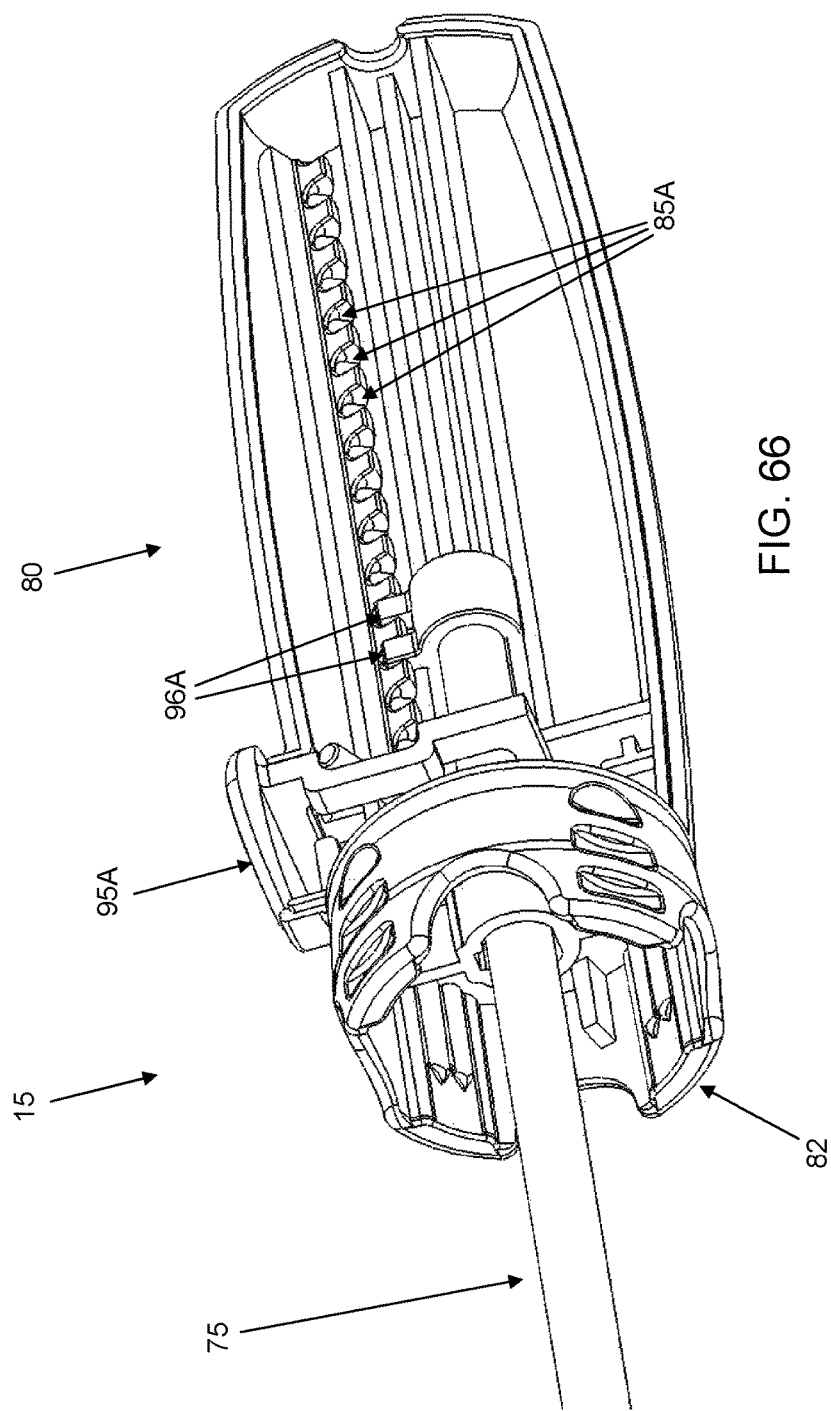
FIGS. 66-72 show additional telescoping obturator constructions.
Figure 67:
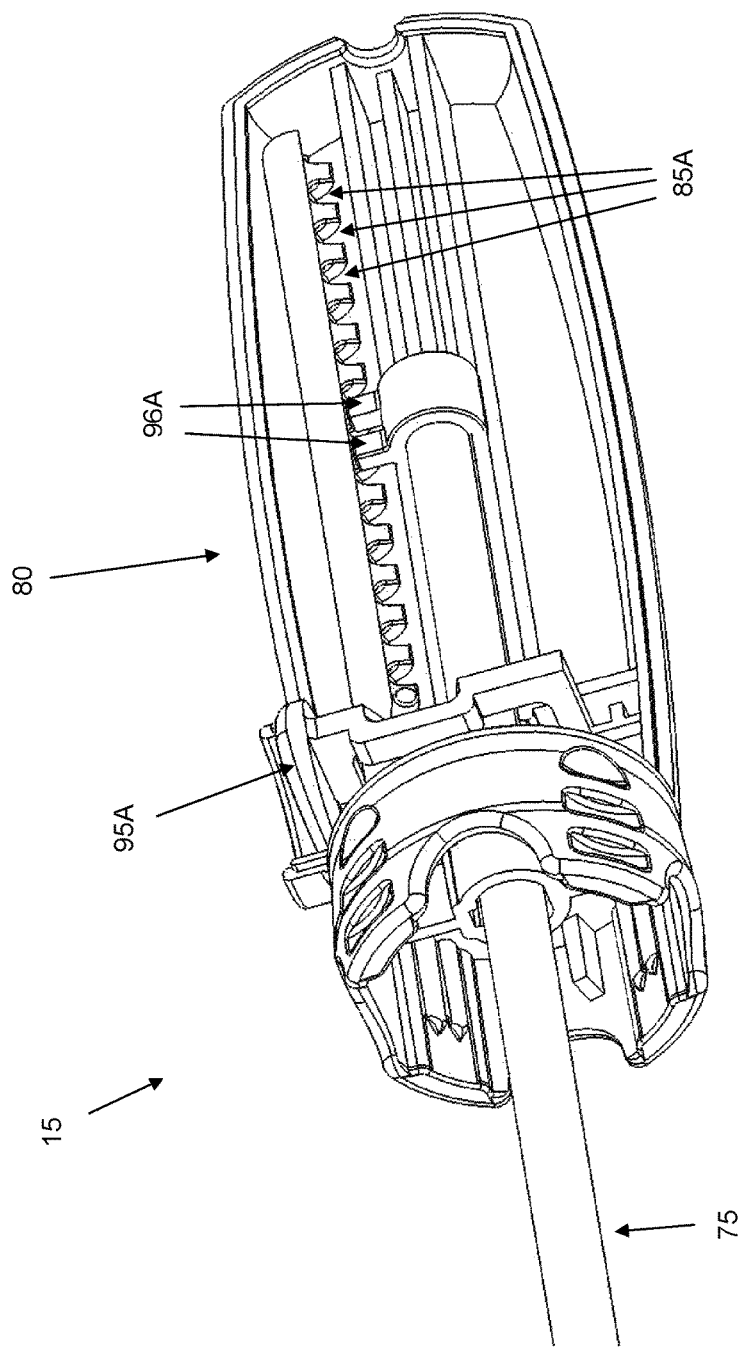
Figure 68:
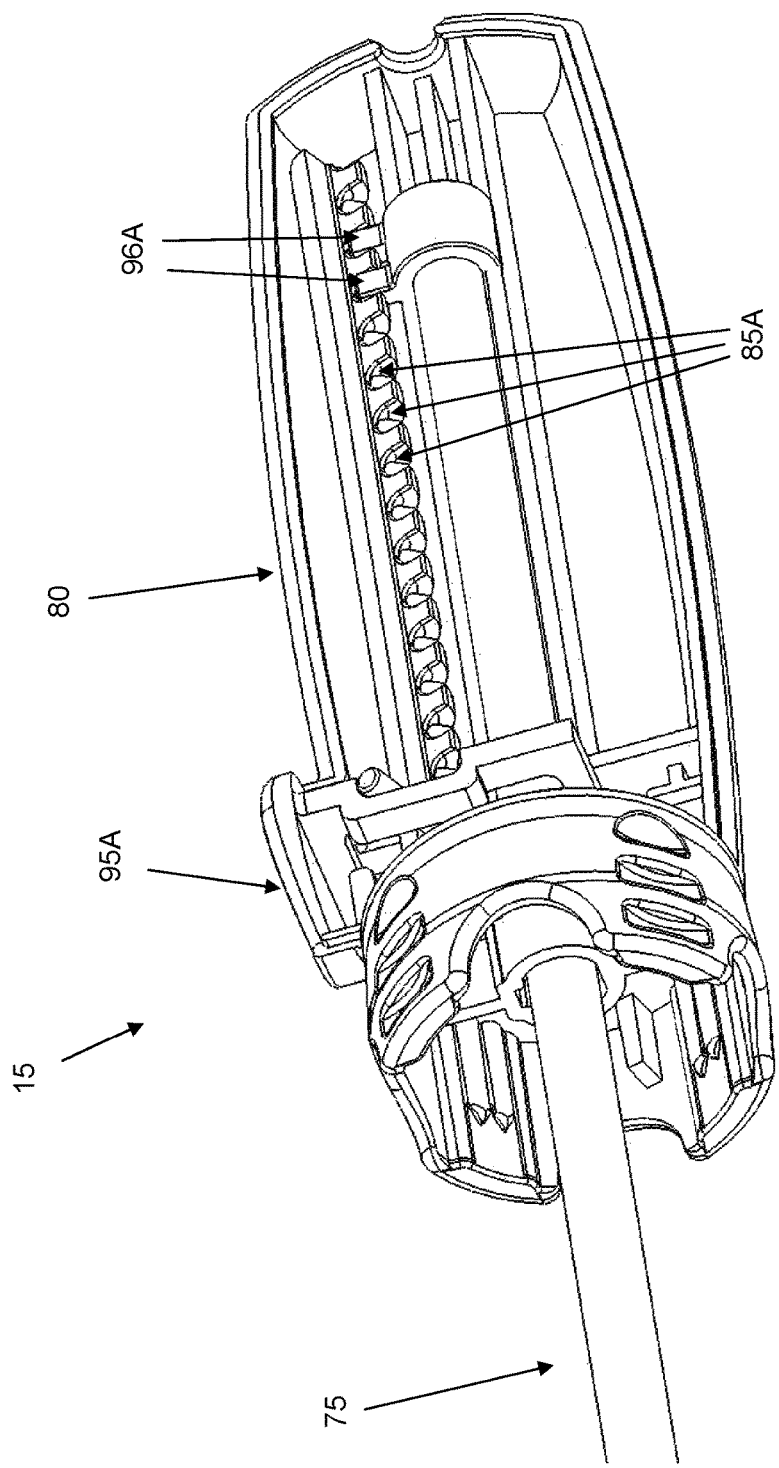

FIGS. 66-68 show an additional telescoping obturator construction. More particularly, the telescoping obturator shown in FIGS. 66-68 is substantially the same as the telescoping obturator 15 discussed above, except that handle 80 comprises openings 85A and shaft 75 includes fingers 96A. In this form of the invention, the disposition of shaft 75 vis-à-vis handle 80 is adjusted by (i) moving openings 85A away from fingers 96A, (ii) adjusting the disposition of shaft 75 relative to handle 80, and (iii) moving openings 85A towards fingers 96A. In this embodiment, a movable rack comprising openings 85A is activated by the pressing of button 95A, e.g., actuation of button 95A causes the movable rack (carrying openings 85A) to rotate out of alignment with fingers 96A, and the release of button 95A causes the movable rack (carrying openings 85A) to rotate back into alignment with fingers 96A.

Figure 69:
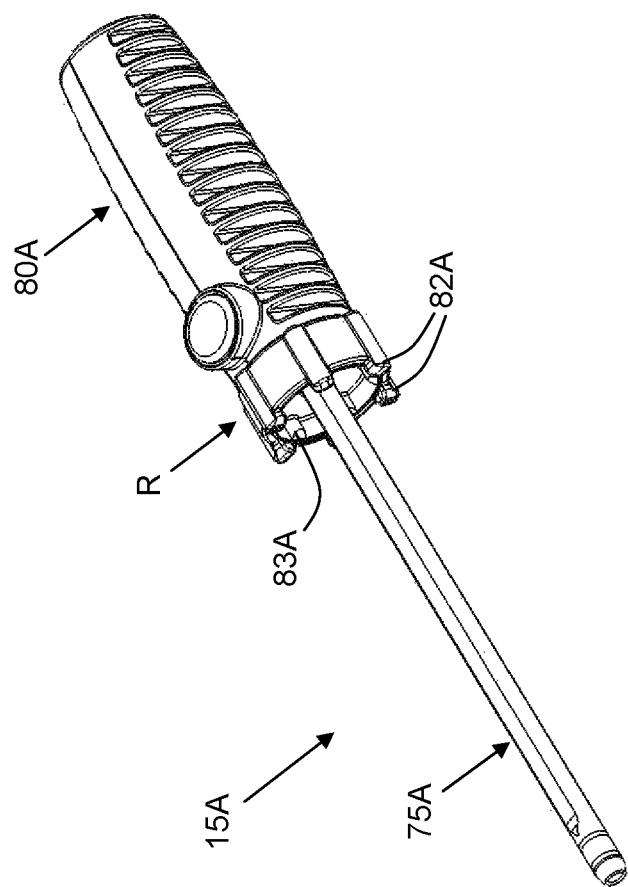
Figure 70:
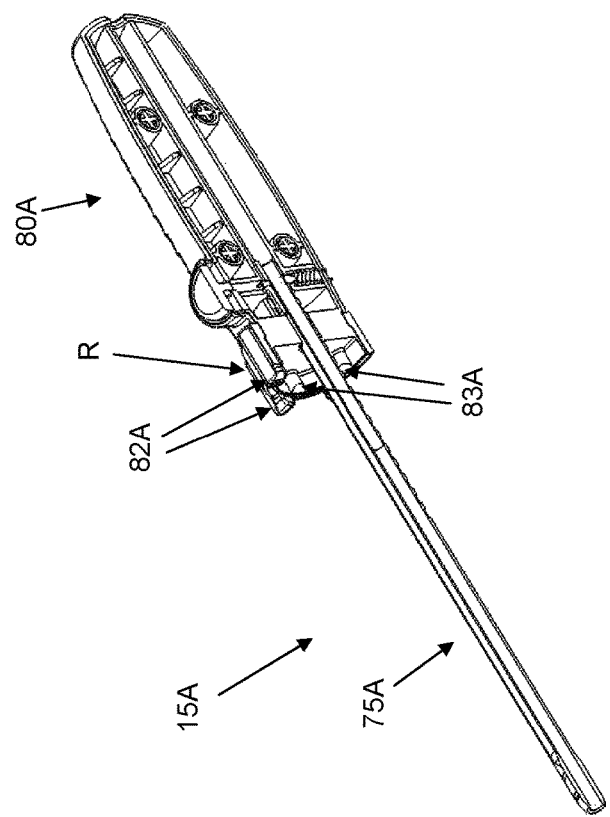
Figure 71:
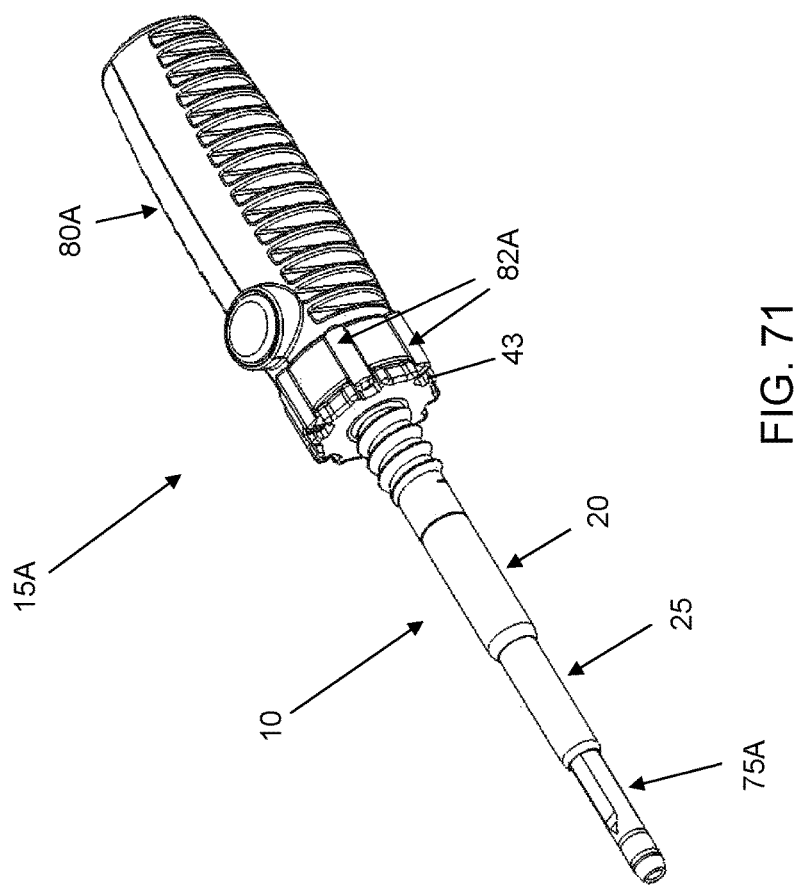
Figure 72:
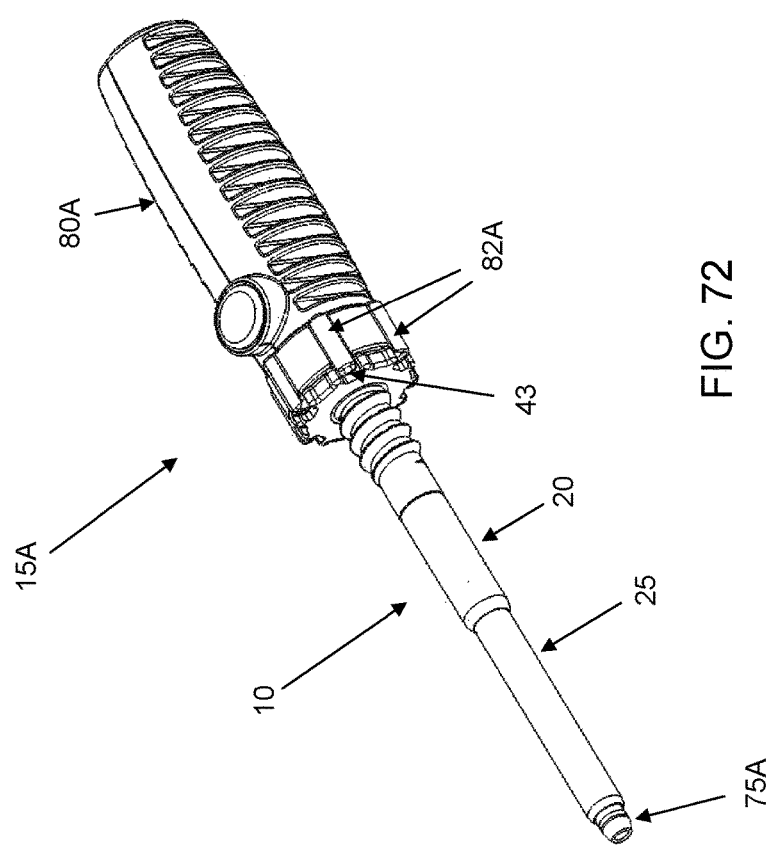

FIGS. 69-72 show yet another telescoping obturator construction. More particularly, the telescoping obturator 15A shown in FIGS. 69-72 is substantially the same as the telescoping obturator 15 discussed above, except that it further comprises an adjustment ring R (FIG. 69). The adjustment ring R is coupled to the obturator handle 80A but is capable of rotating relative to the handle, i.e., about shaft 75A. The adjustment ring R has keys 82A which engage the keyways 43 in the telescoping access cannula 10 such that when the telescoping access cannula 10 is mounted onto telescoping obturator 15A, keys 82A matingly engage keyways 43 (FIG. 71). Telescoping obturator 15A further comprises keys 83A which are coupled to handle 80A and not to adjustment ring R; thus, when adjustment ring R is rotated about handle 80A, keys 83A do not rotate (FIG. 69). When telescoping access cannula 10 is mounted onto telescoping obturator 15A, keys 83A engage keyways 43 of the telescoping access cannula 10. Thus, when the adjustment ring R is rotated, the outer tube 20 rotates, but cap 70 does not rotate. This effectively is the same action as rotating cap 70 while keeping outer tube 25 stationary; both will change the overall length of telescoping access cannula 10. FIG. 72 illustrates the telescoping access cannula 10 in a lengthened state as compared to FIG. 71.

In operation, the telescoping obturator 15A is adjusted to the desired length; this contrasts to the telescoping access cannula 10 being adjusted in length first as described above. The telescoping access cannula 10 is then mounted onto the telescoping obturator 15A. Then the adjustment ring R of the telescoping obturator 15A is rotated so as to adjust the length of the telescoping access cannula 10 to the correct length. Specifically, this is achieved by aligning the distal end of the telescoping access cannula 10 to a marker or designated location at the distal end of the shaft 75A of the telescoping obturator 15A.

Some Aspects of the Telescoping Access Cannula

Thus it will be seen that the present invention provides numerous approaches for adjusting the length of the telescoping access cannula, both in-situ and non in-situ. Furthermore, the present invention provides numerous approaches for effecting a desired surgical task, including but not limited to: (i) new and improved approaches for protecting tissue structures between the surface of the skin and the interior of a joint, and/or (ii) measuring the distance between the surface of the skin and the capsule of the joint, adjusting the length of the telescoping access cannula according to the measured distance, and then inserting the telescoping access cannula into tissue, and/or (iii) adjusting the length of the telescoping access cannula in-situ, and/or (iv) adjusting the position of the distal end of the telescoping access cannula in-situ, without moving the proximal end of the telescoping access cannula, etc.

Use of the Telescoping Access Cannula for Other Applications

It should be appreciated that the novel telescoping access cannula of the present invention may be used for accessing joints other than the hip joint (e.g., the telescoping access cannula may be used to access the shoulder joint), and/or for accessing other interior body spaces (e.g., the abdominal cavity).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus comprising a telescoping obturator for use with an access cannula having a distal end, a proximal end and a lumen extending therebetween, the telescoping obturator comprising:
a handle having a distal end and a proximal end;
a shaft carried by the handle, the shaft being longitudinally movable relative to the handle;
a locking mechanism for selectively locking the shaft to the handle at a plurality of longitudinal positions along the length of the shaft;
wherein the distal end of the handle comprises at least one first feature for engaging at least one second feature on the proximal end of the access cannula, whereby to enable the handle to transmit both axial force and rotational force to the proximal end of the access cannula when the handle is connected to the proximal end of the access cannula.

2. Apparatus according to claim 1 wherein the locking mechanism comprises an element which is movable into and out of an opening.

3. Apparatus according to claim 2 wherein the element is movable into the opening via linear motion.

4. Apparatus according to claim 2 wherein the element is movable into the opening via rotational motion.

5. Apparatus according to claim 1 wherein the locking mechanism comprises an opening formed in the handle, and a finger movably mounted to the shaft.

6. Apparatus according to claim 5 wherein the element is carried by the handle and movable into the opening in the shaft.

7. Apparatus according to claim 6 wherein the element is movable into the opening via linear motion.

8. Apparatus according to claim 6 wherein the element is movable into the opening via rotational motion.

9. Apparatus according to claim 1 wherein the shaft of the telescoping obturator comprises a proximal end and a distal end, the proximal end being connected to the handle, and the distal end forming a blunt end.

10. A system for accessing an interior space within a body, the system comprising:
an access cannula, the access cannula comprising a distal end, a proximal end and a lumen extending therebetween; and
a telescoping obturator, the telescoping obturator comprising:
a handle having a distal end and a proximal end;
a shaft carried by the handle, the shaft being longitudinally movable relative to the handle;
a locking mechanism for selectively locking the shaft to the handle at a plurality of longitudinal positions along the length of the shaft;
wherein the distal end of the handle comprises at least one first feature for engaging at least one second feature on the proximal end of the access cannula, whereby to enable the handle to transmit both axial force and rotational force to the proximal end of the access cannula when the handle is connected to the proximal end of the access cannula.

11. A system according to claim 10 wherein the locking mechanism comprises an element which is movable into and out of an opening.

12. A system according to claim 11 wherein the element is movable into the opening via linear motion.

13. A system according to claim 11 wherein the element is movable into the opening via rotational motion.

14. A system according to claim 10 wherein the shaft of the telescoping obturator comprises a proximal end and a distal end, the proximal end being connected to the handle, and the distal end forming a blunt end.

15. A system according to claim 10 wherein the access cannula is user-sizable.

16. A system according to claim 15 wherein the length of the lumen of the access cannula is configured to be sized prior to being advanced into the interior of a joint.

17. A system according to claim 15 wherein the shaft of the telescoping obturator is positioned relative to the handle of the telescoping obturator so that the shaft extends beyond the distal end of the access cannula.

18. A system according to claim 10 further comprising a switching stick.

19. A system according to claim 18 wherein the switching stick comprises length markers.

20. A system according to claim 10 wherein the shaft of the telescoping obturator is cannulated.

21. Apparatus according to claim 1 wherein the at least one first feature comprises at least one of a key and a keyway, and further wherein the at least one second feature comprises at least one of a counterpart keyway or key, respectively.

22. A system according to claim 10 wherein the at least one first feature comprises at least one of a key and a keyway, and further wherein the at least one second feature comprises at least one of a counterpart keyway or key, respectively.

23. Apparatus according to claim 2 wherein the element is movably mounted to the handle, and the opening is formed in the shaft.

24. Apparatus according to claim 1 wherein the shaft of the telescoping obturator is cannulated.

25. A system according to claim 11 wherein the element is movably mounted to the handle, and the opening is formed in the shaft.

26. A system according to claim 25 wherein the locking mechanism comprises a spring for biasing the element into the opening, thereby locking the shaft to the handle.

27. A system according to claim 26 further comprising a release mechanism disposed on the handle for moving the element out of the opening in the shaft, thereby unlocking the shaft from the handle.

28. Apparatus according to claim 23 wherein the locking mechanism comprises a spring for biasing the element into the opening, thereby locking the shaft to the handle.

29. Apparatus according to claim 28 further comprising a release mechanism disposed on the handle for moving the element out of the opening in the shaft, thereby unlocking the shaft from the handle.

30. Apparatus according to claim 29 wherein the release mechanism comprises a button for moving the element against the bias of the spring and out of the opening.

31. A system according to claim 27 wherein the release mechanism comprises a button for moving the element against the bias of the spring and out of the opening.

32. Apparatus according to claim 1 wherein the access cannula is user-sizable.

33. Apparatus according to claim 32 wherein the length of the lumen of the access cannula is configured to be sized prior to being advanced into the interior of a joint.

34. Apparatus according to claim 32 wherein the shaft of the telescoping obturator is positioned relative to the handle of the telescoping obturator so that the shaft extends beyond the distal end of the access cannula.

35. An assembly comprising:
an access cannula, the access cannula comprising a distal end, a proximal end and a lumen extending therebetween; and
a telescoping obturator, the telescoping obturator comprising:
a handle having a distal end and a proximal end;
a shaft carried by the handle, the shaft being longitudinally movable relative to the handle; and
a locking mechanism for selectively locking the shaft to the handle at a plurality of longitudinal positions along the length of the shaft;
wherein the distal end of the handle comprises at least one first feature for engaging at least one second feature on the proximal end of the access cannula, whereby to enable the handle to transmit both axial force and rotational force to the proximal end of the access cannula when the handle is connected to the proximal end of the access cannula;
wherein the length of the telescoping obturator is sized according to the length of the access cannula.

36. The assembly according to claim 35 wherein the locking mechanism comprises an element which is movable into and out of an opening.

37. The assembly according to claim 36 wherein the element is movably mounted to the handle, and the opening is formed in the shaft.

38. The assembly according to claim 37 wherein the locking mechanism comprises a spring for biasing the element into the opening, thereby locking the shaft to the handle.

39. The assembly according to claim 38 further comprising a release mechanism disposed on the handle for moving the element out of the opening in the shaft, thereby unlocking the shaft from the handle.

40. The assembly according to claim 36 wherein the element is movable into the opening via linear motion.

41. The assembly according to claim 36 wherein the element is movable into the opening via rotational motion.

42. The assembly according to claim 39 wherein the release mechanism comprises a button for moving the element against the bias of the spring and out of the opening.

43. The assembly according to claim 35 wherein the shaft of the telescoping obturator comprises a proximal end and a distal end, the proximal end being connected to the handle, and the distal end forming a blunt end.

44. The assembly according to claim 35 wherein the shaft of the telescoping obturator is cannulated.

45. The assembly according to claim 35 wherein the access cannula is user-sizable.

46. The assembly according to claim 45 wherein the length of the lumen of the access cannula is configured to be sized prior to being advanced into the interior of a joint.

47. The assembly according to claim 45 wherein the shaft of the telescoping obturator is positioned relative to the handle of the telescoping obturator so that the shaft extends beyond the distal end of the access cannula.

48. The assembly according to claim 35 further comprising a switching stick.

49. The assembly according to claim 48 wherein the switching stick comprises length markers.

50. The assembly according to claim 35 wherein the at least one first feature comprises at least one of a key and a keyway, and further wherein the at least one second feature comprises at least one of a counterpart keyway or key, respectively.

51. A method for forming an assembly, the method comprising:
providing:
an access cannula, the access cannula comprising a distal end, a proximal end and a lumen extending therebetween; and
a telescoping obturator, the telescoping obturator comprising:
a handle having a distal end and a proximal end;
a shaft carried by the handle, the shaft being longitudinally movable relative to the handle; and
a locking mechanism for selectively locking the shaft to the handle at a plurality of longitudinal positions along the length of the shaft;
wherein the distal end of the handle comprises at least one first feature for engaging at least one second feature on the proximal end of the access cannula, whereby to enable the handle to transmit both axial force and rotational force to the proximal end of the access cannula when the handle is connected to the proximal end of the access cannula;
sizing the length of the access cannula to a desired length;
inserting the telescoping obturator into the lumen of the access cannula; and
sizing the length of the telescoping obturator according to the length of the access cannula.

52. The method according to claim 51 wherein the locking mechanism comprises an element which is movable into and out of an opening.

53. The method according to claim 52 wherein the element is movably mounted to the handle, and the opening is formed in the shaft.

54. The method according to claim 53 wherein the locking mechanism comprises a spring for biasing the element into the opening, thereby locking the shaft to the handle.

55. The method according to claim 54 further comprising a release mechanism disposed on the handle for moving the element out of the opening in the shaft, thereby unlocking the shaft from the handle.

56. The method according to claim 52 wherein the element is movable into the opening via linear motion.

57. The method according to claim 52 wherein the element is movable into the opening via rotational motion.

58. The method according to claim 55 wherein the release mechanism comprises a button for moving the element against the bias of the spring and out of the opening.

59. The method according to claim 51 wherein the shaft of the telescoping obturator comprises a proximal end and a distal end, the proximal end being connected to the handle, and the distal end forming a blunt end.

60. The method according to claim 51 wherein the shaft of the telescoping obturator is cannulated.

61. The method according to claim 51 wherein the access cannula is user-sizable.

62. The method according to claim 61 wherein the length of the lumen of the access cannula is sized prior to advancing the assembly into the interior of a joint.

63. The method according to claim 61 wherein the shaft of the telescoping obturator is positioned relative to the handle of the telescoping obturator so that the shaft extends beyond the distal end of the access cannula.

64. The method according to claim 51 wherein the desired length of the access cannula is determined by using a switching stick.

65. The method according to claim 64 wherein the switching stick comprises length markers.

66. The method according to claim 51 wherein the at least one first feature comprises at least one of a key and a keyway, and further wherein the at least one second feature comprises at least one of a counterpart keyway or key, respectively.

* * * * *